US011278555B2

(12) United States Patent
Scherz et al.

(10) Patent No.: US 11,278,555 B2
(45) Date of Patent: Mar. 22, 2022

(54) COMBINATIONAL THERAPIES FOR TREATMENT OF CANCER COMPRISING A BACTERIOCHLOROPHYLL DERIVATIVE

(71) Applicants: Yeda Research and Development Co. Ltd., Rehovot (IL); Memorial Sloan-Kettering Cancer Center, New York, NY (US)

(72) Inventors: Avigdor Scherz, Rehovot (IL); Yoram Salomon, Rehovot (IL); Lilach Agemy, Rehovot (IL); Rachel Hamri, Rehovot (IL); Dina Preise, Rehovot (IL); Kwanghee Kim, Long Island City, NY (US); Jonathan Coleman, Scarsdale, NY (US)

(73) Assignees: YEDA RESEARCH AND DEVELOPMENT CO. LTD., Rehovot (IL); MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/092,742

(22) PCT Filed: Apr. 10, 2017

(86) PCT No.: PCT/IL2017/050440
§ 371 (c)(1),
(2) Date: Oct. 10, 2018

(87) PCT Pub. No.: WO2017/179053
PCT Pub. Date: Oct. 19, 2017

(65) Prior Publication Data
US 2019/0125769 A1    May 2, 2019

Related U.S. Application Data

(60) Provisional application No. 62/320,549, filed on Apr. 10, 2016.

(51) Int. Cl.
| | | |
|---|---|---|
| *A61K 31/675* | (2006.01) | |
| *A61K 31/409* | (2006.01) | |
| *A61K 31/7068* | (2006.01) | |
| *A61K 31/7135* | (2006.01) | |
| *A61K 45/06* | (2006.01) | |
| *A61P 35/00* | (2006.01) | |

(52) U.S. Cl.
CPC .......... *A61K 31/675* (2013.01); *A61K 31/409* (2013.01); *A61K 31/7068* (2013.01); *A61K 31/7135* (2013.01); *A61K 45/06* (2013.01); *A61P 35/00* (2018.01)

(58) Field of Classification Search
USPC ........................................................ 514/80
See application file for complete search history.

(56) References Cited

U.S. PATENT DOCUMENTS 7,947,672 B2 * 5/2011 Scherz .................. A61K 31/40
514/184
2012/0323163 A1   10/2012 Chen

FOREIGN PATENT DOCUMENTS

| CN | 102002048 A | 4/2011 |
| WO | 200140232 A1 | 6/2001 |
| WO | 2004/045492 A2 | 6/2004 |
| WO | 2004045492 A2 | 6/2004 |
| WO | 2008023378 A1 | 2/2008 |
| WO | 2012106343 A2 | 8/2012 |
| WO | 2014141289 A1 | 9/2014 |

OTHER PUBLICATIONS

Min (Gemcitabine Therapy in Patients with Advanced Pancreatic Cancer, The Korean Journal of Internal Medicine vol. 17, No. 4, Dec. 2002).*
PCT International Search Report from PCT/IL2017/050440 dated Sep. 26, 2017 (12 pages).
PCT International Preliminary Report on Patentability from PCT/IL2017/050440 dated Oct. 16, 2018 (16 pages).
Agemy et al., 2016, "Enhancing antitumor immunity by photodynamic therapy with gemcitabine in metastatic 4T1 breast tumor," Ann Oncol 27(Suppl_9); 2 pages.
Anand et al., 2012, "Biomodulatory approaches to photodynamic therapy for solid tumors," Cancer Lett 326(1):8-16.
Briggs et al., 2003, "The effect of combination treatment with gemcitabine and the EGFR-receptor tyrosine kinase inhibitor iressa with photodynamic therapy in bladder cancer," European Urology Supplements, 2(1):44.
Crescenzi et al., 2006, "Low doses of cisplatin or gemcitabine plus Photofrin/photodynamic therapy: Disjointed cell cycle phase-related activity accounts for synergistic outcome in metastatic non-small cell lung cancer cells (H1299)," Mol Cancer Ther 5(3):776-785.
Kelleher et al., 2003, "Combined hyperthermia and chlorophyll-based photodynamic therapy: tumour growth and metabolic microenvironment," Br J Cancer 89(12):2333-2339.
Mazor et al., 2005, "WST11, A Novel Water-soluble Bacteriochlorophyll Derivative; Cellular Uptake, Pharmacokinetics, Biodistribution and Vascular-targeted Photodynamic Activity Using Melanoma Tumors as a Model," Photochem Photobiol 81(2):342-351.
Moore et al., 2009, "Photodynamic therapy for prostate cancer—a review of current status and future promise," Nat Clin Pract Urol 6(1):18-30.
Mroz et al., 2009, "New stable synthetic bacteriochlorins for photodynamic therapy of melanoma," Proc SPIE 7380, Photodynamic Therapy: Back to the Future, 73802S1-73802S14.

(Continued)

*Primary Examiner* — Kathrien A Cruz
(74) *Attorney, Agent, or Firm* — Browdy and Neimark, PLLC

(57) ABSTRACT

An anti-myeloid-derived suppressor cells agent ("anti-MDSCs agent") and a bacteriochlorophyll derivative (hereinafter "Bchl-D") for use in combination therapy for cancer, wherein the anti-MDSC agent and the Bchl-D are administered sequentially and the administration of the Bchl-D is followed by photodynamic therapy (PDT) or vascular targeted PDT (VTP).

18 Claims, 40 Drawing Sheets
(22 of 40 Drawing Sheet(s) Filed in Color)

(56) References Cited

OTHER PUBLICATIONS

Nonaka et al., 2013, "Synergic effect of photodynamic therapy using talaporfin sodium with conventional anticancer chemotherapy for the treatment of bile duct carcinoma," J Surg Res 181(2):234-241.
Park et al., 2012 "Su2031 Comparison Outcomes for Unresectable Hilar Cholangiocarcinoma Treated With Definitive Photodynamic Therapy (PDT)Combined With Gemcitabine-Based Chemotherapy and Conservative Treatment," Gastroenterology 142(5):S-977; 1 page.
Preise et al., 2009, "Systemic antitumor protection by vascular-targeted photodynamic therapy involves cellular and humoral immunity," Cancer Immunol Immunother 58(1):71-84.
Sun et al., 2012, "Synergistic effects of photodynamic therapy with HPPH and gemcitabine in pancreatic cancer cell lines," Lasers Surg Med 44: 755-761.
Van Geel et al., 1995, "Mechanisms for optimising photodynamic therapy: second-generation photosensitisers in combination with mitomycin C," Br J Cancer 72:344-350.
Van Straten et al., 2017, "Oncologic Photodynamic Therapy: Basic Principles, Current Clinical Status and Future Directions," Cancers 9(2) 19; 54 pages.
Xie et al., 2009, "Synergetic anticancer effect of combined gemcitabine and photodynamic therapy on pancreatic cancer in vivo," World J Gastroenterol 15(6):737-741.
Toschi et al., "Role of gemcitabine in cancer therapy," 2005, Future Oncol 1(1):7-17.
Castano et al., "Photodynamic therapy plus low-dose cyclophosphamide generates antitumor immunity in a mouse model," Proc Natl Acad Sci USA., 2008, 105(14):5495-5500.
Goldshaid et al., "Novel design principles enable specific targeting of imaging and therapeutic agents to necrotic domains in breast tumor," Breast Cancer Research, 2010, 1:1-18.
Hanahan et al., Less is more, regularly: metronomic dosing of cytotoxic drugs can target tumor angiogenesis in mice, The Journal of clinical investigation, 105:1045-1047 (2000).
Tongu et al., Metronomic chemotherapy with low-dose cyclophosphamide plus gemcitabine can induce anti-tumor T cell immunity in vivo, Cancer Immunol. Immunother., 62:383-391 (2013).
Biziota et al., Metronomic chemotherapy: A potent macerator of cancer by inducing angiogenesis suppression and antitumor immune activation, Cancer letters, 400:243-251 (2017).
Ge et al., Metronomic cyclophosphamide treatment in metastasized breast cancer patients: immunological effects and clinical outcomeCancer Immunol. Immunother., 61:353-362 (2012).
Ghiringhelli et al., Metronomic cyclophosphamide regimen selectively depletes CD4+CD25+ regulatory T cells and restores T and NK eVector functions in end stage cancer patientsCancer Immunol. Immunother., 56:641-648 (2007).
Gross et al., Monitoring photodynamic therapy of solid tumors online by BOLD-contrast MRI, Nature medicine, 9:1327-1331 (2003).
Koudinova et al., Photodynamic Therapy With Pd-Bacteriopheophorbide (TOOKAD): Successful In Vivo Treatment of Human Prostatic Small Cell Carcinoma Xenografts, Int. J. Cancer, 104:782-789 (2003).
Yang et al., Targeting Antitumor Immune Response for Enhancing the Efficacy of Photodynamic Therapy of Cancer: Recent Advances and Future PerspectivesOxidative Medicine and Cellular Longevity, 1-11 (2016).
Ciccolini et al., Pharmacokinetics and pharmacogenetics of Gemcitabine as a mainstay in adult and pediatric oncology: an EORTC-PAMM perspective, Cancer chemotherapy and pharmacology, 78:1-12 (2016).
Peters et al., Clinical Phase I and Pharmacology Study of Gemcitabine (2', 2'-Difluorodeoxycytidine) Administered in a Two-Weekly Schedule, Journal of chemotherapy, 19:212-221 (2007).
Maiti, Metronomic chemotherapy, J Pharmacol Pharmacother., 5:186-192 (2014).
Hanahan and Weinberg, Hallmarks of Cancer: The Next Generation, Cell, 144:646-74 (2011).
Office Action in Chinese application No. 201780035366.4, dated Feb. 11, 2020.
Office Action in Korean application No. 10-2018-7032029, dated Apr. 8, 2021.

* cited by examiner

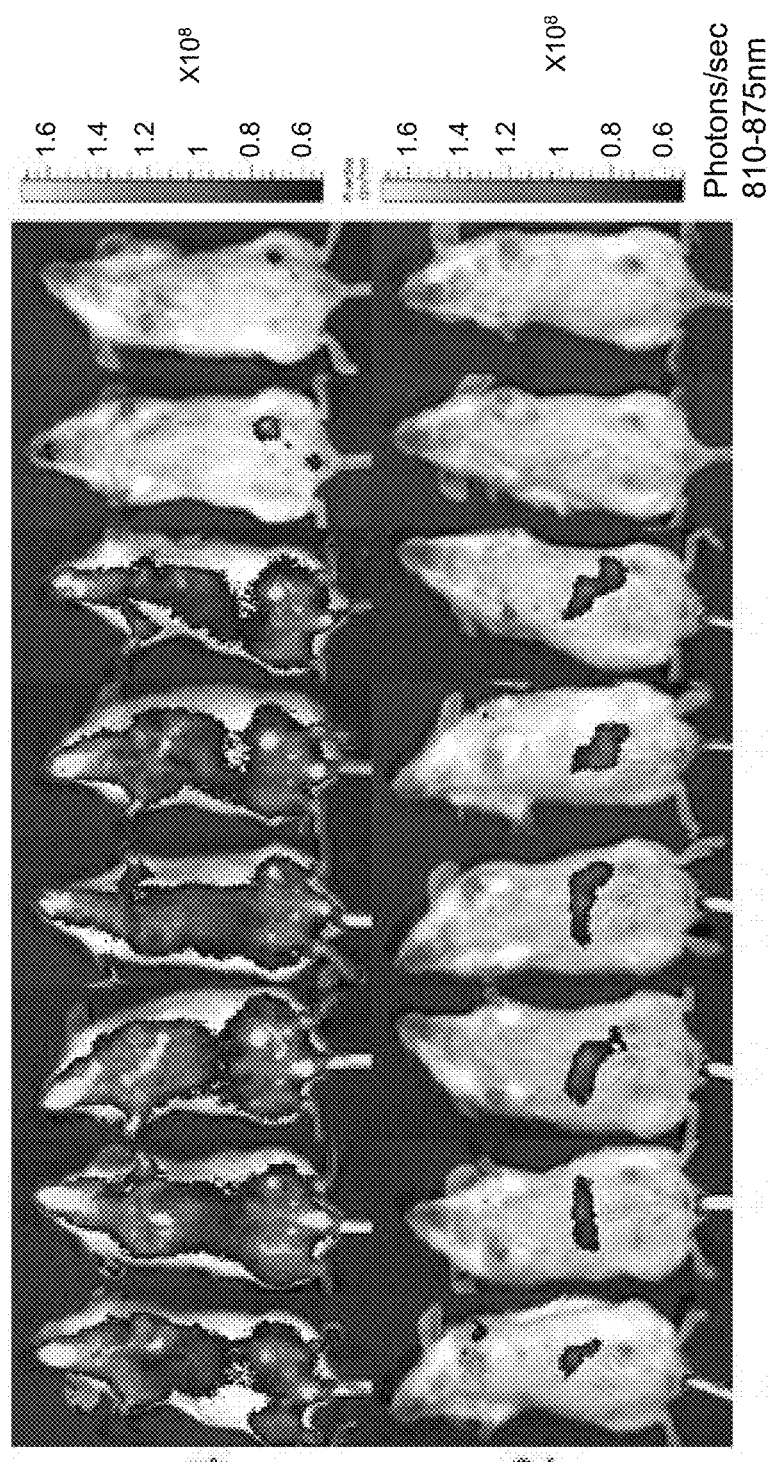

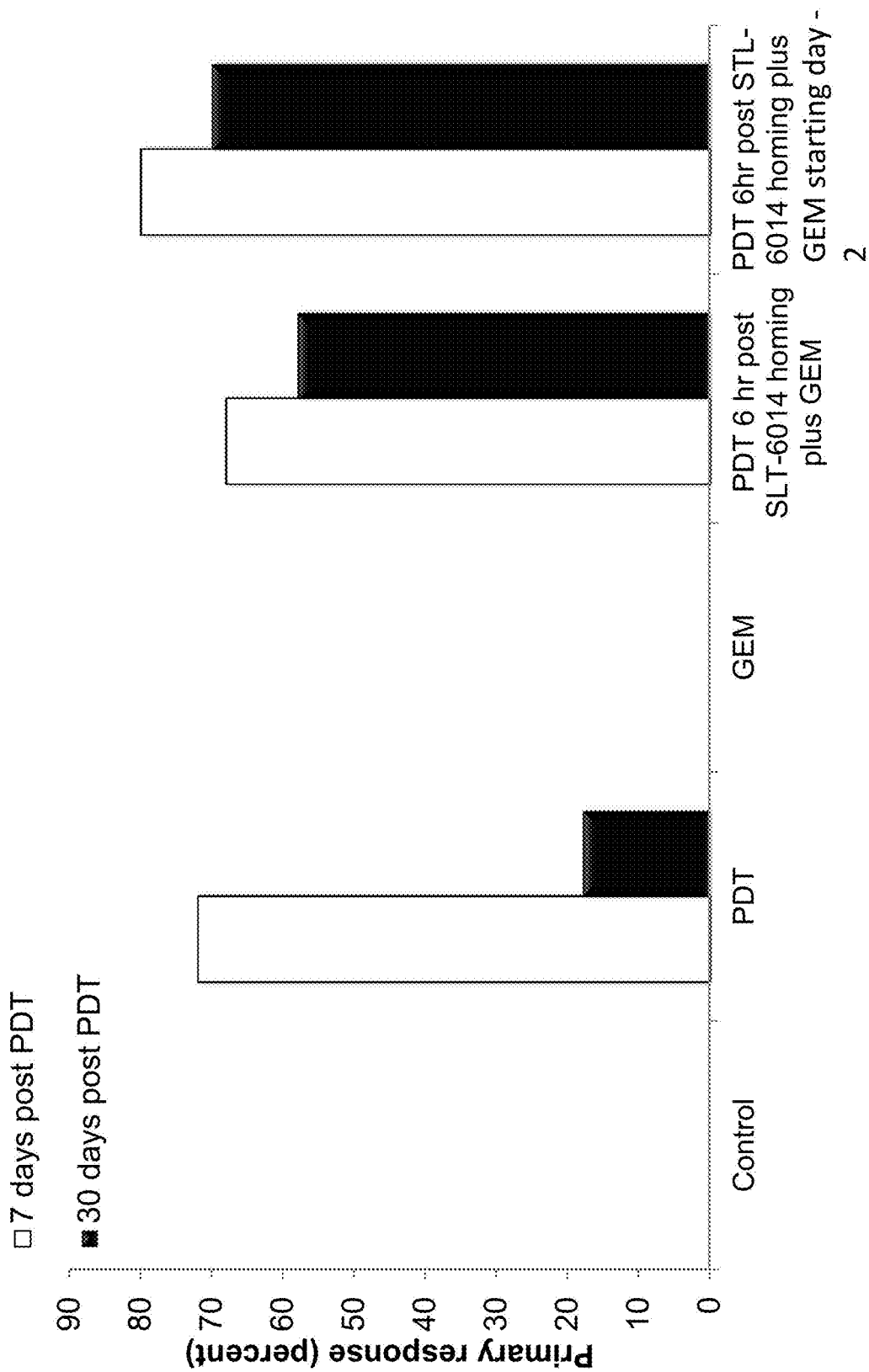

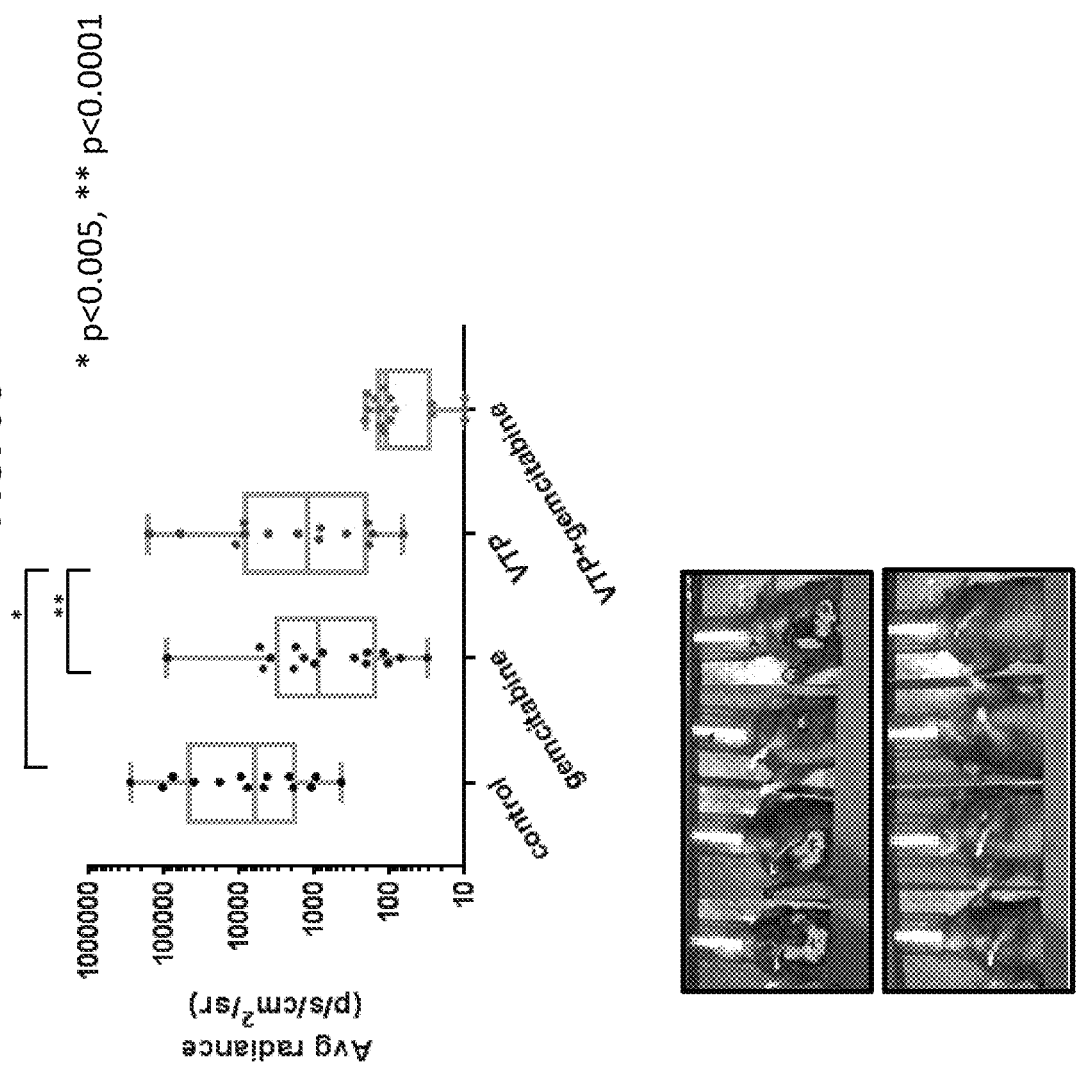

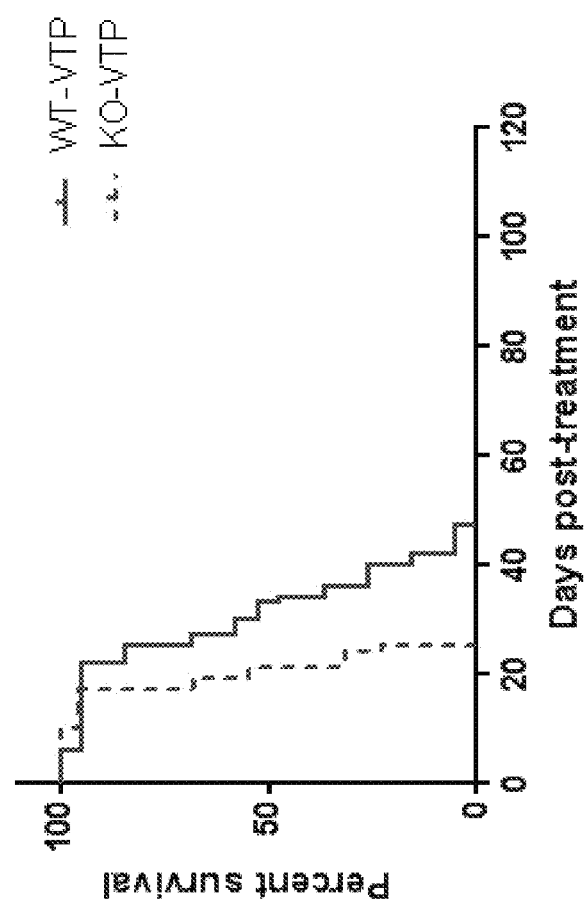

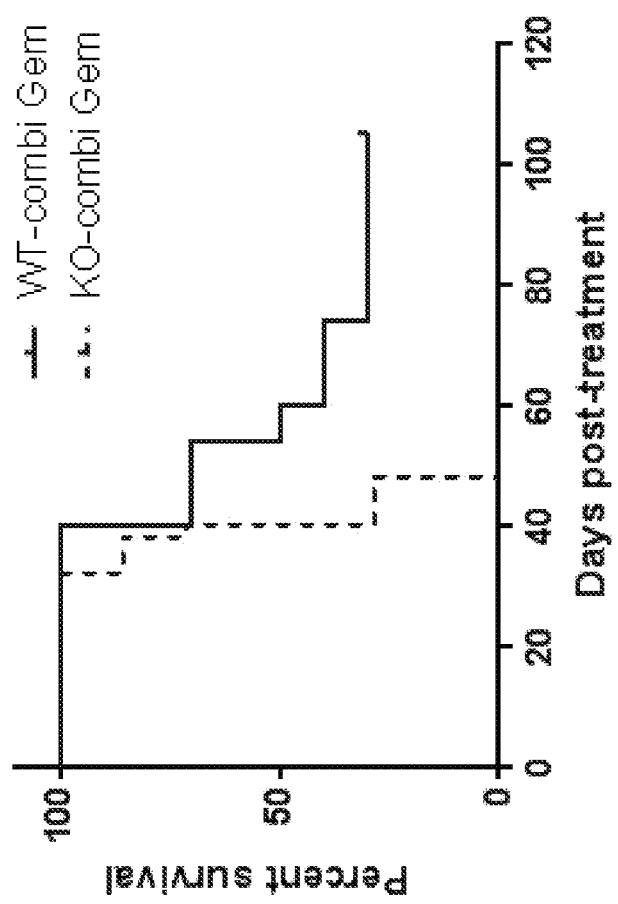

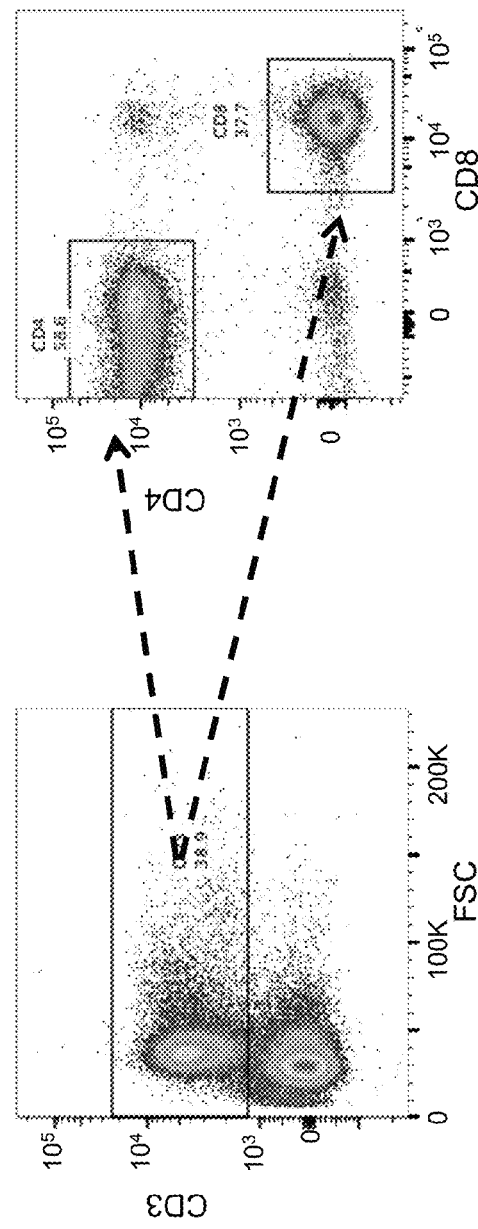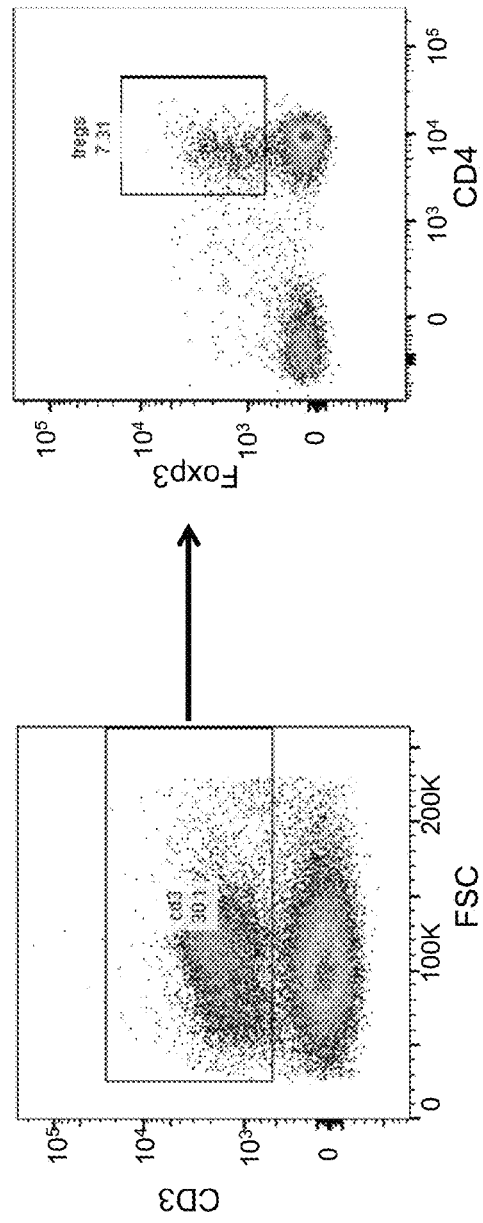

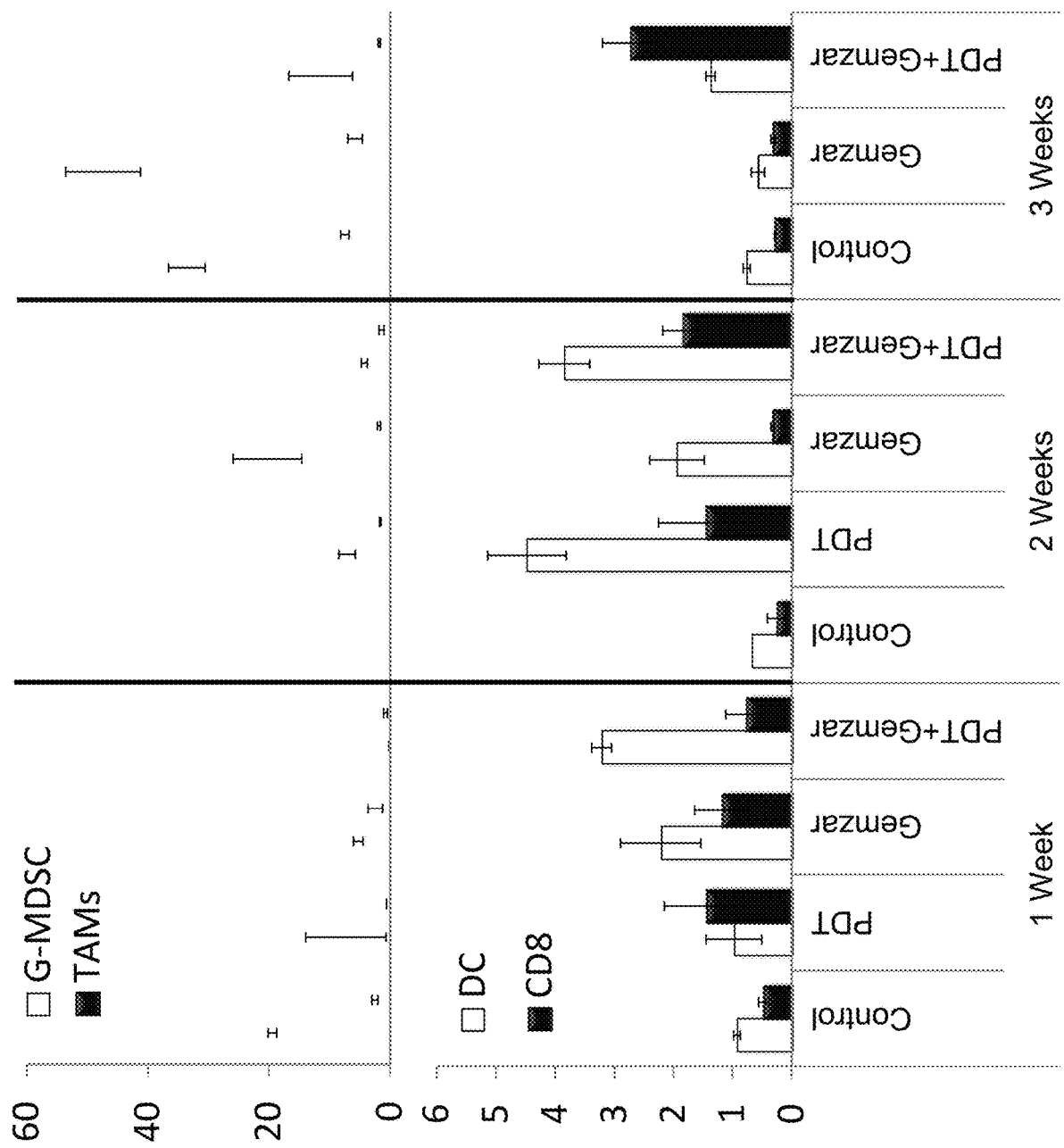

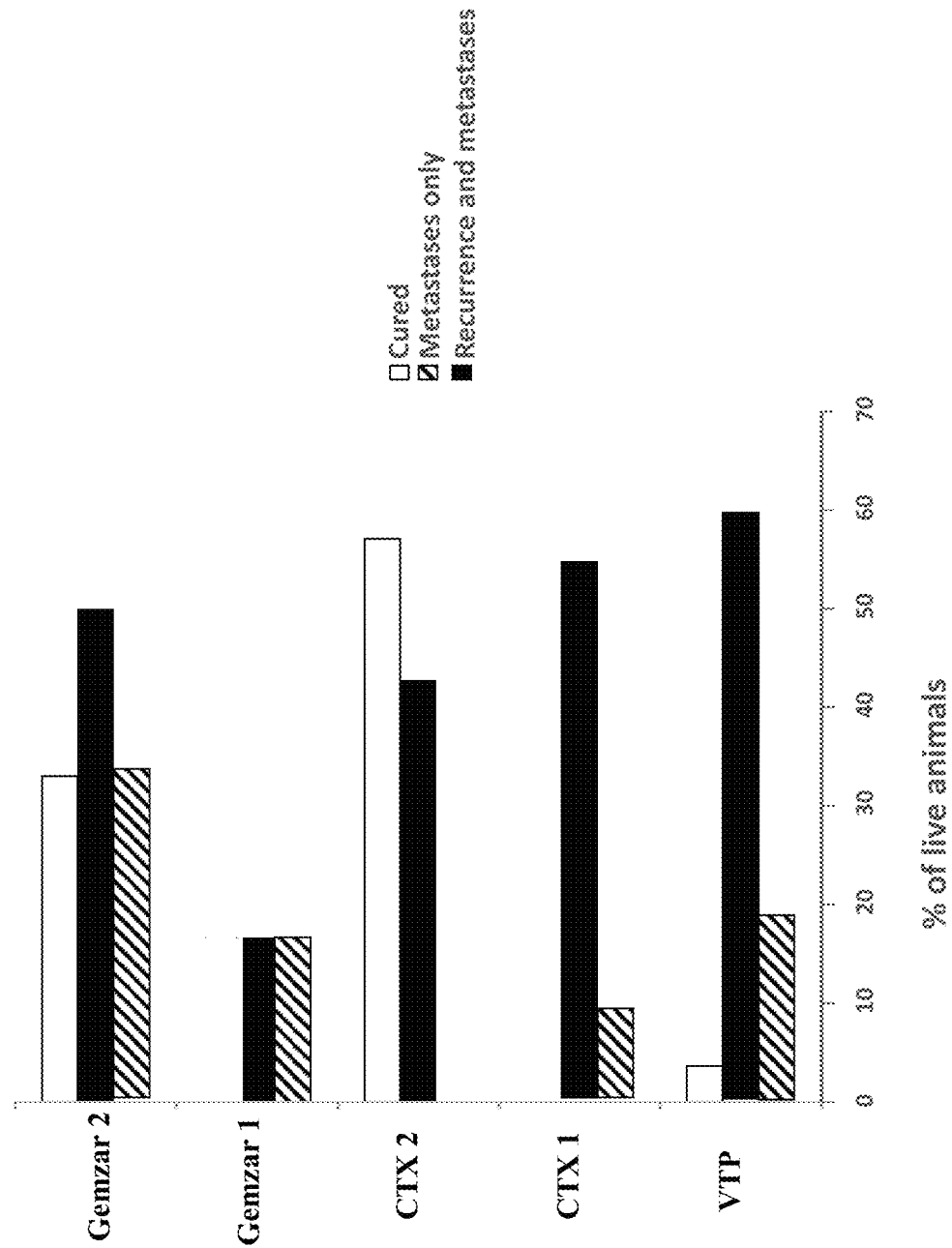

COMBINATIONAL THERAPIES FOR TREATMENT OF CANCER COMPRISING A BACTERIOCHLOROPHYLL DERIVATIVE

CROSS REFERENCE TO RELATED APPLICATIONS

This application is a National Stage of International Application No. PCT/IL2017/050440, filed Apr. 10, 2017, which claims the benefit under 35 U.S.C. § 119(e) of U.S. Provisional Application No. 62/320,549, filed Apr. 10, 2016, the contents of all of which are incorporated herein in their entireties by reference thereto.

FIELD OF THE INVENTION

The present invention relates to treatment of cancer and to combinational therapies therefor.

DEFINITIONS AND ABBREVIATIONS: Bchl: bacteriochlorophyll; Bchl-D: bacteriochlorophyll derivative; BLI, bioluminescence imaging; Bpheid: bacteriopheophorbide a (the $C-17^2$-free carboxylic acid derived from Bphe without the central metal atom); CTX, CY: cyclophosphamide; DC: dendritic cells; DDW, double distilled water; GEM: Gemzar, gemcitabine; GFP, Green Fluorescent Protein; IVIS, In Vivo Optical Imaging System; Luc, luciferin, luciferase; IVIS, In Vivo Optical Imaging System; luc, luciferase; Ly6G, lymphocyte antigen 6 complex is a 21-25 kD glycosylphosphatidylinositol (GPI)-linked differentiation antigen that is expressed by myeloid-derived cell; Ly6G, lymphocyte antigen 6 complex is a 21-25 kD glycosylphosphatidylinositol (GPI)-linked differentiation antigen that is expressed by myeloid-derived cell; MDSCs: myeloid-derived suppressor cells; Rhodobacteriochlorin: tetracyclic 7,8,17,18-tetrahydroporphyrin having a $CH_2CH_2COOH$ group at position 17, a —COOH at position 13, methyl groups at positions 2, 7, 12, 8, and ethyl groups at positions 3 and 8; Pd-Bpheid: Pd-bacteriopheophorbide a; NIR: near-infrared; PDT: photodynamic therapy; RGD-4C: the cyclic nonapeptide CDCRGDCFC-$NH_2$; ROS: reactive oxygen species; VTP: vascular-targeted PDT;

BACKGROUND

Combination of therapeutic modalities that target the cancer and the immune suppressing cells constitute a promising avenue for controlling primary tumors growth and for preventing metastatic growth.

Myeloid-derived suppressor cells (MDSCs) are a heterogeneous population of cells that are defined by their myeloid origin, immature state and ability to potently suppress T cell responses. They regulate immune responses and tissue repair in healthy individuals and the population rapidly expands during inflammation, infection and cancer. MDSCs are broadly made up of two subsets—granulocytic (G-MDSC) and monocytic (M-MDSC), which morphologically resemble granulocytes and monocytes, respectively (Gabrilovich, 2017).

MDSCs exhibit potent immunosuppressive activities in cancer. MDSCs infiltrate tumors and strongly inhibit cancer-specific cytotoxic T cells (Gabrilovich, 2017). Tumors have evolved to 'harness' these properties of MDSCs to restrain antitumor immunity and to promote tumor expansion in the surrounding environment and at distant sites, through effects on angiogenesis and metastasis. New therapies to restrain MDSC activity are crucial for the efficient control of tumor cells by immune responses (Condamine et al., 2015; Diaz-Montero et al., 2009; Gabrilovich, 2017; Marvel and Gabrilovich, 2015; Najjar and Finke, 2013; Quail, 2013 #18).

Myeloid-derived suppressor cells (MDSC) of the mono or polymorphonuclear type promote immune suppression and thereby cancer cells evasion from anti-tumor immunity by neutralizing cytotoxic T cells through nitric oxide and peroxynitrite generation (Condamine et al., 2015; Gabrilovich and Nagaraj, 2009). In addition, the early differentiation of myeloid progenitor cells into MDSCs comes on the account of dendritic cells maturation (Gabrilovich, 2017) needed for professional presentation of tumor-associated antigens (TAAs), innate immunity and initiation of adaptive immunity response. The progression of breast, prostate, lung, kidney and other cancers from the early, localized stage to dissemination and metastases, was found tightly correlated with proliferation of MDSCs (in the patients' periphery, spleen, lymph nodes and the tumor microenvironment (Brusa et al., 2013; Condamine et al., 2015; Gabrilovich, 2017; Gabrilovich and Nagaraj, 2009; Najjar and Finke, 2013)). The MDSCs elevation augments immune suppression by blocking CD4 and CD8 T cell activation (Gabrilovich, 2017). This elevation has been primarily correlated with the secretion of cytokines such as G-CSF, GM-CSF, IL-6 and others from the cancer cells followed by autocrine stimulation through IL-6 and others from the MDSCs (Gabrilovich and Nagaraj, 2009). At increased concentrations, the MDSCs provide protection to the primary tumors and circulating cancer cells from immune surveillance and toxicity and help establishing the tumor niche.

Multiple methods of inhibiting MDSCs are currently under investigation. These can broadly be categorized into methods that (a) promote differentiation of MDSC into mature, non-suppressive cells (all-trans retinoic acid (ATRA), vitamin D) (Najjar and Finke, 2013), (b) decrease MDSC levels (sunitinib, gemcitabine (GEM), flurouracil (f-5U), bardoxolone methyl (CDDO-Me) (Najjar and Finke, 2013), or (c) functionally inhibit MDSC (phosphodiesterase type 5 (PDE-5) inhibitors, cyclooxygenase 2 (COX-2) inhibitors) (Najjar and Finke, 2013).

Gemcitabine (GEM, Gemzar), fluorouracil (f-5U) and other FDA-approved chemotherapeutic agents that are used for the treatment of a variety of cancers in the clinical arena, were found to selectively reduce the content of MDSC in both tumor-bearing mice and humans (Le et al., 2009; Suzuki et al., 2005; Vincent et al., 2010). However, despite a delay in cancer progression, none of these drugs was found to significantly increase time to metastases and patients survival (e.g. in treatment of pancreatic cancer).

Photodynamic therapy (PDT) in general and vascular-targeted PDT (VTP) in particular using novel bacteriochlorophyll derivatives (hereinafter Bchl-D) were shown to selectively ablate localized solid tumors in different targets (WO 00/33833; WO 2004/045492). In particular, VTP with the Bchl-D designated WST11, after successful clinical trials (Azzouzi et al., 2013, 2017; Eymerit-Morin et al., 2013), has been recently approved for use in early stage prostate cancer treatment.

Metronomic chemotherapy, which was originally designed to inhibit angiogenesis, involves low-dose chemotherapeutic agents administered in a frequent regular schedule with no prolonged breaks and minimizes severe toxicities (Ge et al., 2012; Ghiringhelli et al., 2007). Such treatments were found to particularly impact pro tumor immune cells proliferation in a specific cell population manner.

SUMMARY OF THE INVENTION

In one aspect, the present invention provides an anti-myeloid-derived suppressor cells agent (hereinafter "anti-MDSCs agent") and a bacteriochlorophyll derivative (hereinafter "Bchl-D) for use in combination therapy for cancer, wherein the anti-MDSC agent and the Bchl-D are administered sequentially and the administration of the Bchl-D is followed by photodynamic therapy (PDT).

In another aspect, the present invention provides a method for treatment of cancer by combination therapy comprising administering to a patient in need thereof: (i) a therapeutically effective amount of an anti-myeloid-derived suppressor cells (MDSCs) agent (hereinafter "anti-MDSCs agent"); and (ii) a therapeutically effective amount of a bacteriochlorophyll derivative (Bchl-D) followed by photodynamic therapy (PDT) (hereinafter "Bchl-D PDT").

BRIEF DESCRIPTION OF THE DRAWINGS

The patent or application file contains at least one drawing executed in color. Copies of this patent or patent application publication with color drawings will be provided by the United States Patent and Trademark Office upon request and payment of the necessary fee.

FIG. 1A shows in-vivo accumulation and clearance of STL-6014 (upper row) and STL-7012 (lower row) in mice bearing 4T1 breast tumor.

FIG. 3 shows the percentage of animals free of orthotopic 4T1 tumors at day 7 (blank) and day 30 (black) post one of five treatment regimens. STL-6014 PDT treatment was applied at day 7 post 4T1 grafting in the mammary pad and Gemzar (GEM) administration followed treatment Scheme 1 depicted in FIG. 2. The following regimens were applied: (1) no treatment (Control, N=18); (2) STL-6014 PDT (PDT, N=29); (3) metronomic Gemzar (GEM, N=11) started at 5 days days post grafting; (4) metronomic Gemzar started at day 1 post STL-6014 PDT (N=19) PDT is applied at 6 h post STL-6014 injection); and (5) metronomic Gemzar started at day 2 prior to STL-6014 PDT (N=20, PDT 6 h post STL-6014 injection).

FIG. 20 shows Foxp3 positive cells (Treg cells) infiltration to 4T1-luc tumors. 4T1 tumors grafted at the hind leg of Balb/C mice were excised when reaching 30-60 mm$^3$ at indicated times post CTX or saline administration, formalin-fixed and paraffin embedded. Sections were prepared and stained for Foxp3 expression. Number of positive cells was measured using Fiji software.

FIG. 21 shows the effect of low dose CTX administration at 3 days prior WST11 VTP on T cell populations in draining lymph nodes and spleens of mice bearing 4T1-luc tumors.

FIG. 23C presents percentage of mice bearing 4T1 tumors in their mammary pad that were completely cured (blank), cured of primary tumor but developed metastases (dashed) and animals presented both recurrence of primary tumors and development of metastases (black) at day 90 after different treatment regimens.

DETAILED DESCRIPTION OF THE INVENTION

Figure 1B:
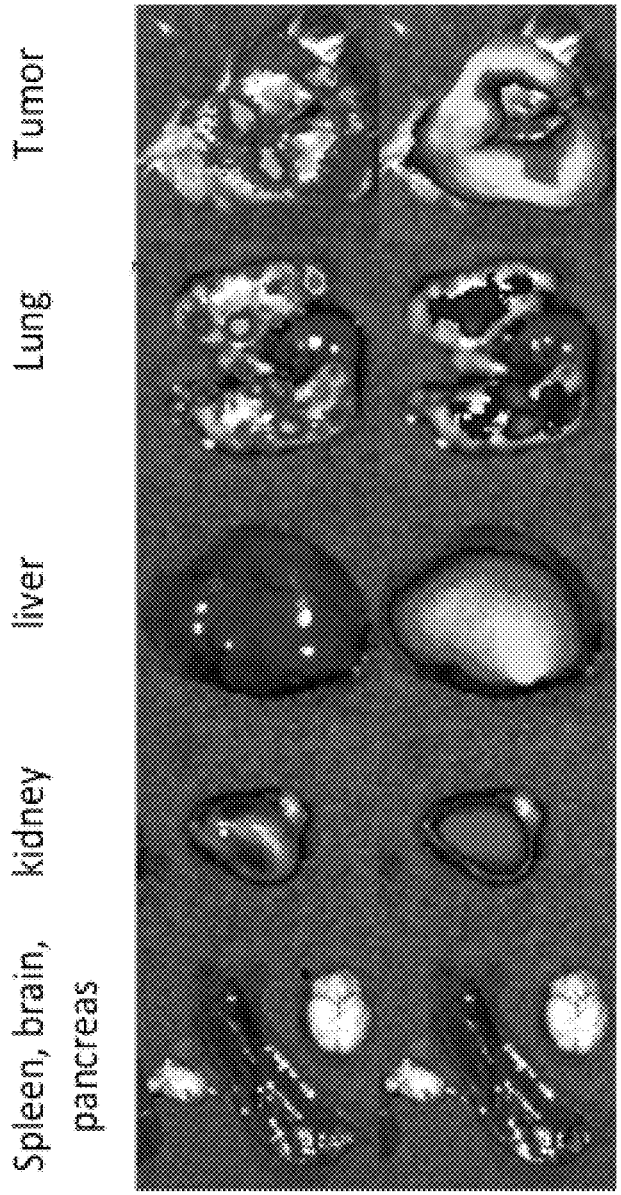
FIG. 1B shows the accumulation and/or retention of STL-6014 in tumor and different organs at 16 h post administration.

In certain embodiments, the invention relates to combinational therapies using bacteriochlorophyll-based photodynamic therapy (PDT) or vascular-targeted PDT (VTP) and immune cells, particularly myeloid-derived suppressor cells (MDSCs), modulating agents for the elimination of primary tumors and prevention of cancer dissemination.

It was found in accordance with the present invention that by using different derivatives of bacteriochlorophyll found effective in primary tumor ablation in combination with agents found to have anti-MDSCs activity, primary tumor ablation is achieved accompanied by prevention of metastatic tumor progression most probably via annihilation of remote micrometastases.

In certain embodiments, the present invention is directed to the non-thermal ablation of localized solid tumors and elimination of their remote micrometastases.

In one aspect, the present invention provides an anti-myeloid-derived suppressor cells agent (hereinafter "anti-MDSCs agent") and a bacteriochlorophyll derivative (hereinafter "Bchl-D") for use in combination therapy for cancer, wherein the anti-MDSC agent and the Bchl-D are administered sequentially and the administration of the Bchl-D is followed by photodynamic therapy (PDT).

The combination therapy of the invention has enhanced therapeutic effect compared to the effect of the anti-MDSCs agent or of the Bchl-D followed by PDT, when each is administered alone. In certain embodiments, this enhanced therapeutic effect is a synergistic therapeutic effect, namely, much stronger than the additive therapeutic effects of the individual treatment modalities.

The anti-MDSCs agent for use according to the invention may be, without being limited to, gemcitabine, 5-fluorouracyl (5-FU), cisplatin, paclitaxel, cyclophosphamide (CTX, CY), sunitinib, a cyclooxygenase 2 (COX-2) inhibitor such as SC-58236 and SC-58125, a bisphosphonate such as zoledronic acid or an aminobisphosphonate such as alendronate, all-trans retinoic acid (ATRA), vitamin D3, vitamin A, a KIT-specific antibody, a nitroaspirin derivative, a synthetic triterpenoid derivative such as bardoxolone methyl (known as CDDO-Me), and a phosphodiesterase-5 (PDE-5) inhibitor such as sildenafil and taladafil.

In certain embodiments, the anti-MDSCs agent is gemcitabine or cyclophosphamide.

Any Bchl-D shown to cause ablation of tumors may be used according to the invention.

In certain embodiments, the Bchl-D for use according to the present invention is preferably a water-soluble anionic bacteriochlorophyll derivative optionally conjugated with an RGD-containing peptide or RGD-peptidomimetic residue.

In certain embodiments, the Bchl-D is an anionic Bchl-D of the formula I:

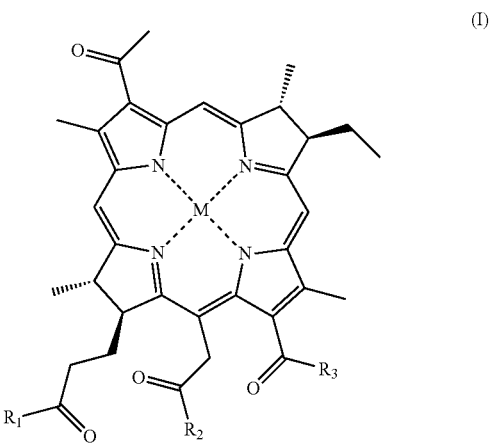

wherein
M represents 2H or Pd;
$R_1$ is $O-R_4$ or $-NHR_5$, wherein $R_4$ is H, $H^+$, an ammonium group or a monovalent metal cation such as $Na^+$ or $K^+$, and $R_5$ is an RGD-containing peptide or RGD peptidomimetic residue;
$R_2$ is $-O-C_1-C_6$ alkyl, preferably methyl;
$R_3$ is $-NH-(CH_2)_n-SO_3^-R_6^+$, wherein n is 2 or 3 and $R_6^+$ is a monovalent metal cation such as $Na^+$ or $K^+$; and
pharmaceutically acceptable salts and optical isomers thereof.

In certain embodiments, the anionic Bchl-D for use in the invention has the formula I wherein $R_1$ at position $17^3$ is $OR_4$, namely, it is not conjugated to an RGD-containing peptide or RGD peptidomimetic residue (hereinafter "non-conjugated Bchl-D") such as, but not limited to, the Bchl-Ds herein designated WST11 and STL-7012.

WST11, the rhodobacteriochlorin derivative Palladium $3^1$-oxo-15-methoxycarbonylmethyl-rhodobacteriochlorin $13^1$-(2-sulfoethyl) amide dipotassium salt, was synthesized in the laboratory of Prof. Avigdor Scherz, a co-inventor in the present application, at the Weizmann Institute of Sciences (Rehovot, Israel) and disclosed in WO 2004/045492. After successful clinical trials, WST11 has been recently approved for use in early stage prostate cancer treatment.

STL-7012 is the non-metalated Bchl-D $3^1$-oxo-15-methoxycarbonylmethyl-Rhodobacteriochlorin $13^1$-(2-sulfoethyl) amide dipotassium salt (disclosed in WO 2008/023378, formula in Appendix hereinafter).

Other anionic Bchl-Ds that can be used according to the invention include the following compounds disclosed in WO 2004/045492: Palladium $3^1$-oxo-15-methoxycarbonylmethyl-rhodobacteriochlorin $13^1$-(3-sulfopropyl) amide dipotassium salt; $3^1$-oxo-15-methoxycarbonylmethyl-rhodobacteriochlorin $13^1$-(2-sulfoethyl) amide dipotassium salt; $3^1$-oxo-15-methoxycarbonylmethyl-rhodobacteriochlorin $13^1$-(3-sulfopropyl) amide dipotassium salt; and Palladium $3^1$-oxo-15-methoxycarbonylmethyl-rhodobacteriochlorin $13^1$-(2-sulfoethyl) amide potassium salt.

When a non-conjugated Bchl-D is used in the invention, the PDT is vascular-targeted PDT (VTP) and an area of the local to be treated is illuminated at a short period after the administration of the non-conjugated Bchl-D is completed. This period is usually of 0-30 min, for example, 0, 10, 15, 20, 25 or 30 min.

In certain embodiments, the Bchl-D for use in the invention is a Bchl-D formula I conjugated to an RGD-containing peptide or RGD peptidomimetic residue has the formula I wherein $R_1$ at position $17^3$ is NH—$R_5$, namely, it is conjugated to an C(hereinafter "conjugated Bchl-D"). The RGD-containing peptide or RGD peptidomimetic residue may be a non-cyclic or cyclic peptide.

In certain preferred embodiments, the conjugated Bchl-D for use in the invention is conjugated to a cyclic RGD-containing peptide or RGD peptidomimetic residue. Examples of Bchl-Ds conjugated with cyclic RGD-containing peptide or RGD peptidomimetic residues for use in the present invention include, but are not limited to, those disclosed in the publications WO 2008/023378 and WO 2010/046900 such as the Bchl-Ds herein designated STL-6014, STL-6033, STL-6038, and STL-6068 (structures presented in Appendix hereinafter).

In certain preferred embodiments, the conjugated Bch-D is STL-6014, the $3^1$-oxo-15-methoxycarbonylmethyl-Rhodobacteriochlorin $13^1$-(2-sulfoethyl)amide-$17^3$-(cycloRGDfK) amide potassium salt disclosed in WO 2008/023378, wherein f indicates D-Phe.

Other conjugated Bchl-Ds disclosed in WO 2008/023378 that can be used according to the invention include, but are not limited to:

Palladium $3^1$-oxo-15-methoxycarbonylmethyl-Rhodobacteriochlorin $13^1$-(2-sulfoethyl)amide-$17^3$-(cycloRGDfK) amide potassium salt.

Palladium $3^1$-oxo-15-methoxycarbonylmethyl-Rhodobacteriochlorin $13^1$-(2-sulfoethyl)amide-$17^3$-(cycloRADfK) amide potassium salt.

25. Palladium $3^1$-oxo-15-methoxycarbonylmethyl-Rhodobacteriochlorin $13^1$-(2-sulfoethyl)amide-$17^3$-(cycloRGDf-N(Me)K)amide potassium salt.

When a conjugated Bchl-D is used according to the invention, the PDT is tissue-targeted and an area of the local for treatment is illuminated after some time, to allow accumulation and optimal concentration of the conjugated Bchl-D in the targeted tissue. This time may be of at least 4 h, preferably 6 h, after the administration of the conjugated Bchl-D is completed.

The anti-MDSC agent and the Bchl-D for use according to the invention are administered sequentially according to several different regimens. In general, in a session of treatment for ablation of a primary tumor or of a metastasis, the PDT or VTP treatment comprises a sole administration of the Bchl-D followed by illumination of an area of the local to be treated, and the anti-MDSC treatment comprises several administrations of the anti-MDSC agent at various determined time intervals. If necessary, the session may be repeated one or more times if and when a new metastasis is found later on.

In accordance with one regimen scheme, the anti-MDSC agent is administered once before the PDT or VTP treatment and several times thereafter at determined time intervals.

In accordance with another regimen scheme, the anti-MDSC agent is administered several times at determined time intervals after the PDT or VTP treatment.

In certain embodiments, the anti-MDSC treatment may comprise from 4 to 12 administrations or more of the anti-MDSC agent at determined time intervals of 5 to 12 days or more. For example, the anti-MDSC treatment may comprise 4, 5, 6, 7, 8, 9, 10, 11 or 12 or more administrations of the anti-MDSC agent at determined time intervals of 5, 6, 7, 8, 9, 10, 11 or 12 days or more.

It should be noted that these numbers are based on the animal experiments described herein and should not be limitative for the treatment of humans. According to the type of cancer being treated, the status of the patient's immune system and the patient's reaction to the treatment, the treatment protocol may be modified by the physician by changing the number of anti-MDSCs administrations and/or changing the number of days of the determined time interval between the anti-MDSCs administrations. For example, the physician may determine to make a pause in the treatment and provide during the treatment a longer interval than the determined interval and then reassume the original protocol after this break. For example, if the treatment protocol determined an interval of 5 days between the administrations of the anti-MDSC agent, the physician may decide to make a break of 10 to 20 days or more after the $2^{nd}$ or $3^{rd}$ administration, and then go back to the determined interval of 5 days for the following administrations. This break interval is always longer than the determined protocol interval.

In certain embodiments, the anti-MDSC agent is gemcitabine and PDT is performed with the Bchl-D STL-6014. 18. In other embodiments, the anti-MDSC agent is gemcitabine and VTP is performed with the Bchl-D WST11.

In certain other embodiments, the anti-MDSC agent is cyclophosphamide and VTP is performed with the Bchl-D WST11.

In accordance with certain embodiments of the invention, the anti-MDSC agent is administered in a low dose such as a dose 3 or 4 times lower than the conventional dose of the agent in conventional monochemotherapy. This is according to the concept of metronomic chemotherapy, which involves low-dose chemotherapeutic agents administered in a frequent regular schedule with no prolonged breaks and minimizes severe toxicities.

Several types of cancer can be treated according to the invention, both primary cancer solid tumors and metastases, including but not limited to, melanoma, renal cell carcinoma, colon, breast, lung, prostate, bladder, brain, adenocarcinoma of the pancreas or head and neck tumors.

The invention further relates to an anti-MDSC agent for use in combination therapy with a Bchl-D for the treatment of cancer, wherein the anti-MDSC agent and the Bchl-D are administered sequentially and administration of the Bchl-D is followed by photodynamic therapy (PDT).

The invention additionally relates to a Bchl-D for use in combination therapy with an anti-MDSC agent for the treatment of cancer, wherein the anti-MDSC agent and the Bchl-D are administered sequentially and administration of the Bchl-D is followed by photodynamic therapy (PDT).

In both cases, the combination therapy has enhanced therapeutic effect compared to the effect of the anti-MDSCs agent or the Bchl-D followed by PDT, when each of them is administered alone. This enhanced therapeutic effect may be a synergistic therapeutic effect.

In another aspect, the present invention provides a method for treatment of cancer by combination therapy comprising administering to a patient in need thereof: (i) a therapeutically effective amount of an anti-myeloid-derived suppressor cells (MDSCs) agent (hereinafter "anti-MDSCs agent"); and (ii) a therapeutically effective amount of a bacteriochlorophyll derivative (Bchl-D) followed by photodynamic therapy (PDT) (hereinafter "Bchl-D PDT").

In certain embodiments, the combination therapy of the method of the invention provides an enhanced therapeutic effect compared to the effect of the anti-MDSCs agent or the Bchl-D PDT, each administered alone. This enhanced effect may be a synergistic therapeutic effect.

In certain embodiments, the present invention synchronizes administration of chemotherapeutic agents that function as anti-MDSCs with cell/tissue-directed photodynamic therapy (PDT) or vascular-targeted photodynamic therapy (VTP) using different chemical derivatives of bacteriochlorophyll (Bchl-D). Low dose administration of the chemotherapeutic agent to the treated subject, several times at determined time intervals, achieves reduction in the MDSCs load. In certain embodiments, at a selected time interval after the first chemotherapeutic agent administration, PDT or VTP using Bchl-D is applied to ablate the primary tumors or observed metastases. With some agents, metronomic application (weekly application of low doses) continues for several weeks thereafter. Treatment efficacy is monitored by, but not limited to, follow up of primary tumor ablation using different imaging techniques (e.g. MRI, ultra-sound), histology (e.g. biopsies), reduction of MDSC counts in the circulation, delay or elimination of metastases growth and prolonged subjects survival. The treatment can be repeated later on in cases where new metastases are found in the patient.

In certain embodiments, the present invention provides a method of treating cancer, said method comprising administering to a patient in need thereof: (i) a therapeutically effective amount of an anti-myeloid-derived suppressor cells (MDSCs) agent (hereinafter "anti-MDSCs agent"); and (ii) a therapeutically effective amount of a bacteriochlorophyll derivative (Bchl-D) followed by photodynamic therapy (PDT) (hereinafter "Bchl-D PDT"), or vascular-targeted PDT (hereinafter "Bchl-D VTP") to provide a combination therapy having an enhanced therapeutic effect compared to the effect of the anti-MDSCs agent or the Bchl-D PDT each administered alone.

The terms "treating" and "treatment" or the phrase "to treat" as used herein refers to any type of treatment that imparts a benefit to a patient afflicted with a cancer, including improvement in the condition of the patient (e.g., in one or more symptoms), delay in the progression of the condition, prolongation of survival time, etc.

The term "therapeutically effective amount" as used herein for the anti-MDSCs agent refers to an amount that is therapeutically effective in the treatment of cancer as defined hereinabove when used in the combination therapy and administered in repeated doses according to the invention. The term "therapeutically effective amount" as used herein for the Bchl-D refers to its capability of causing ablation of the tumor or of the metastasis after performance of the PDT or VTP.

In case of tumor recurrence, e.g. in the form of new metastases, the immune modulated Bchl-D PDT or VTP can be repeated since new metastases may indicate the occurrence of new micrometastases of different clone compared with the primary tumor.

The studies described herein and in the figures show that the suggested combination of the two treatment modalities synergizes their impact, leading to primary tumor ablation accompanied by regression and elimination of micrometastases and subsequent metastases formation in 40-50% of animals presenting aggressive and metastatic cancers. These studies and the evolved protocols can be translated into the clinical arena in a straightforward manner.

The invention will now be illustrated by the following non-limitative Examples.

EXAMPLES

Materials and Methods
Materials
(i) Bacteriochlorophyll Derivatives—The Bchl derivatives and RGD-conjugates thereof were provided by Steba Biotech (Rehovot, Israel). STL-6014 was provided as the ammonium salt in a powder form converted to $K^+$ salt by dissolving the powder in DDW (1 mg/ml), the pH was adjusted to 8 by addition of KOH 1N, the resulted solution was frozen by liquid nitrogen and lyophilized to give STL-6014 $K^+$ salt. Working solution was prepared by dissolving STL-6014 $K^+$ salt in 5% mannitol solution (1 mg/ml), the pH of the solution was adjusted to 8 by addition of tris buffer (0.15%) in 5% mannitol, the solution was aliquoted to several tubes based on the experiment demands, frozen and lyophilized to give formulated STL-6014 $K^+$ salt. Concentration was verified by spectrophotometric measurement. STL-7012 was provided as dipotassium salt. Working solution was prepared by dissolving STL-7012 $K^+$ salt in 5% mannitol solution (1 mg/ml). Adjustment of pH, preparation of aliquots and verification of concentration were performed as for STL-6014. WST11 was supplied as a powder and kept in the dark at −20° C. Stock was prepared by dissolving WST11 in DDW containing 5% glucose and 0.67% mannitol, aliquoted and lyophilized. Working solution was reconstituted with DDW and the concentration of solution was confirmed spectrophotometrically. Alternatively, Clinical WST11 (batch: P00611, and 10-130611) was supplied as lyophilized formulation. Material was dissolved in 5% dextrose, aliquoted and stored at −20° C. At the day of treatment the aliquot was thawed, filtered and the concentration of solution was confirmed spectrophotometrically.

(ii) Chemotherapeutic drugs preparation and storage—Gemcitabine (GEM, Gemzar®, Lilly) was purchased from a local pharmacy as a powder, dissolved in saline to a concentration of 38 mg/ml, aliquoted and stored at −20° C. Aliquots were thawed, diluted with saline to a desired concentration and used on the same day at a dose of 75 mg/kg. Cyclophosphamide (CTX, Endoxan®, Baxter Oncology Gmbh, Germany) was purchased from a local pharmacy. A stock solution of 20 mg/ml was prepared by dissolving in 0.9% NaCl, aliquoted and stored at −20° C. Aliquots were thawed, diluted with saline if needed to a desired concentration and used on the same day prepared at indicated doses.

(iii) Murine cell lines—Mammary luciferase (luc)-labeled 4T1 cell line (4T1-Luc) was a kind gift from Dr. Zvi Granot (Faculty of Medicine, The Hebrew University of Jerusalem, Israel); melanoma B16-F10 cell line was obtained from the American Type Culture Collection (ATCC, Manassas, Va.); bladder MB49 cell line was a kind gift from James Allison (MSKCC, New York, USA), and luc-labeled MB49-cell line was established using the murine stem cell virus (MSCV)-puromycin-luc-GFP construct (kindly provided by Dr. Emily Cheng, Human Oncology and Pathogenesis Program, MSKCC). 4T1 and MB49 cells were maintained in DMEM medium and B16-F10 cells in RPMI medium supplemented with 1 mmol/L sodium pyruvate, 10% fetal calf serum (FCS), 250 µg/ml hygromycin, 0.06 mg/ml penicillin and 0.1 mg/ml streptomycin. The cells were grown as monolayer at 37° C. in a humidified atmosphere (5% $CO_2$, 95% air).

(iv) Murine tumor models—Female, Balb/c mice (6-8 week old) were grafted either subcutaneously (s.c.) into the right hind leg or orthotopically with $1\times10^6$ 4T1 cells suspended in 50 or 1000 PBS. For the rechallenge study, $2\times10^5$ 4T1 cells were orthotopically grafted. For bladder cancer model, $5\times10^4$ of MB49 or MB49-luciferase cell line were s.c. injected into the right flank of C57B/6 male mice (7-8 weeks old, Taconic, Hudson, N.Y.) 15 days prior to VTP treatment. For the efficacy study of VTP in immune compromised mice, the same number of MB49 cells was injected in the flank of $Rag^{-/-}$ on C57B/6 background or C57B/6 male mice (7-8 week old, Jackson Laboratory, Bar Harbor, Me.). For bilateral model of MB49 cells, animals received $5\times10^4$ MB49 cells in the right flank and $5\times10^4$ cells in the left flank on days $-15$ and $+1$, respectively. All experimental procedures were approved by the Institutional Animal Care and Use Committee at the Weizmann Institute of Science (Rehovot, Israel) and The Memorial Sloan Kettering Cancer Center (MSKCC, New York, USA).

Methods (v) Whole-body fluorescence imaging (PDT studies): Following intravenous (i.v.) injection of 7.5 mg/kg STL-6014 or STL-7012, whole body near infra-red fluorescence images of tumor tissues and normal organs were recorded using the In Vivo Optical Imaging System (IVIS®Spectrum, Caliper LifeScience., Alameda, Calif.) with 847/875 nm filters for excitation and emission, respectively, at an integration time of 1 seconds. Whole body imaging of luciferase-transfected tumors and metastases were recorded five minutes following 75 mg $Kg^{-1}$ intraperitoneal (i.p.) injection of D-luciferin with respective filter sets.

(vi) PDT treatment protocol: 4T1-Luc cells were grafted in the mammary pad of Balb/c mice. When primary tumors reached $\sim50$ $mm^3$, mice were i.v. injected with 7.5 mg/kg STL-6014 and left under dim light conditions for 6 h, after which an area of 1 $cm^2$ including the tumor was illuminated with a 753 nm laser, applied through frontal face optical fibers (Medlight SA, Switzerland) at 200 $mW/cm^2$. During the first two post-treatment days, the mice received analgesia (2.5 mg/kg Flunexin, once daily). Ablation of primary tumors was assessed every 7 days by imaging the tumor's luciferase-mediated bioluminescence signal, using IVIS. Mice were sacrificed (according to the guidelines of the Weizmann Institute of Science) when tumors reached the diameter of 15 mm, or when the mouse developed metastases, determined by the IVIS whole-body fluorescence.

(vii) VTP treatment protocol: For s.c. tumor treatment: Tumor-bearing mice were anesthetized by i.p. injection of a mixture of Ketamine/Xylazine solution 100 mg/10 mg per kg body weight, respectively. WST11 was then administered at a dose of 9 mg/kg by 5 min constant rate i.v. infusion into the tail vein. Illumination at fluency rate of 100 or 150 $mW/cm^2$ for 10 min was initiated immediately after infusion completion using a 4 W, 755 nm diode laser (Ceramoptec, Germany) equipped with frontal optical diffuser. Mouse was placed on the left side to expose the tumor and covered with non-transparent material to protect normal tissues. For mammary tumor treatment: Mice were anesthetized as before. WST11 dose was 9 mg/kg given by 5 min infusion. Mouse was placed on the back, the tumor was lifted with a clip to separate it from the body and the animal was shielded with black material to prevent vital organ damage. Illumination at fluency rate of 200 $mW/cm^2$ for 15 min was initiated immediately after infusion completion using a 4 W, 755 nm diode laser (Modulight, Finland) equipped with frontal optical diffuser.

(viii) Combination therapy comprising PDT in tandem with low-dose Gemzar™ (GEM): Six days after 4T1-luc cell grafting (when primary tumors reached $\sim50$ $mm^3$), mice were i.v. injected with 7.5 mg/kg STL-6014. Six hours following drug administration tumor was illuminated at 753 nm (200 $mW/cm^2$) for 15 min. Two protocols for GEM co-treatment were applied: (1) 75 mg/kg GEM (dissolved in 100 µl saline) administered i.p. 2 days before PDT, one day after and every 5 days thereafter, until day 33, or (2) 75 mg/kg GEM dose, administered one day after PDT and every 5 days thereafter until day 33. Metastases progression/regression was followed up for 120 days by whole-body imaging of the luciferase bioluminescence.

(ix) Combination therapy comprising VTP and low-dose GEM: GEM was administered i.p. at a dose of 75 mg/kg. Treatment regimens used were as follows: (i) starting on day ($-1$) with three subsequent doses on days 1, 6 and 11 post VTP; (ii) starting on day ($-2$) with three doses on days 3, 8 and 13. Alternatively, 50 mg/kg on clinical schedule of 3 week cycle, $3^{rd}$ week off or at 120 mg/kg on BIW (twice a week) schedule as indicated per each experiment, starting the first dose at 3 days prior to VTP treatment.

(x) Combination therapy comprising VTP and cyclophosphamide (CTX): For s.c. tumor treatment, CTX was administered i.p. at a single dose of 150 mg/kg or 50 mg/kg (for the latter stock solution was freshly diluted 1:3 with 0.9% NaCl to keep volume range) three days before VTP. Control groups received 0.9% NaCl. For mammary tumors treatment, 50 mg/kg was administered according to the following regimens: (i) starting on day ($-1$) with three subsequent doses on days 1, 6 and 11 post VTP; (ii) starting on day ($-3$) with three doses on days 3, 10 and 17.

(xi) In vivo follow-up of VTP outcome on primary tumor and lung metastases: Local tumor response was assessed by bioluminescence imaging (BLI) and caliper measurements. Tumor volume was calculated as previously published (Preise et al, 2003). For BLI assessment, tumor-bearing mice were anesthetized and i.p. injected with luciferin (1.2 µg/mouse, Regis, USA). Mice were then placed in a Xenogen IVIS Spectrum Imaging System (Caliper LifeSciences, MA, USA) and images were acquired for 60 sec following $\sim10$ min accumulation. For s.c. tumors, mice were placed on a side for primary tumor imaging and then on the back for metastases assessment. Supine position was used to allow both primary tumor and lung metastases imaging in mammary model. Early termination was done when primary tumor burden was above 15 mm in a large diameter or when metastases were detected, to prevent animal suffering and death.

(xii) Histology: Mice were sacrificed according to the guidelines of the Institutional Animal Care and Use Committee of the Weizmann Institute of Science (IACUC, Rehovot, Israel). Tissues were removed and fixed in 4%/10% buffered formalin for 48 h. Samples were then embedded in paraffin, sliced and stained for hematoxylin and eosin (H&E) at histology unit according to standard procedure. Immunostaining for Foxp3, CD4, CD8, CD11b and Ki67 antibodies was performed at Memorial Sloan Kettering by automated procedure.

(xiii) Ly6G staining (PDT studies): Mice bearing orthotopic 4T1-Luc tumors at two sites (right and left mammary fat pad) were subjected to PDT only on one side, combined with the second GEM treatment protocol. Tumors were excised 24 h, 3 days and 3 weeks post-PDT, and fixed and stained for Ly6G. Images were acquired for off-line analysis using a slide scanner.

(xiv) Flow cytometry (FACS analysis): Spleens were excised from humanly sacrificed animals and strained through 70 µm mesh. Red blood cells were lysed with ammonium chloride lysis solution (ACK) and cells counted and adjusted for staining. Lymph nodes were minced in PBS, washed and adjusted for staining. Tumors were cut to small pieces and incubated for 30 min at 37° C. with shaking in the mixture of 2.5 mg Collagenase II, 2.5 mg Collagenase IV and 0.5 mg DNAase per 1 ml 1% BSA containing PBS. Cell suspension (tumor or spleen) was pressed through 70 µm filters, washed twice with FACS buffer and incubated (if indicated) for 30 min on ice with fixable viability dye eFluor 450, (eBioscience, San Diego, Calif.) diluted in PBS (1:1000). $1-5\times10^6$ cells were suspended in 1000 PBS and incubated for 15 min at 4° C. with rat anti-mouse CD16/CD32 (0.5 µg eBioscience, San Diego, Calif.) to prevent nonspecific antibody binding. According to the different experiments, cells were subsequently incubated for 30 min at RT with fluorescent antibodies including percp-cy5.5/APC-Cy7-CD11b, PE/PerCP-Cy5-Ly6G, PE-cy7-Ly6C, APC-F4/80, Alexa488/PE-CD11c, eVolve655/v450-MHCII, percp-cy5.5-CD3, APC/v450-CD4, Alexa488-CD8, PE-cy7-Foxp3, CD4-APC, Alexa488/PerCP-Cy5/PE-Texas Red-CD8 and PE/APC-Foxp3, Alexa 700/FITC-CD45, FITC-Ki67, APC-Cy7-CD25, PE Texas Red-Granzyme B, PE-CD62L, PE-Cy7-CD44, and APC-CD86 (the antibodies were purchased from eBioScience (San Diego, Calif. and from BioLegend, San Diego, Calif.). Data acquisition was performed using customized LSRII flow cytometer (BD Bioscience, San Jose, Calif.) and analyzed using FlowJo software (Tree Star, Ashland, Oreg.).

(xv) Metastatic cells isolation and colony forming assay: Mice were implanted with 4T1-luc cells. Seven days later lungs were isolated from anesthetized mice following perfusion with sterile ice cold PBS. Following excision mice were euthanized. Lungs were minced in PBS, washed and strained through 100 µm mesh. The tissue was then digested with 5 mg/ml collagenase A for 45 min in 37° C., washed and re-suspended in worm complete medium. The suspension was passed through 70 µm and plated in tissue culture incubator. Following seven days, propagation in culture bioluminescence was detected using IVIS Imaging System after addition of luciferin.

(xvi) Statistical analysis: Data were analyzed by two-tailed Student's unpaired t-test in Microsoft Excel or in two-way ANOVA test (GraphPad, San Diego, Calif., USA). p-values of less than 0.05 were considered statistically significant. Survival curves were compared using a log-rank test (GraphPad Prism 6, San Diego, Calif., USA).

Example 1

Pharmacokinetics and Uptake of STL-6014 by Primary Tumor and Metastases in 4T1 Tumor Bearing Mice In a preliminary experiment, female Balb/c mice bearing orthotopic 4T1-Luc breast tumors were intravenously injected with STL-6014 (7.5 mg/kg) or STL-7012 (9.5 mg/kg). Near infrared (NIR) fluorescence images demonstrated STL-6014 selective accumulation in the tumor (FIG. 1A, upper row). The tumor became evident ~2 hr after administration, yet fairly strong signals were observed in the clearance organs (e.g., bladder). On the day after administration, STL-6014 had markedly accumulated in the tumor (FIG. 1B, upper row), relative to the surrounding tissues, with considerably lower levels in the abdominal clearance organs. STL-7012 did not accumulate in the tumor (FIG. 1A, lower panel) and cleared through the liver within a few hours of injection (FIG. 1A, lower panel). The same was true for WST11 (Data not shown). Accumulation in tumor and lung metastases, accompanied by accumulation in clearance organs is demonstrated in FIG. 1B. Upper panel-bioluminescence of different tissues in the tumor-bearing mice; lower panel-fluorescence of STL-6014 in these organs.

Example 2

Treatment of 4T1 Bearing Animals with STL-6014 and Gemzar According to Scheme 1

Figure 2A:
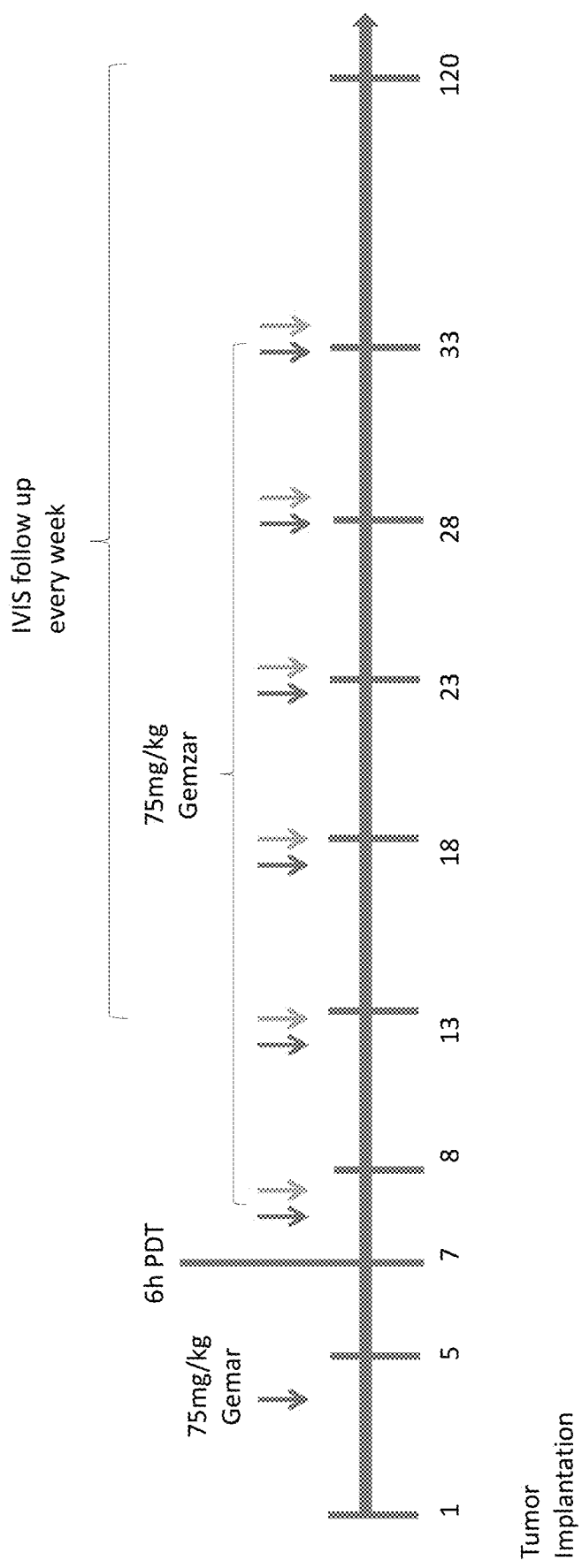
FIG. 2 shows: (2A) The treatment Scheme 1 of mice bearing 4T1 tumors in their mammary pad using a combination of STL-6014 PDT and Gemzar administration starting either at two days prior PDT (blue arrows) or one day after PDT (orange arrows); (2B) Illuminated tumors at 6 h post-bolus injection of STL-6014; (2C) Luciferin bioluminescence of mice with primary and metastatic tumor (left), primary tumor only (middle) and cured mice (right).
Figure 2C:
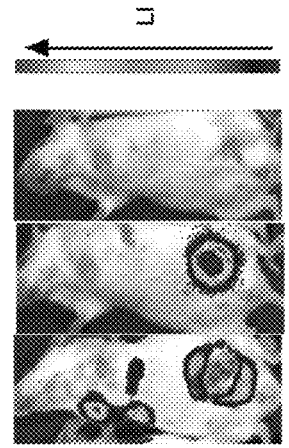
Figure 2B:
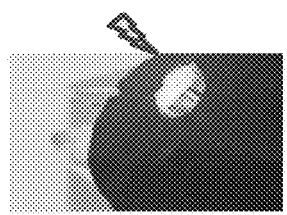

Balb/c mice were inoculated with $1\times10^6$ 4T1-Luc cells in the mammary fat pad. At day 7 post grafting, when tumors reached 5-7 mm diameter, mice bearing 4T1-Luc could be subjected to one of several treatment options as described by treatment scheme 1 (FIG. 2A) as follows:

(i) In using photodynamic therapy (PDT) as the only treatment modality, animals were i.v. bolus injected (3 min) with 7.5 mg/kg STL-6014. At 6 h post injection, the tumor was illuminated by 753 nm at 200 mW/cm$^2$ (Modulight Inc., Finland) for 10 min.

(ii) In using gemcitabine (Gemzar) as the only treatment approach, tumor bearing animals were ip administered with 75 mg/kg Gemzar starting either at day 5 (blue) or day 8 (orange) post tumor grafting and then 6 more times at 5 days intervals as described in treatment Scheme 1.

(iii) In the combined treatment approach, animals were either (a) i.p. administered 75 mg/kg Gemzar at day 5 followed by STL-6014 PDT at day 7 and 6 more times of Gemzar administration; or (b) by STL-6014 PDT at day 7, then by Gemzar at day 8 followed by 6 more times of Gemzar administration. Tumor progression and dissemination was monitored once a week till day 120 or until animal termination because of tumor burden using the bioluminescence signal of luciferin recorded by IVIS (Oxygen).

Example 3

Response of Primary Tumors in 4T1 Bearing Animals to Treatment with STL-6014 PDT and Gemzar Balb/c bearing 4T1 tumor were divided in 5 groups: (1) non-treated (control); (2) treatment with STL-6014 PDT; (3) treatment with metronomic Gemzar: (4) treatment with STL-6014 PDT and metronomic Gemzar starting 1 day post PDT; and (5) treatment with STL-6014 PDT and metronomic Gemzar starting 2 days prior to PDT. FIG. 3 shows primary tumor responses at day 7 (white) and 30 (black) post STL-6014 PDT alone or in combination with Gemzar provided in one of the two treatment modalities described in treatment Scheme 1. Absence of primary tumor was observed in 70-80% of mice treated by STL-6014 PDT alone or in combination with Gemzar at day 7 post treatment. However, at day 30 post treatment, 82% of animals treated by STL-6014 PDT alone had primary tumor regrowth compared with only 30-40% in the combined STL-6014 PDT+

Gemzar treatment. None of the control animals (no treatment or treatment by Gemzar only) showed primary cure (0%).

Example 4

Survival of 4T1 Tumor Bearing Mice to STL-6014 PDT and Gemzar Treatments

Figure 4:
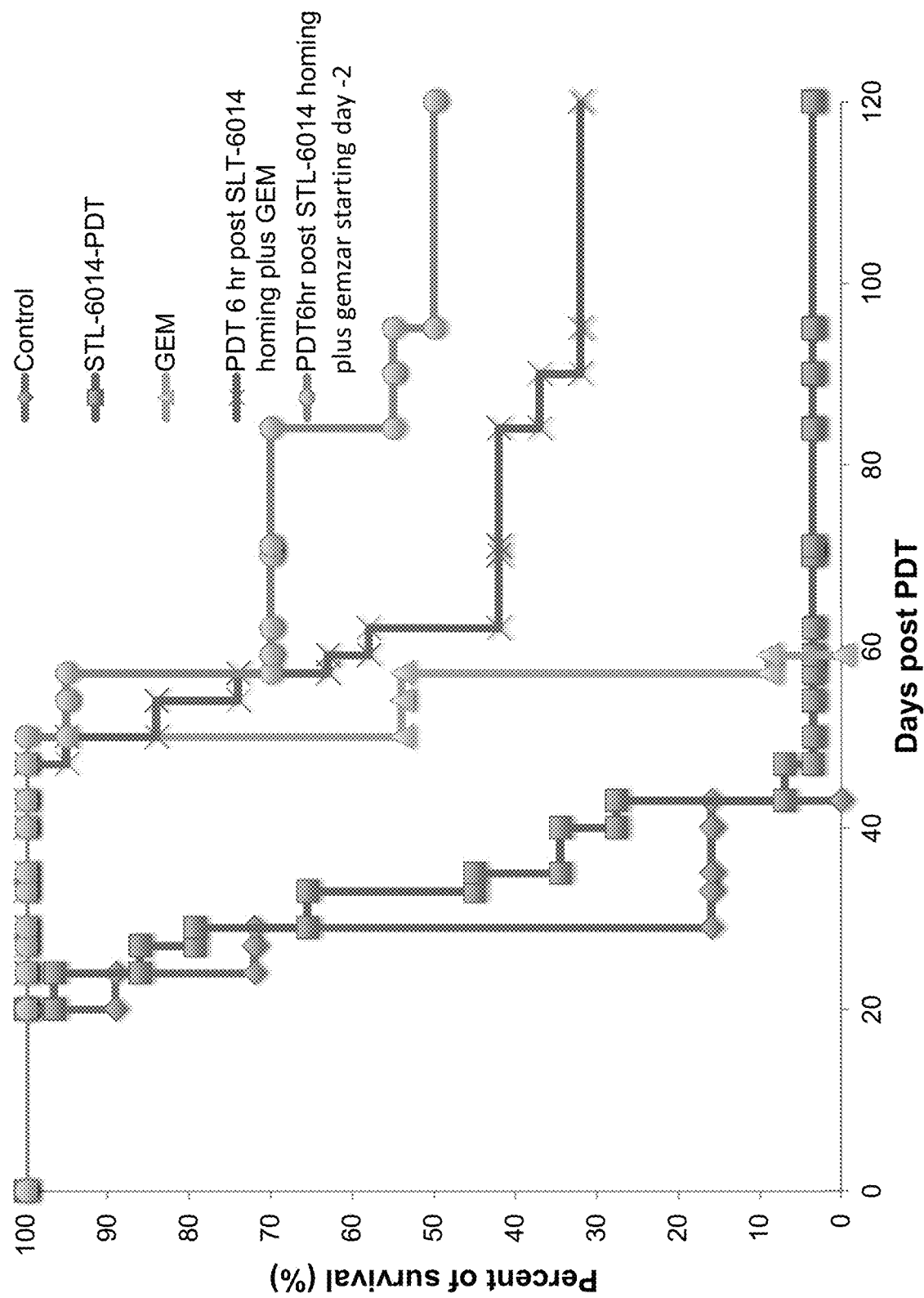
FIG. 4 presents Kaplan-Meier survival curves for Balb/C mice bearing orthotopic 4T1 tumors and treated by the different therapeutic regimens described in FIG. 3. Control (N=18) (♦)—no treatment; STL-6014 (N=29) (■)-STL-6014 PDT as monotherapy is applied at day 7 post tumor grafting as described in Materials and Methods; Gem (▲) (N=11)—1$^{st}$ Gemzar administration is applied as monotherapy at day 5 post tumor grafting; PDT 6 h plus GEM (N=19)—PDT is applied at 6 h post STL-6014 administration combined with Gemzar administration starting at 1 day post PDT and each week thereafter for 5 more weeks; PDT 6 h plus GEM starting −2 (N=20) (●)-PDT is applied at 6 h post STL-6014 administration combined with Gemzar administration for 5 times starting at day 2 before PDT and each week thereafter for five more weeks.

FIG. 4 shows the Kaplan-Meier survival curves over 120 days follow up of 4T1-Luc bearing mice subjected to different treatment regimens and controls. Treatment by STL-6014 PDT (N=29) did not show any significant survival difference compared to control mice (N=18). Extended mice survival was observed in the Gemzar-treated mice but no primary tumor cure (N=11). Thirty two percent of the 4T1 grafted animals survived after combined STL-6014 PDT and Gemzar given at one day post PDT (N=19), while 50% of the mice were cured (survived for 120 days) after Gemzar was given at 2 days before STL-6014 PDT (N=20).

Example 5

Response of Lung Micrometastases to STL-6014 PDT and Gemzar Treatment

Figure 5B:
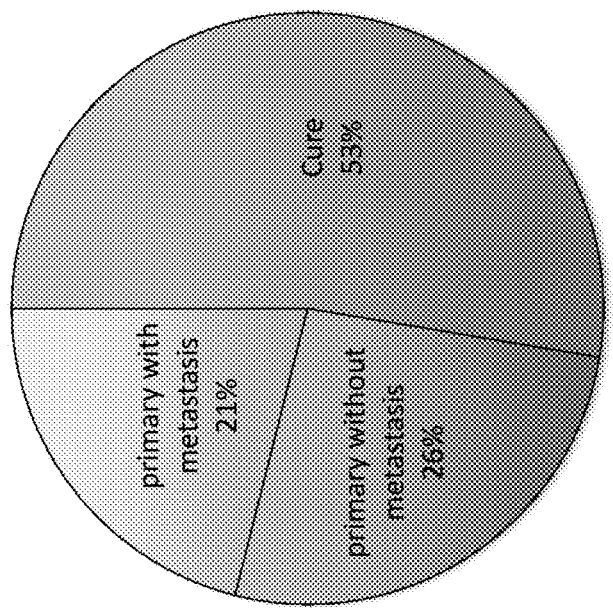
FIG. 5 depicts pie charts showing the percentage of animals found with 4T1 lung metastasis at the day of animals sacrifice following two different regimens of STL-6014 PDT combined with Gemzar. (5A) STL-6014-PDT is combined with Gemzar administration starting one day post STL-6014-PDT application (N=20). (5B) STL-6014-PDT is combined with Gemzar administration starting 2 days before STL-6014-PDT application (N=19).
Figure 5A:
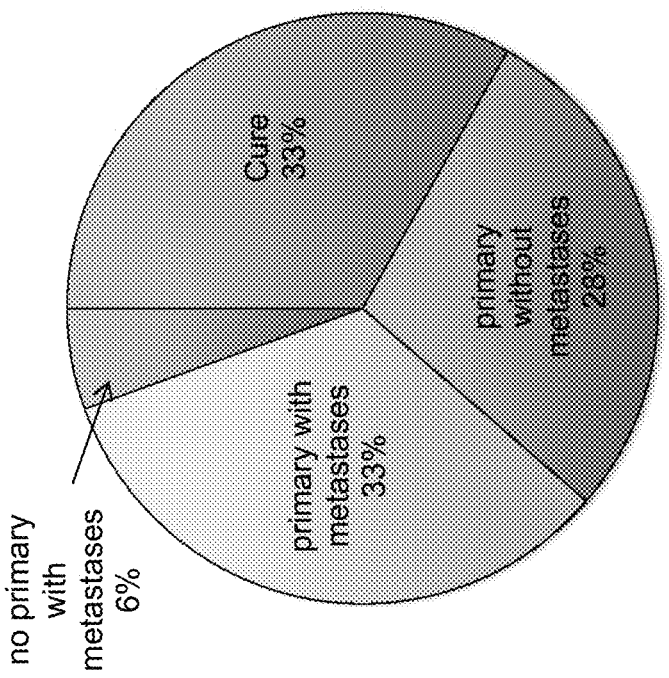

FIGS. 5A-B present two pie charts that show the percentage of animals presented with 4T1 lung metastasis following different treatment regimens by STL-6014 PDT combined with Gemzar at the day of animals sacrifice. Seventy nine percent of mice (N=20) receiving STL-6014 PDT combined with Gemzar administered 2 days prior to PDT were metastases-free (5B), while 61% (N=19) of animals treated by STL-6014 PDT with Gemzar given 1 day post-PDT were metastases-free (5A). This difference is statistically significant (p<0.01) demonstrating the possible advantage of Gemzar administration prior to PDT.

Example 6

Survival of 4T1 Bearing Mice Treated by STL-6014 PDT and Gemzar

Figure 6B:
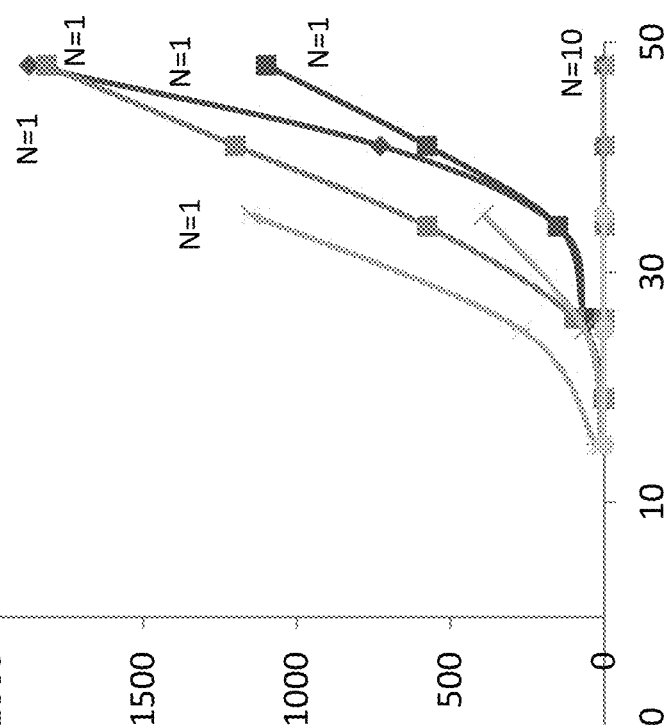
FIG. 6 illustrates 4T1 tumor progression in Balb/C mice that have been re-challenged by second orthotropic grafting of $2 \times 10^5$ 4T1 cells after being cured of 4T1 tumors by STL-6014 PDT combined with Gemzar given 2 days prior PDT. Re-challenge was performed at day 120 post first cure (240 days post first tumor grafting). (6A) Individual animal (N=10) survival post grafting of 4T1 tumors in naïve animals, each curve stands for one animal. (6B) Individual animal (N=15) survival post grafting of 4T1 tumors in animals that were treated and cured after first tumor grafting. Each curve stands for 1 animal except for the orange/green curve which stands for 10 animals. At day 50 post treatment these 10/15 animals had no primary and no metastatic tumor.
Figure 6A:
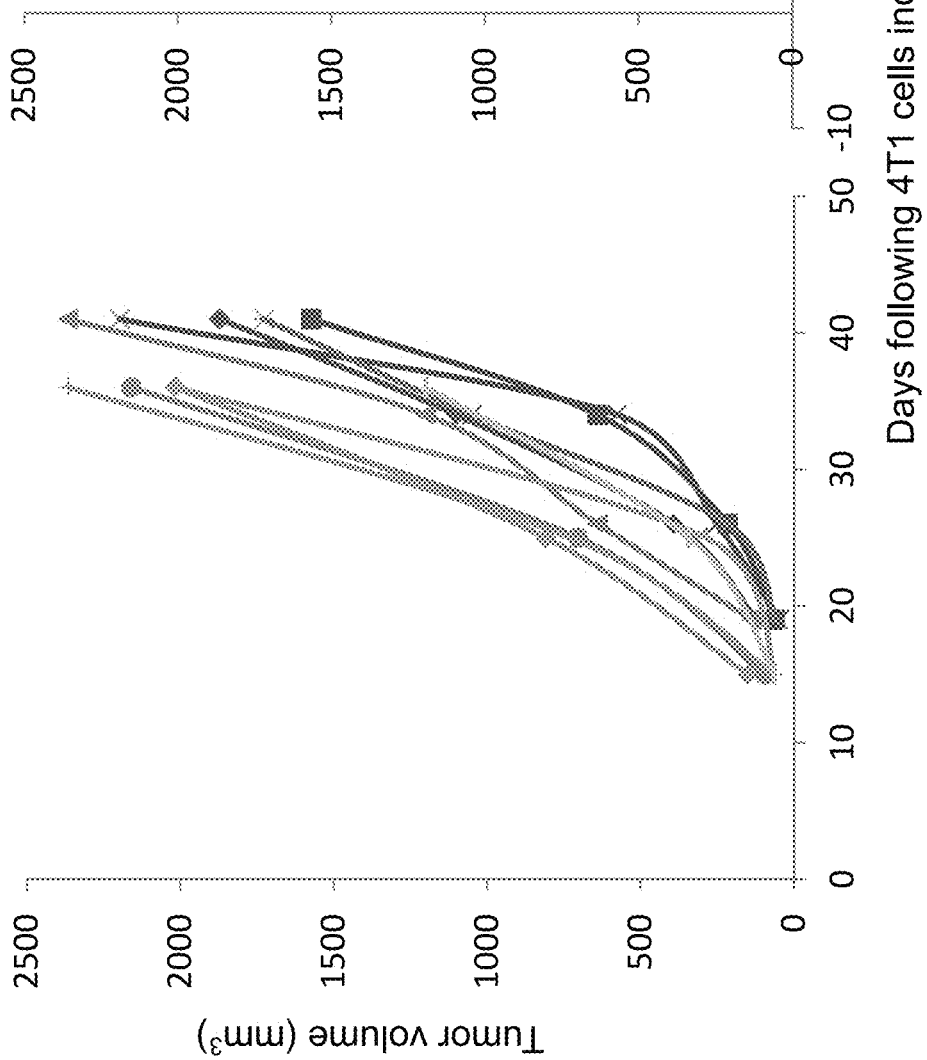

FIG. 6B shows the survival of individual animals re-challenged with a second grafting of 2×10$^5$ 4T1 cells at 120 days after they underwent complete cure from first grafted tumor as evident by the lack of 4T1 cell's bioluminescence at day 120 post first grafting. For comparison, FIG. 6A presents survival of naïve mice grafted by 2×10$^5$ 4T1 cells for the first time. Sixty seven percent of the animals rejected 4T1 tumor (Yellow-green curve, N=10) and 5 out of 15 presented delayed tumor growth, whereas 10 of 10 naïve mice challenged at the same time developed tumors. These findings demonstrate that combined PD/Gemzar treatment provides long term adaptive immunity to the treated animals.

Example 7

Figure 7:
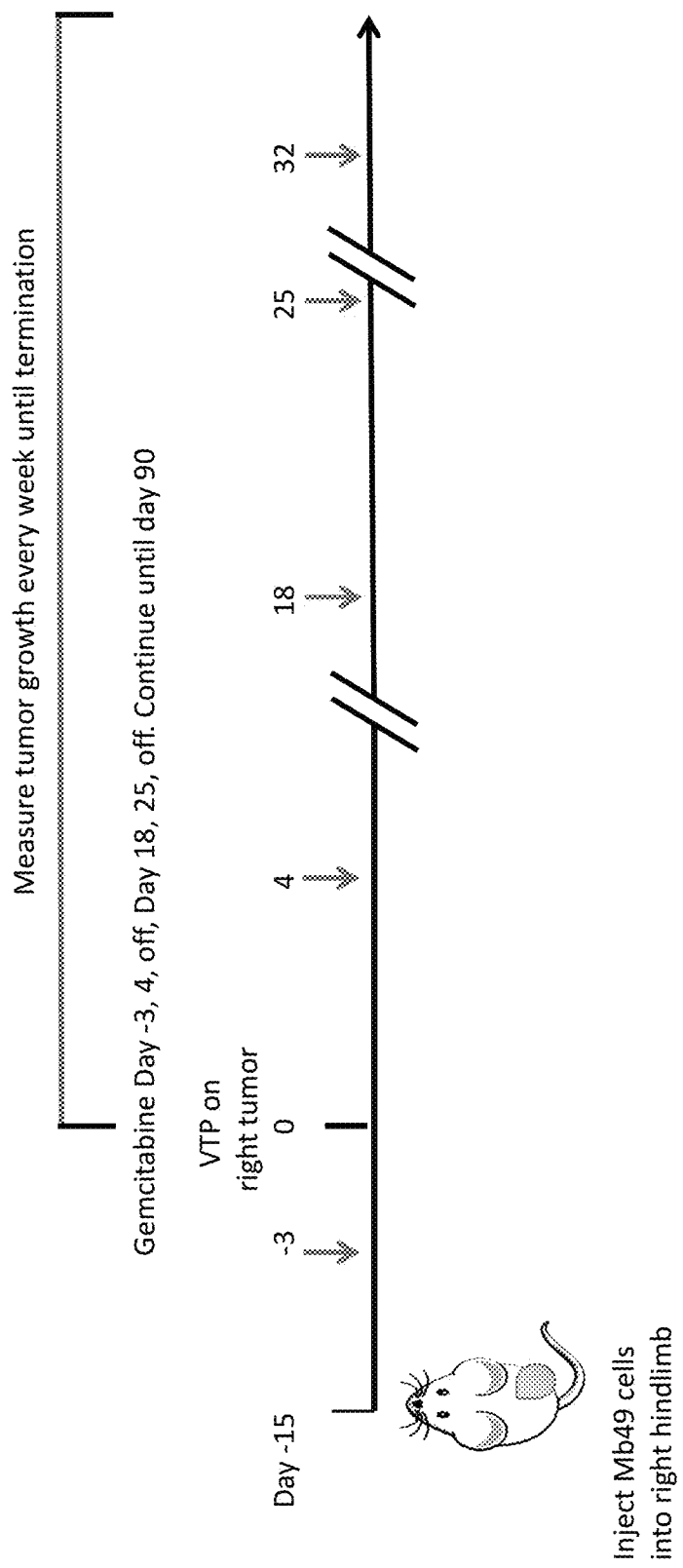
FIG. 7 depicts treatment Scheme 2 for combined WST11 VTP and Gemzar administration for mice bearing MB49 (bladder) tumors. MB49 cancer cells ($10^6$) were grafted on the hind leg of Balb/C mice at day −15. First Gemzar administration (50 mg/kg) was performed at day −3, then at day 4 and continued in cycles of 2 times/week, 3 weeks/month to a total of 12 treatments/90 days. WST11 VTP was performed at day 15 post tumor grafting. WST11 (9 mg/kg) was infused i.v. for 5 minutes followed by 10 minutes illumination at 753 nm using Modulight laser at 120 mW/cm$^2$.

Scheme 2 for Treatment of MB49 Mouse Madder Cancer Model with WST11 VTP and Gemzar FIG. 7 depicts a second treatment scheme applied herein to MB49 MB49 (mice bladder cancer) bearing Balb/C mice when tumor reached about 4-7 mm in diameter at day 15 of grafting 2×10$^5$ MB49 cells in the right hind leg. The treatment scheme comprises application of WST11 VTP alone, or ip administration of 50 mg/kg Gemzar at day 12 post grafting followed by 3 weeks cycles of Gemzar administration at day 1 and 7 of each week, followed by no administration at week 4 of each month. All together, animals received 12 Gemzar administrations. In the VTP treatment 9.0 mg/kg WST11 was I.V. infused for 5 minutes followed by 10 minutes illumination at 753 nm using Modulight laser at 120 mW/cm$^2$.

Example 8

Figure 8A:
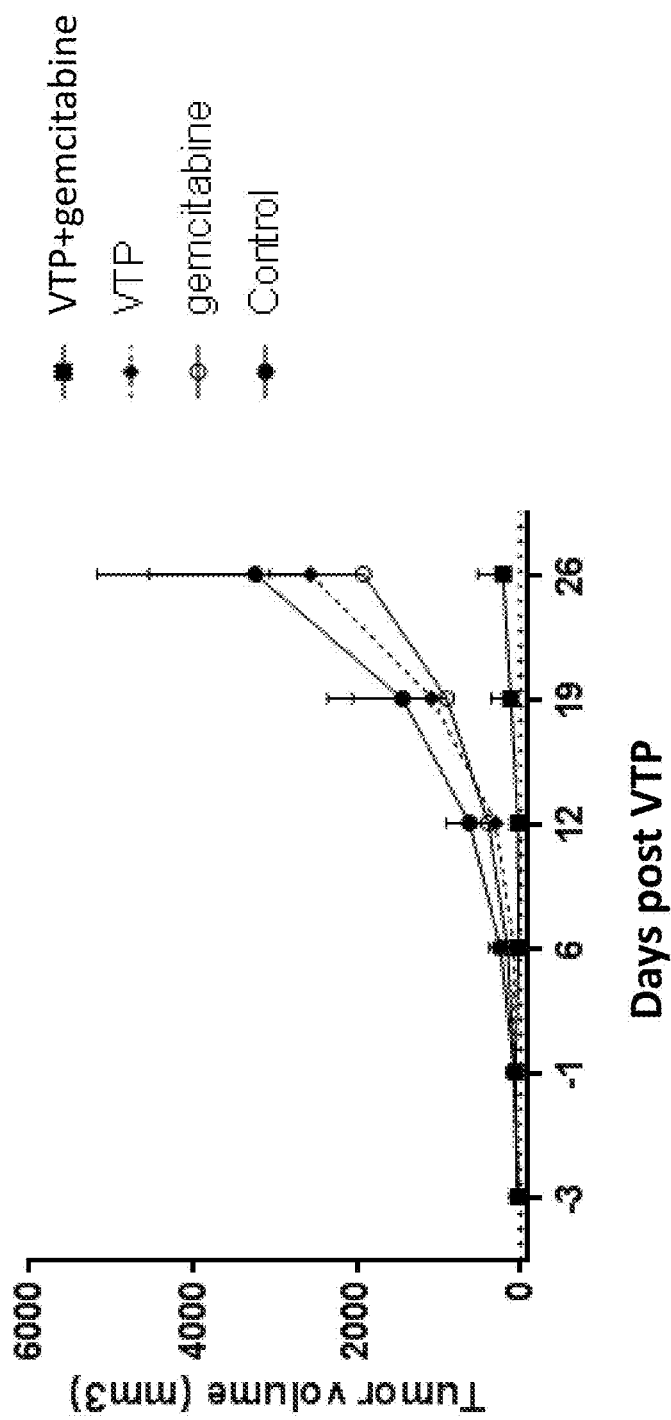
FIG. 8 shows the response of mice grafted with MB49 tumors to different treatment regimens based on treatment Scheme 2 (FIG. 7). (8A) Mean tumor growth (error bars—SEM). Black-control (0/17 cured, p<0.0001 vs VTP+Gemzar); Blue-Gemzar alone (0/19 cured, p<0.0001 vs VTP+Gemzar); Red-VTP alone (3/19 cured, p<0.0005 vs VTP+Gemzar); Green-VTP+Gemzar (11/17 cured). P value calculations are based on two way Anova test. (8B) Tumor growth in the hind leg of individual mice following the above WST11 VTP treatment combinations. Upper panel left-control, 0/17 cured; Upper panel right-Gemzar alone, 0/19 cured; Lower panel left-VTP alone, 3/19 cured; Lower panel right-VTP+Gemzar, 11/17 cured. (8C) Prevention of lung metastases as reflected in their bioluminescence at day 25 post treatment initiation: Upper panel—average radiance in the lungs of individual mice (*p<0.005, **p<0.0001); Lower panel upper row-images of control animals and animals treated by Gemzar alone; Lower panel lower row-Images of cured animals. (8D) Overall animal survival following the different treatment regimens.
Figure 8B:
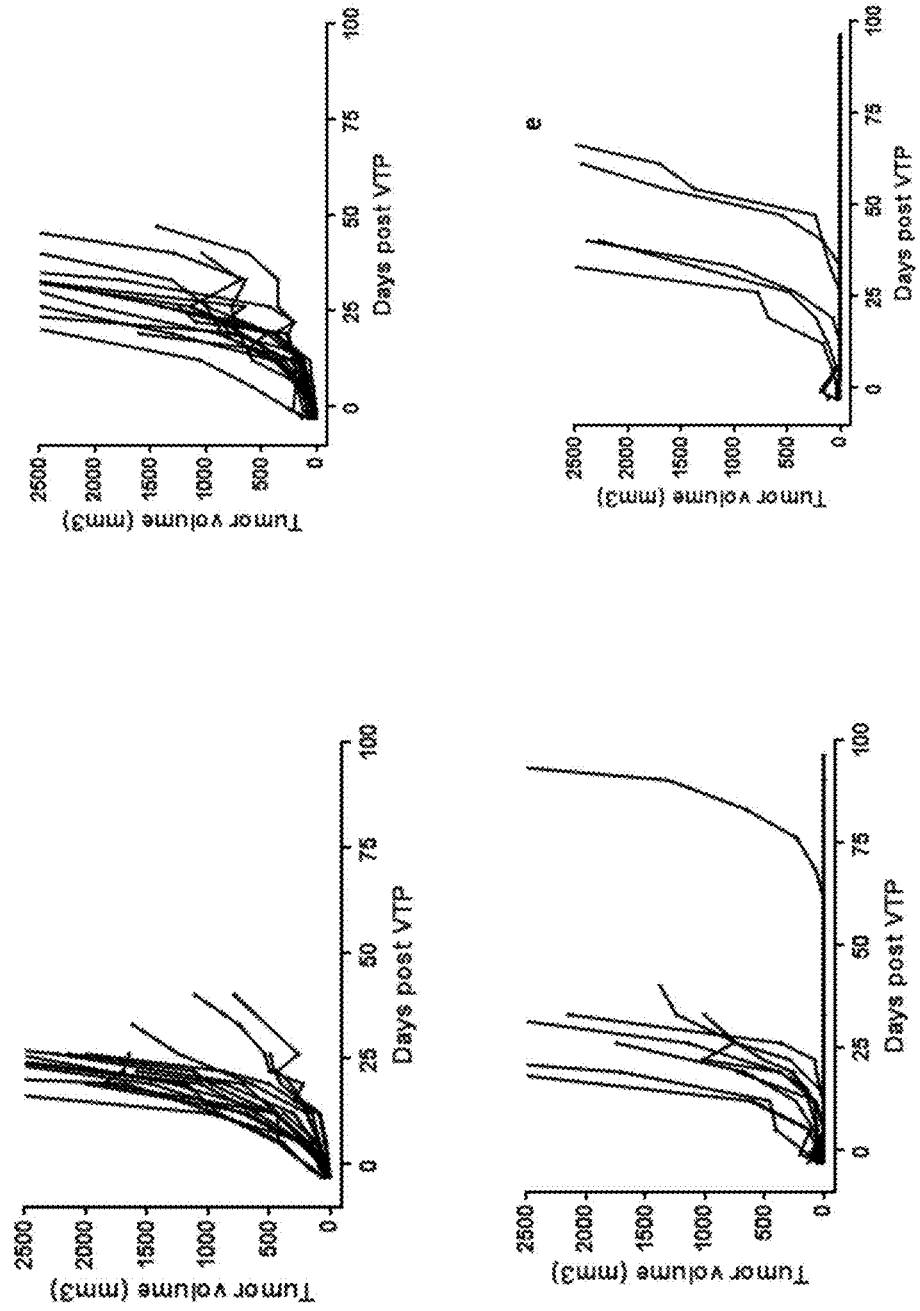
Figure 8D:
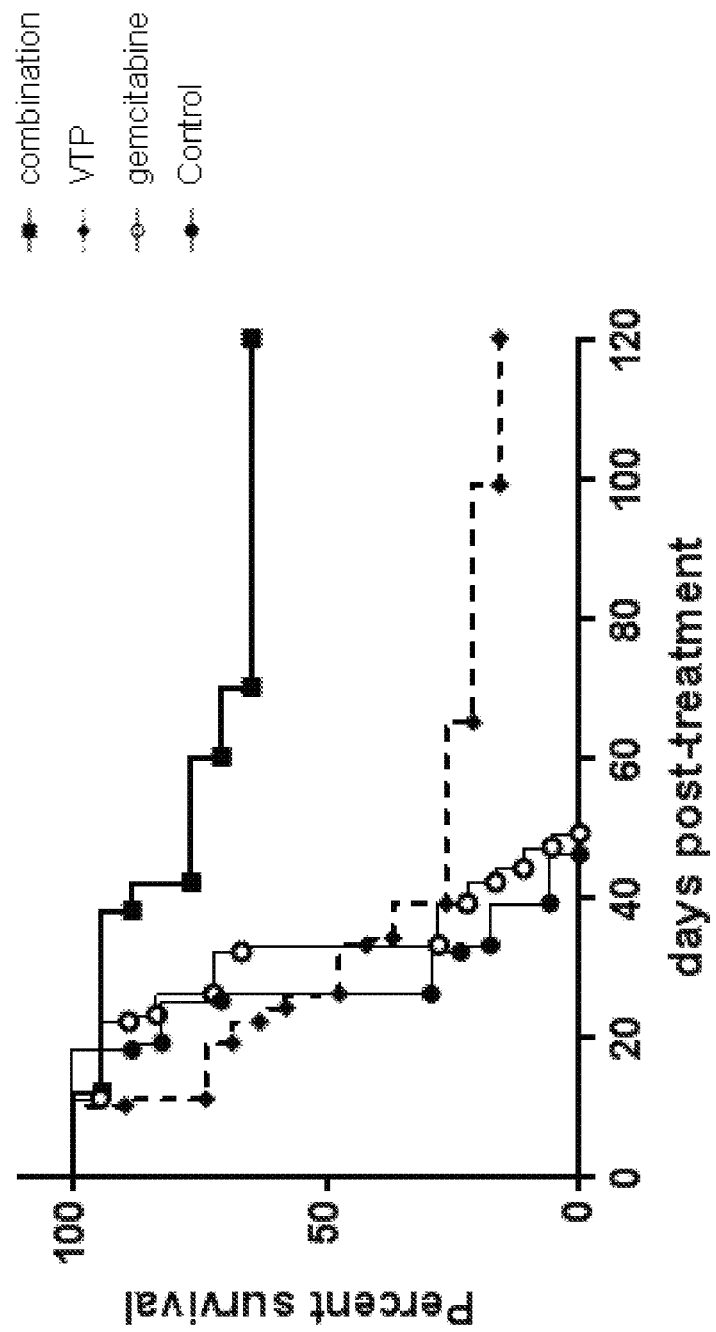

Response of Mice Grafted with MB49 Tumors to Different Regimens of Treatment with WST11 VTP and Gemzar FIGS. 8A-D show the response of Balb/C mice grafted with MB49 tumors to the different treatment regimens described in FIG. 7. FIGS. 8A-8B show the average and individual MB49 tumor growth, respectively, in the mouse hind leg following the treatment with the above WST11 VTP/Gemzar combination (error bars, SEM control vs combination therapy p<0.0001, Gemzar vs combination therapy p<0.0001, VTP vs combination therapy p<0.0005 (Two way Anova test)). All control animals had to be sacrificed because of tumor burden at 20-25 days post grafting. Gemzar or WST11 VTP single treatment modalities slightly delayed tumor progression and resulted in 0 (Gemzar vs combination therapy p<0.0001) and 16% (VTP vs combination therapy p<0.001) cure, respectively. However, the combined treatment showed 65% disease-free animals at 100 days post tumor grafting. FIG. 8C depicts the prevention of lung distant metastases (imaging, A103+A112) at day 25 in response to non-treatment (control) and treatment by the different treatment regimens (Gemzar, VTP or VTP+Gemzar), monitored weekly by IVIS bioluminescence imaging. Representative luminescence images from animals of four treatment groups are shown on the low panel and quantification of average luminescence intensities from the metastatic tumor sites at day 25 post VTP are plotted in the upper panel. The improvement of overall survival in combination cohort shown in FIG. 8D was statistically significant (VTP vs combination therapy, p<0.001; Gemzar vs combination therapy, p<0.0001). Overall survival (OS) was plotted as a Kaplan-Meier curve and the log-rank test was used for statistical analysis. Mice were euthanized when the leg tumors reached 2500 mm$^3$ and counted as dead. All data were combined from two separate experiments.

Example 9

Figure 9A:
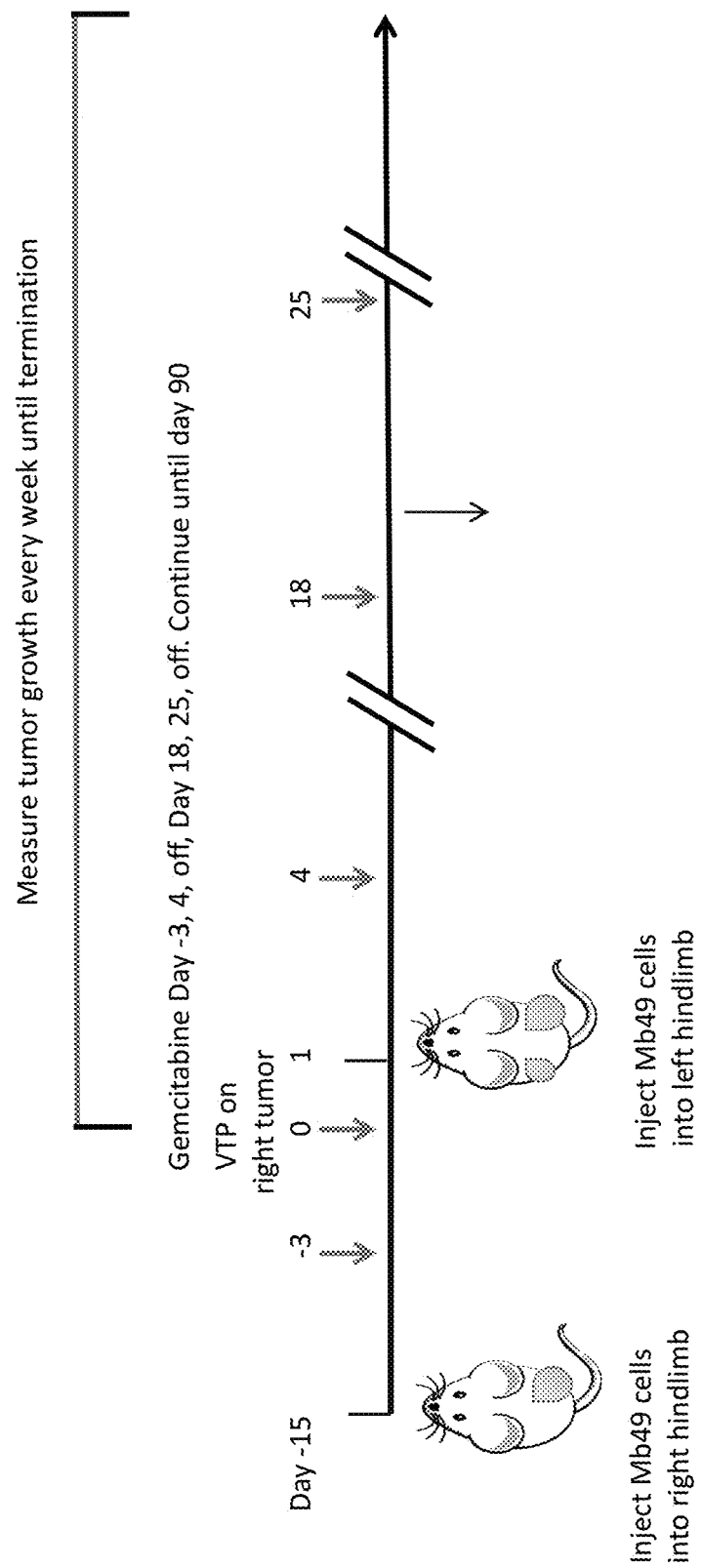
FIG. 9 shows the evolution of systemic anti-tumor response following different treatment regimens. MB49 cancer cells were grafted on the right hind leg of Balb/C mice at day −15. (9A) First Gemzar administration (50 mg/kg) was performed at day −3, then at day 4 and continued in cycles of 2 times/week, for 3 weeks. Then one week off and again a three weeks cycle to a total of 12 treatments/90 days. WST11 VTP was performed at day 15 post grafting with WST11 at 9 mg/kg infused i.v. for 5 minutes followed by 10 minutes illumination at 753 nm using Modulight laser at 120 mW/cm$^2$. Second tumor was grafted at the hind left leg at day 1 post VTP. (9B) Tumor growth in individual animals of a second tumor grafted at the left hind leg 1 day post WST11 VTP; Upper panel left-control (growth in 14/20 animals), Upper panel right-Gemzar (growth in 15/20 animals), Lower panel left-WST11 VTP alone (12/19 growth), Lower panel, right-VTP+Gemzar (5/17 growth). (9C) Kaplan-Meier survival curves for animals that were cured of MB49 by PDT and then injected MB49 cell into the tail vein.
Figure 9B:
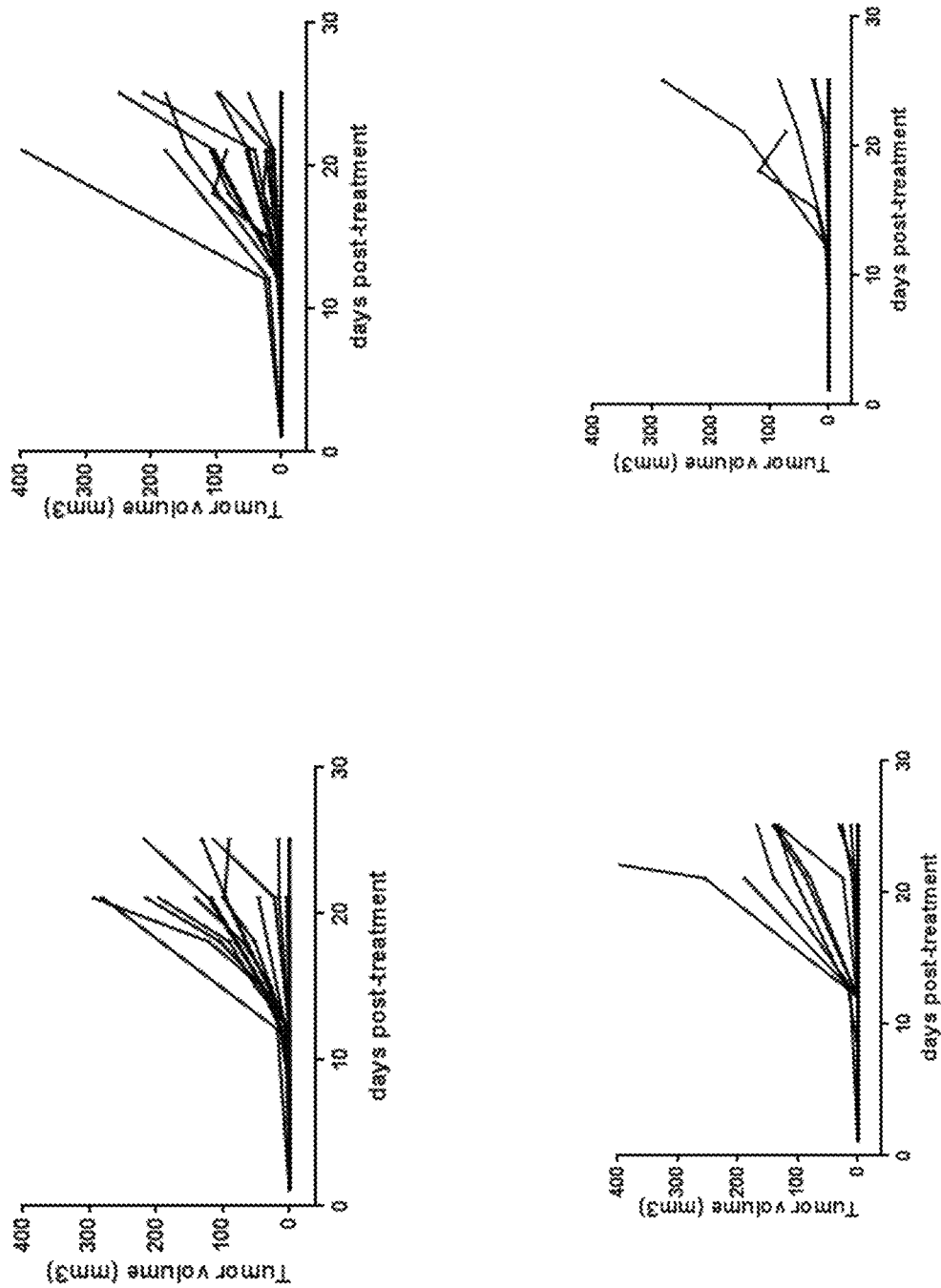
Figure 9C:
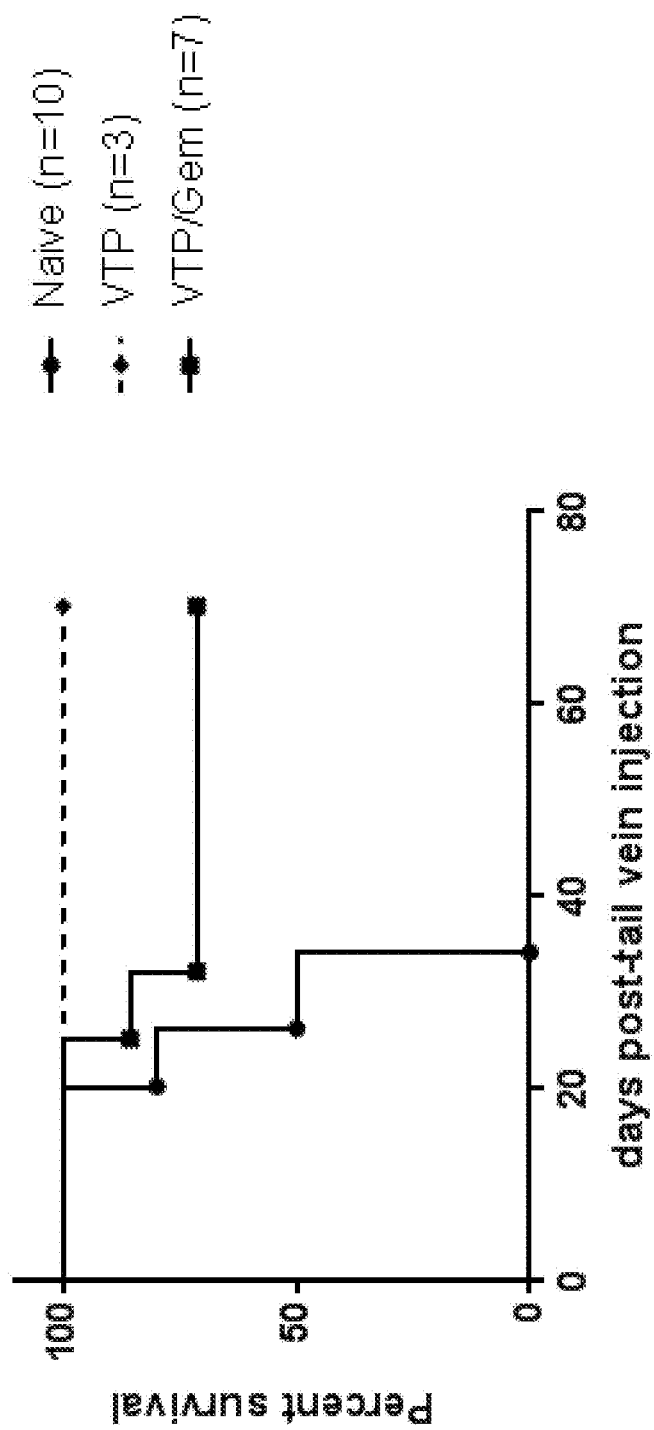

Evolution of Adaptive Anti-Tumor Immunity as Reflected in the Metastatic Evolution and Re-Challenge Success in Animals Treated by WST11 VTP and Gemzar Animal model and treatment scheme aimed to examine the evolution of systemic anti-tumor response in animals bearing Mb49 cells following different administration regimens of WST11 VTP with and without Gemzar administration was tested as illustrated in FIG. 9. FIG. 9A depicts the treatment Scheme 3. VTP was performed when at day 15 post grafting, tumors reached 4-7 mm in diameter (day 0). Mice were challenged the following day after VTP ablation with a second injection of MB49 on the left hind leg. Gemzar was administered weekly (3 week cycle, 3$^{rd}$ week off) at 50 mg/kg to the cohorts of Gemzar and combination up to 90 days starting 3 days prior to VTP. FIG. 9B relates to second tumor growth in individual animals of a bilateral model. The four panels show tumor growth in non-treated mice (control) or mice treated with Gemzar, WST11 VTP or a combination thereof, showing that 71% of mice in combination cohort stayed tumor free. FIG. 9C presents Kaplan-Meier surviving mice that at day 125 post VTP treatment (the last Gemzar dose was given at day 90) were re-challenged via tail vein injection of MB49 cell line. All of untreated naïve mice succumbed to death by 35 days after injection of MB49 cells while 70% of mice survived after WST11 VTP or WST11 VTP/Gemzar rejected the tumor cells.

Example 10

Figure 10B:
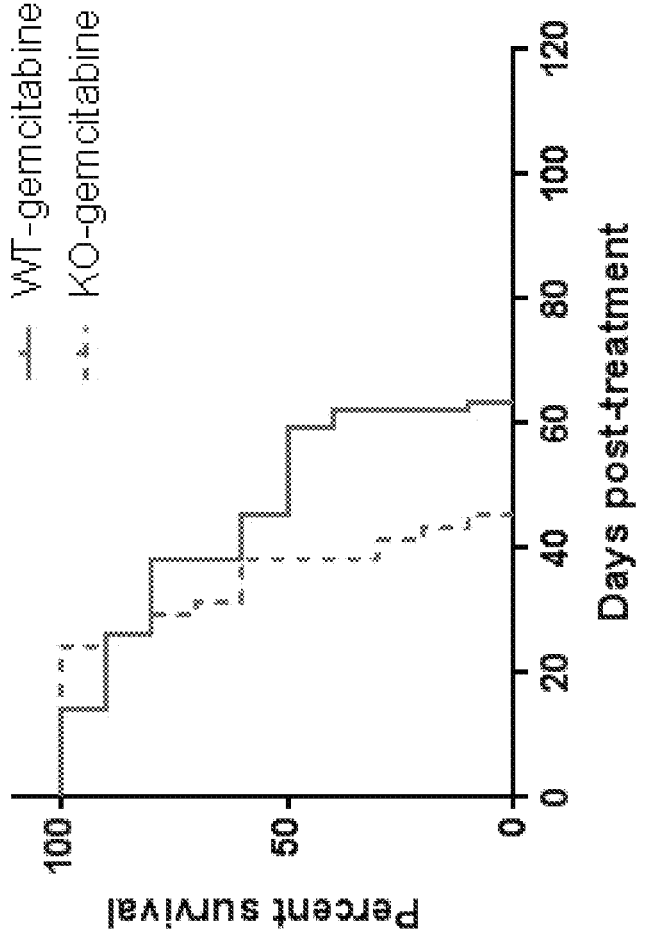
FIG. 10 shows that lack of T-cell and B-cell populations reduces the therapeutic effect of VTP, gemcitabine and combination thereof in MB49 tumors. (10A) Kaplan-Meier curves showing statistically significant decrease in overall survival of immune-compromising (Rag1KO, n=22) mice compared to immune competent ((WT N=19) mice treated with WST11 VTP (p<0.0001). (10B) Overall survival of mice treated with Gemzar alone (WT N=10, Rag1KO N=10, p<0.05). (10C) Overall survival of mice treated with combination (WT N=10, Rag1KO N=7, p<0.005).

The Impact of T and B Cells Deficiency on the Response of Tumor Bearing Mice to Treatment with WST11 VTP and Gemzar FIG. 10 shows that lack of T-cell and B-cell populations reduces the therapeutic effect of WST11 VTP, Gemzar and combination thereof in MB49 tumor bearing Balb/C mice. Effect of host immune system on the treatment efficacy was assessed using immune compromised (Nude) Rag1 KO mice (KO, dotted line) matching the background of WT C57B/6 mice (WT, full line). Kaplan-Meier curves in FIG. 10A show statistically significant decrease in overall survival of immune compromised mice compared with WT mice treated with WST11 VTP (WT n=19, Rag1KO n=22, $p<0.0001$). Similar difference was found (FIG. 10B) in the overall survival of mice treated with gemcitabine (Gemzar) alone (WT n=10, Rag1KO n=10, $p<0.05$). While 30% of immune competent mice where cured by the combined treatment in this experiment (FIG. 10C) No cure was found in the immune compromised mice treated with combination of WST11 VTP and Gemzar at 120 mg/kg or 60 mg/kg ($p<0.24$) (WT n=10, Rag1KO n=7, $p<0.005$). The effect of all three treatment modalities was diminished in Rag1 KO mice indicating that T-cell population mediates therapeutic effect of VTP, Gemzar or the combination thereof.

Examples 11-18 below provide insight to the innate and immune response of tumor-bearing animals to the different treatment protocols described in the present application.

Example 11

Immune Cells Population in the Spleen of Non-Treated Balb/C Mice

Figure 11C:
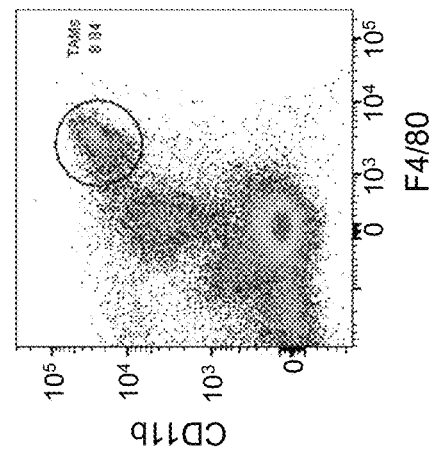
FIG. 11 provides representative diagrams of immune cells populations in the spleen of 4T1-bearing mice in non-treated (control) animals: (11A) Granulocytic/monocytic myeloid-derived suppressor cells (G/M-MDSCs) and neutrophils; (11B) Dendritic cells (DC); (11C) Tumor associated macrophages (TAMs); (11D) CD4 & CD8 T cells; (11E) Gating of T regulatory cells (Tregs).
Figure 11A:
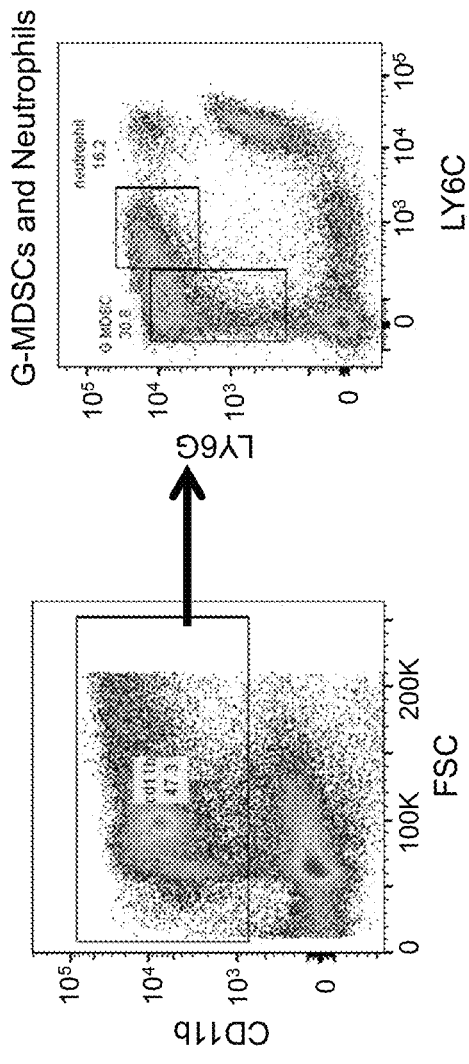
Figure 11B:
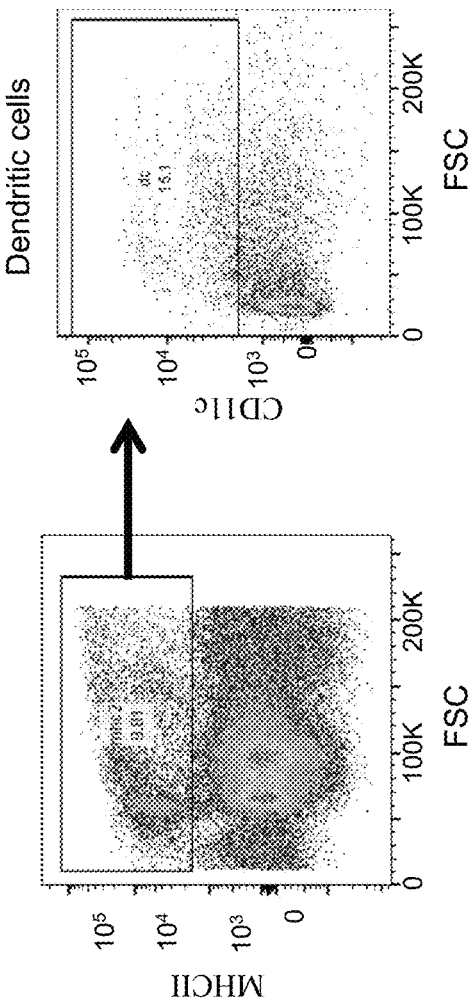

FACS analyses of immune cells populations in the spleen of control (no treatment) 4T1-bearing mice was carried out as described in Material and Methods hereinabove. The results are shown in FIG. 11: (A) Granulocytic/monocytic myeloid-derived suppressor cells (G/M-MDSCs) and neutrophils; (B) Dendritic cells (DC); (C) Tumor associated macrophages (TAMs); (D) CD4 & CD8 T cells; (E) T regulatory cells (Tregs).

Example 12

Figure 12C:
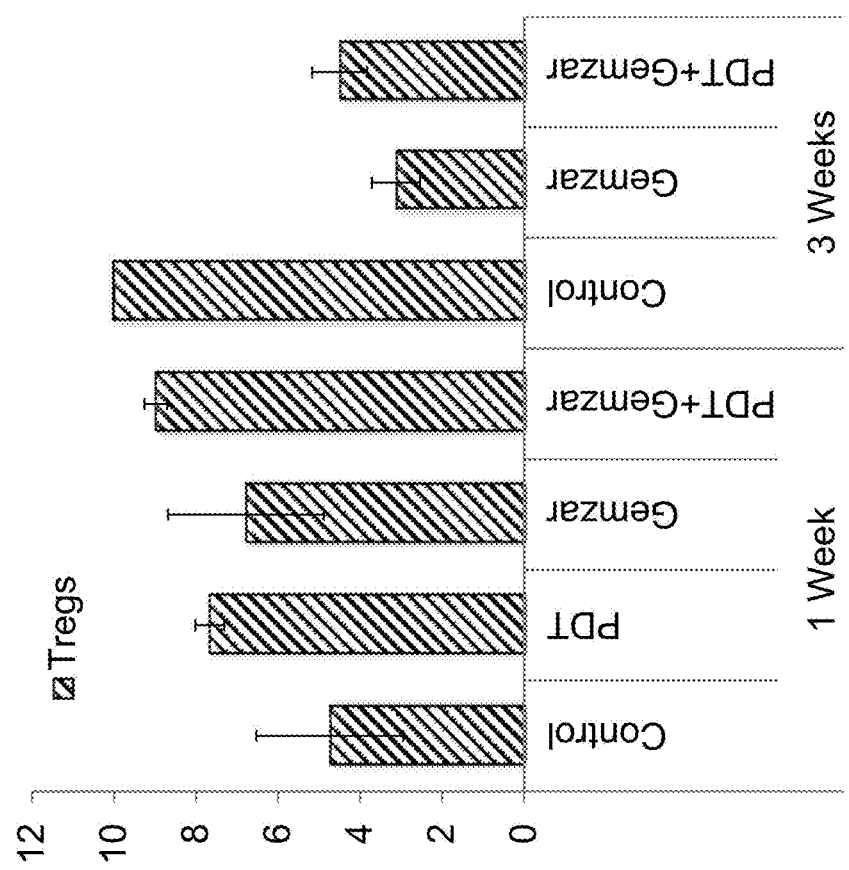
FIG. 12 illustrates the treatment impact of STL-6014-PDT combined with Gemzar administration as described by treatment Scheme 1 (depicted in FIG. 2) on the splenic immune cells populations in 4T1-bearing mice at 1-3 weeks post treatment. (12A) G/M-MDSCs (blank), TAMs (black). (12B) DC (blank), CD8 (black); (12C) Tregs.

The Treatment Impact of STL-6014-PDT Combined with Gemzar Administration on the Immune Cell Profile in Spleen of 4T1-Bearing Mice FIG. 12 presents the treatment impact of STL-6014-PDT combined with Gemzar administration on the immune cell profile in spleen of 4T1-bearing mice. The profile of splenic cell populations was assessed following 3 treatment regimens: STL-6014 PDT, STL-6014 PDT with Gemzar (starting 2 days before PDT), and Gemzar alone. Treated groups were compared to tumor-bearing controls. Animals with good treatment responses (as judged by primary tumor ablation at 1, 2, and 3 weeks post-treatment) were taken for analysis. Splenocytic cells were stained for innate and adaptive immune markers and analyzed by LSRII flow cytometer (BD Bioscience, San Jose, Calif.) and analyzed using FlowJo software (Tree Star, Ashland, Oreg.). In the first week post treatment, both PDT and Gemzar alone significantly reduced the percentage of G-MDSC/neutrophils and M-MDSC compared to control. But the effect of the combined treatment modality appeared much stronger. At the second week post treatment, the impact of Gemzar alone relative to control diminished, while that of PDT was highly significant and that of the combined therapy was very strong. At the third week, the MDSCs were attenuated only in the combination-treated animals compared to the control. The sustainability of the combined therapy on the MDSC profile nicely correlates with the time required for the evolution of adaptive immunity (Fisher et al., 2017; Nowak et al., 2003; Pitt et al., 2016). Complementary, the combined treatment dramatically elevated the dendritic cells population compared to control, particularly in the first two weeks and that of the CD8 cells throughout the three weeks post treatment. Much smaller effects were observed on the Treg populations for all three treatment modalities compared with controls.

Example 13

Impact of WST11 VTP and Gemzar on the Spleen of Treated Animals

Figure 13:
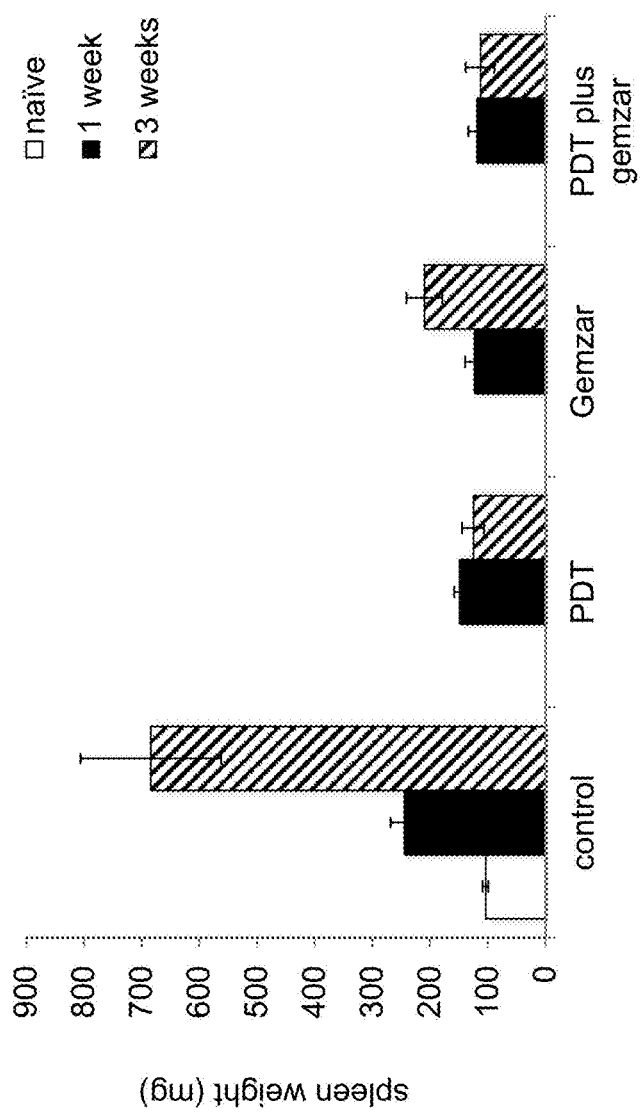
FIG. 13 shows changes in the spleen weight of animals orthotopically grafted with 4T1 cancer cells following at 1 and 3 weeks post no treatment of animal bearing tumors at 7 days post grafting treatment by STL-6014 PDT alone, treatment by Gemzar alone and combination treatment. Treatment scheme is illustrated in FIG. 2.

FIG. 13 compares changes in the spleen weight of animals orthotopically grafted with 4T1 cancer cells and not treated (control) with tumor bearing animals that underwent Gemzar treatment, WST11 VTP treatment or their combination. The six fold increase in the spleen weight found in non-treated animals is completely prevented by VTP and VTP+Gemzar and almost completely avoided by Gemzar alone. Combining with data presented in FIGS. 11 and 12 the spleen weight increase is mainly due to increased population of granulocytes and monocytes which is greatly reduced by the VTP+Gemzar treatment.

Example 14

Figure 14A:
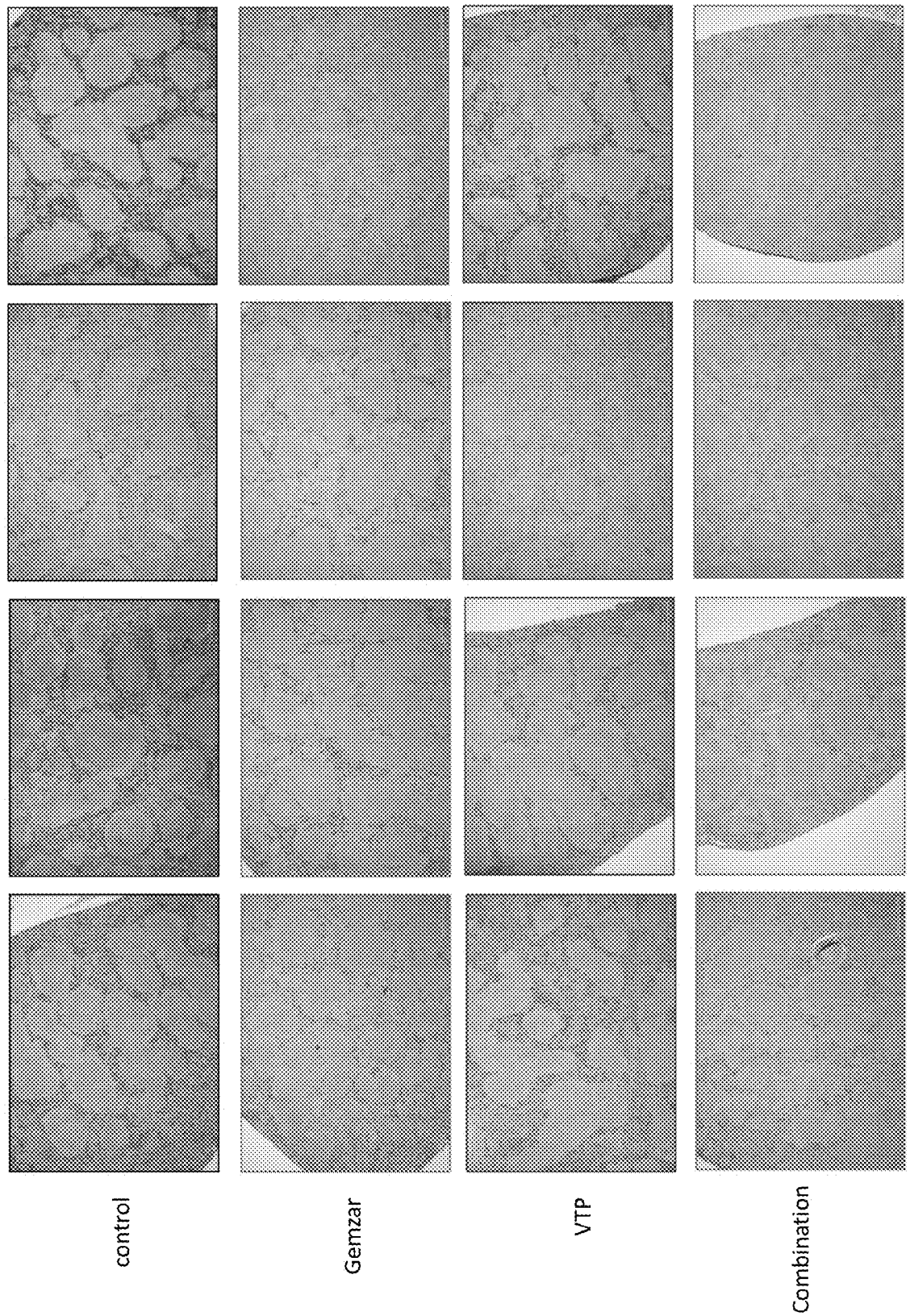
FIG. 14 depicts the innate immune cell population in the spleen of animals grafted with MB49 tumors in the hind leg and underwent no treatment (control) and animals that underwent WST11 VTP in combination with one of two Gemzar treatment regimens. (14A) Imunohistochemical (IHC) staining of CD11b+ in the spleen at day 6 post VTP (4×Bar 200 m). (14B) Neutrophils/G-MDSC (CD11b+ Ly6G+, middle graph) and monocytes/M-MDSC (CD11b+ Ly6C+, rightmost graph) at day 9 post WST11 VTP. The animals selected for FACS analysis were dosed by Gemzar at day −3, 1, 4, 7 at either low dose (60 mg/kg, red) or high dose (120 mg/kg, green) (**p<0.01, *p<0.05).
Figure 14B:
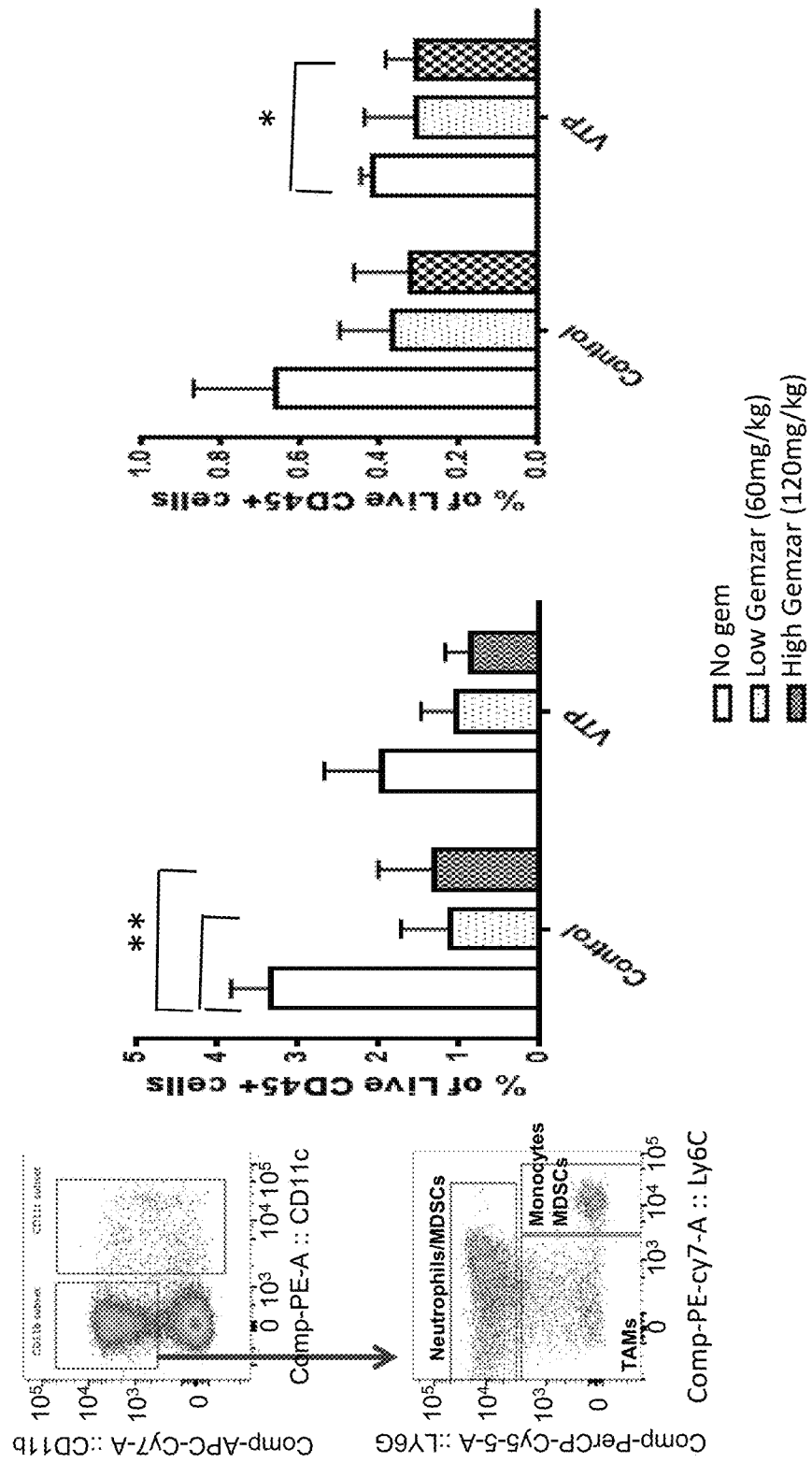

The Impact of WST11 VTP Combined with Gemzar Administration on the Evolving of Anti-Tumor Innate Immunity in 49 MB Tumor Bearing Mice The Innate immune response to different therapeutic regimens of mice bearing MB49 tumors is depicted in FIG. 14. (A) Imunohistochemical (IHC) staining of CD11b+ in the spleen shows that both VTP and gemcitabine alone depletes CD11b+ cells in the spleen but the combined treatment has much stronger effect. (B) FACS analysis on splenocytic cells of the treated animals shows that at day 9 post treatment neutrophils/G-MDSC and monocytes/M-MDSC are depleted systemically by WST11 VTP alone or gemcitabine treatment. Here, the combination didn't lower myeloid population suggesting that VTP and Gemzar might target the same cell population. Dosing schedule of Gemzar for flow was days −3, 1, 4, 7 at either low dose (60 mg/kg) or high dose (120 mg/kg). Importantly, in the 4T1 mice models the combinational treatment had more profound effect that each of the individual treatment modalities.

Example 15

Figure 15A:
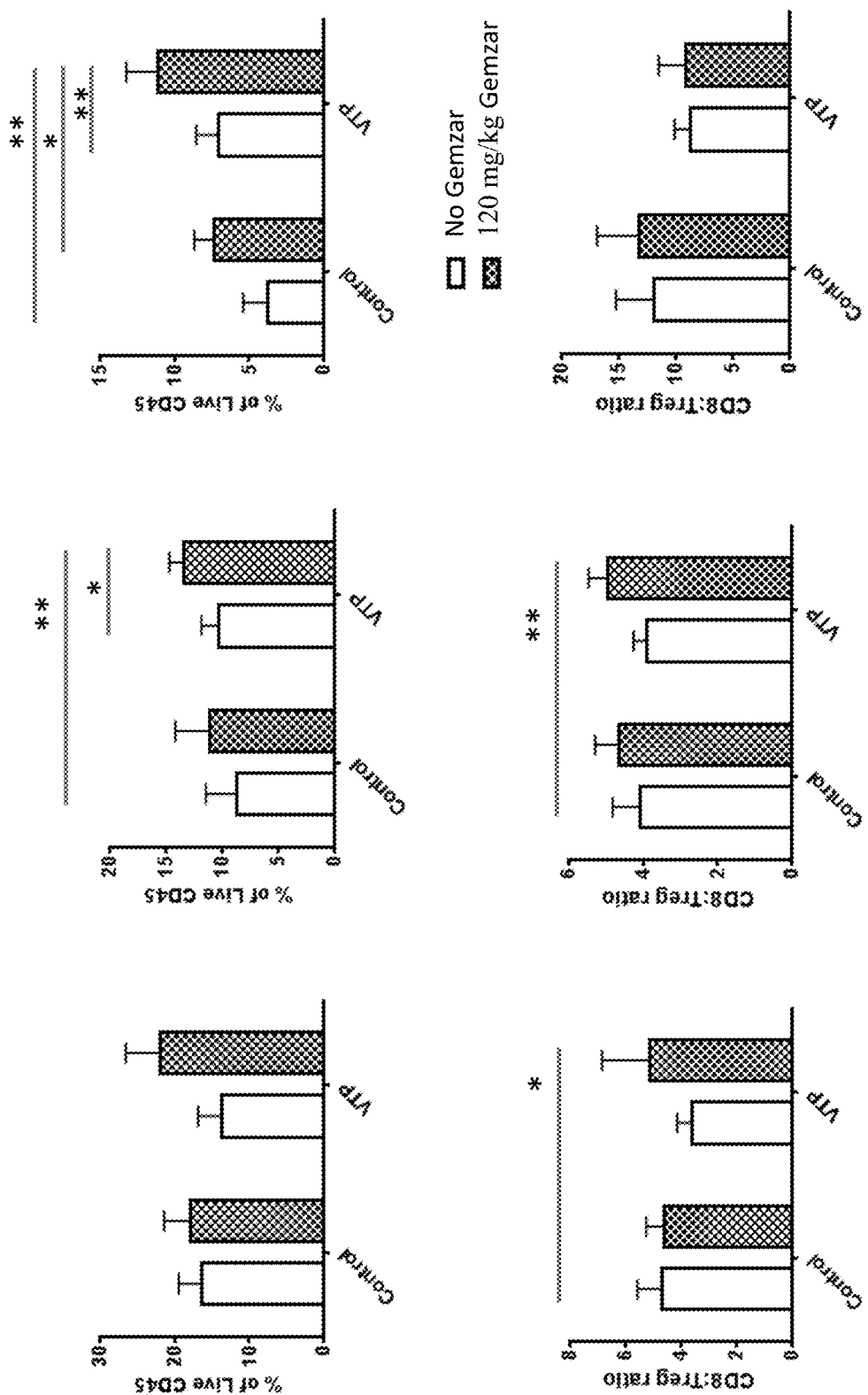
FIG. 15 depicts the adaptive immune response of mice bearing MB49 tumors to different treatment regimens. Left-draining lymph nodes, middle-spleen, right-blood; (15A) Upper panel-CD8+ cells, Lower panel-CD8+/Treg. Green-treatment or control combined with Gemzar treatment at 120 mg/Kg; Blue-treatment or control with no Gemzar treatment Impact of WST11 VTP combined with Gemzar administration as described in FIG. 7 (scheme 2) at high dosage (120 mg/kg), on the CD8+ and CD8+/Treg in the tumor, blood and spleen at day 6 post treatment (**p<0.01, *p<0.05). (15B) Upper panel-day 6, blue-no Gemzar treatment, green-gemzar treatment at 120 mg/kg; lower panel-day 9; blue-no Gemzar treatment, red-Gemzar treatment at 75 mg/Kg; Green-Gemzar treatment at 120 mg/kg; left column-Treg, middle column-Teff/Treg, right column-Tcm (activated CD8 Tcells).
Figure 15B:
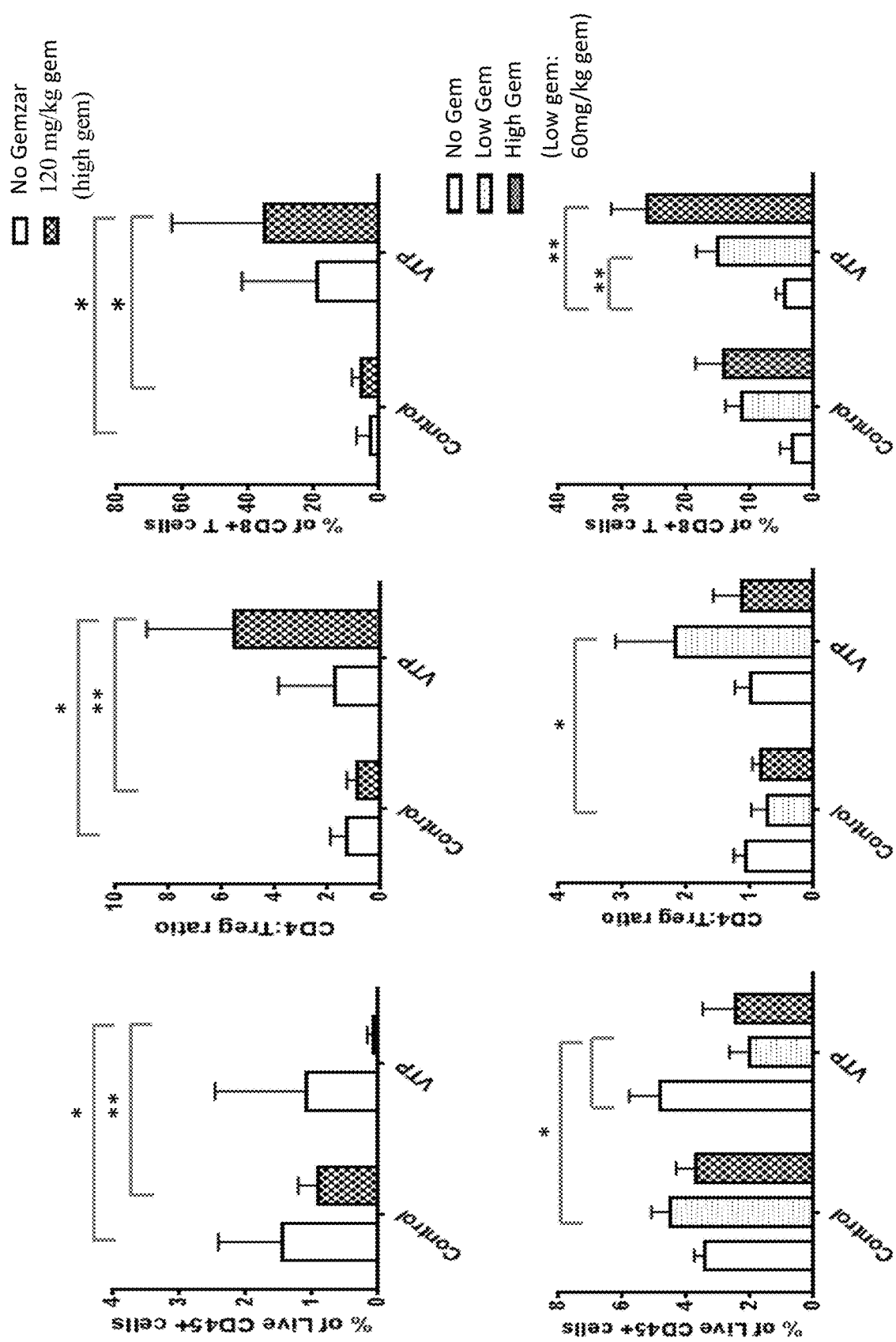

The Impact of WST11 VTP Combined with Gemzar Administration on the Evolving of Anti-Tumor Adaptive Immunity Treatment of animals bearing MB49 tumors by VTP and VTP+ Gemzar resulted in a significant elevation of the CD8 cell population in the spleen, blood and draining lymph nodes at 6 days post treatment. Interestingly, no significant effect was observed in the Treg populations at that time. However, almost complete depletion of the Treg population in the tumor was seen at 6 days after combinational therapy (FIG. 15B). WST11-VTP/Gemzar combination increased cytotoxic Tcell population (CD8) and Teff in the lymph nodes (LN), spleen and blood at day 6 post VTP, (**p<0.01, *p<0.05), showing no increase of VTP alone on the CD8 Tcell/Treg ratio but strong effect of VTP/Gemzar combination. VTP/Gem combination decreased Treg population and significantly increased the Teff population in the tumor. Enhancement of Teff/Treg value was maintained at day 9 post treatment. The level of central memory T cell ($T_{CM}$) was increased by combination in tumors at day 6 and 9 post VTP. This population has been reported to confer superior protection against cancer in several different model systems compared with $T_{EM}$ cells.

Example 16

Treatment Scheme for WST11 VTP Combined with Low Dose Application of Cyclophosphamide (CTX)

Figure 16:
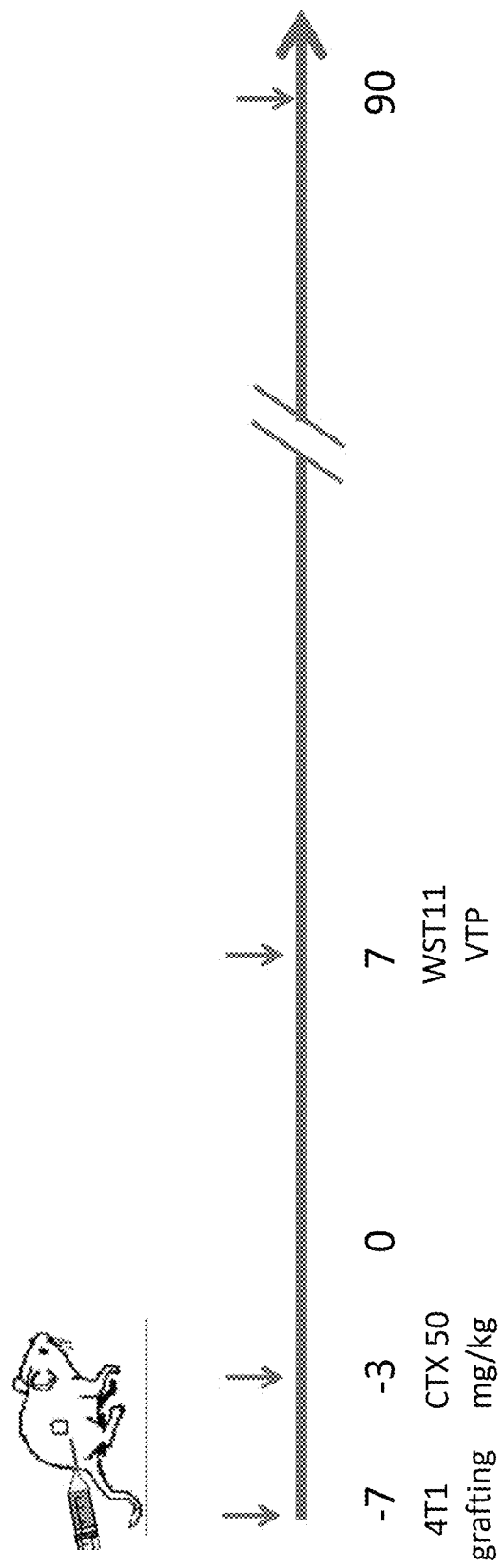
FIG. 16 depicts the WST11 VTP treatment scheme given at day 7 after tumor grafting with and without immune modulation by cyclophosphamide (CTX) given at day 3 before VTP, in mice bearing 4T1 tumors in the hind leg.

FIG. 16 illustrates the treatment scheme for WST11 VTP combined with low dose application of cyclophosphamide (CTX) as immune modulator for treatment of 4T1 tumor bearing mice. Cyclophosphamide (e.g. 50/150 mg/kg) is ip administered at 4 days post grafting of $1\times10^6$ cancer cells in the hind leg of the animal. Three days later, when tumor reaches 4-7 mm diameter, animals are infused for 10 min with WST11 (9.5 mk/Kg) and illumination at 753 nm (120-200 mW/cm$^2$) for 10-15 min is applied immediately thereafter.

Example 17

Figure 17:
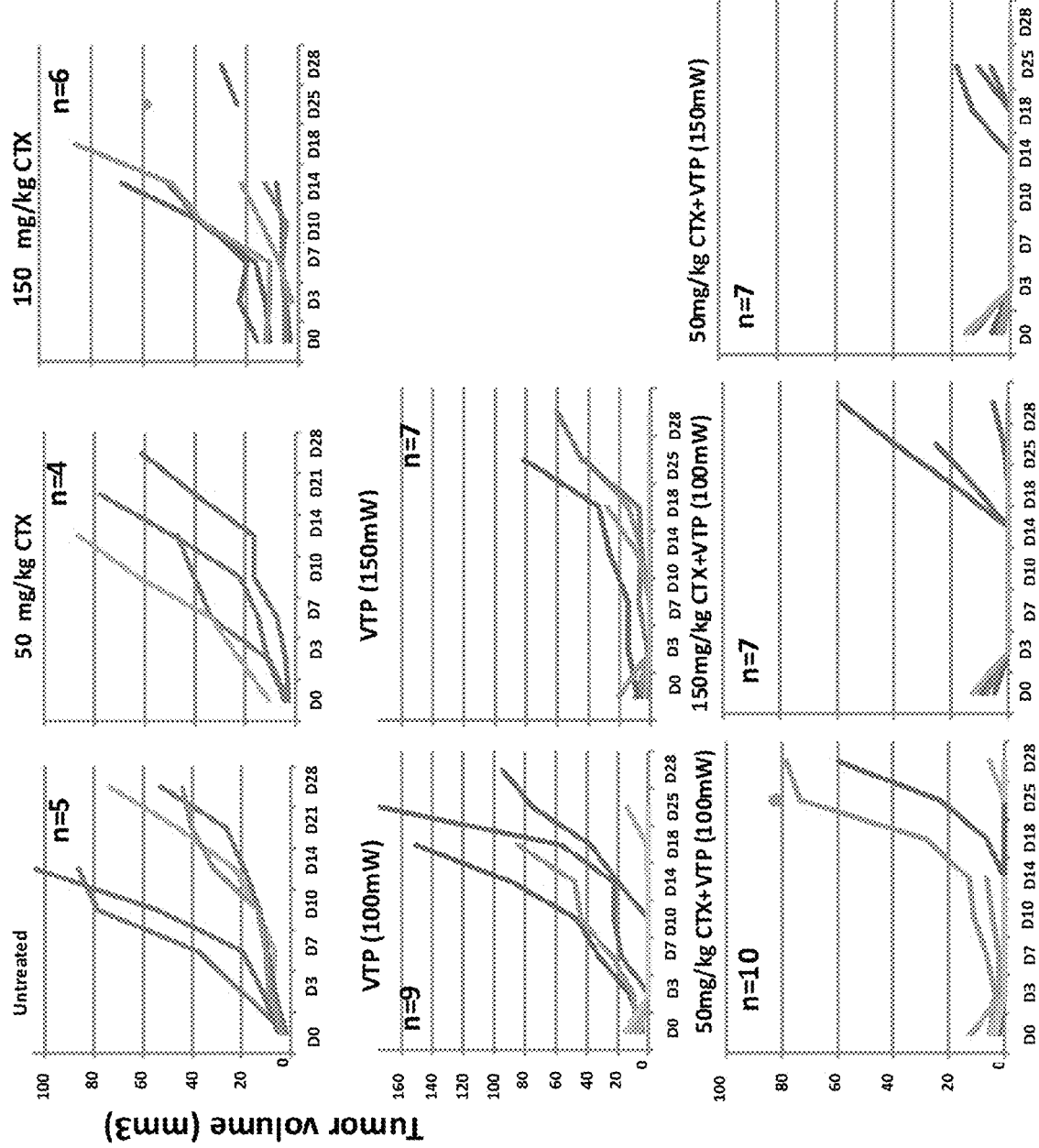
FIG. 17 illustrates the local response of individual Balb/C mice bearing 4T1 tumors in the hind leg, to different therapeutic regimens with a fixed dose 9.0 mg/kg WST11 under different light intensities (mW/cm$^2$) and CTX dosages. Upper Row: untreated mice (left, N=5), treatment with 50 mg/kg CTX (middle, N=4), treatment with 150 mg/kg CTX (right, N=6). Middle Row: treatment with WST11 VTP at 100 mW (left, N=8) or 150 mW (right, N=7). Lower Row: treatment with combination 50 mg/kg CTX+VTP 100 mW (left, N=10), 150 mg/kg CTX+VTP 100 mW (middle, N=7), treatment with 50 mg/kg CTX+VTP 150 mW (right, N=7).

Impact of Low and High Dose Cyclophosphamide (CTX) Administration on WST11 VTP-Mediated Ablation of Subcutaneous (s.c.) 4T1-luc Breast Tumors Grafted in the Mouse Hind Leg FIGS. 17 and 18 depict the impact of low and high dose cyclophosphamide (CTX) administration on WST11 VTP-mediated ablation of subcutaneous (s.c.) 4T1-luc breast tumors grafted in the mouse hind leg. Mice bearing 4T1-luc breast tumors at the hind leg were untreated or subjected to a single CTX administration alone (upper panel); treated by WST11 (VTP at low or high light intensity (middle panel); or treated by WST11 (9.0 mg WST11/kg) VTP combined with single dose CTX (50 or 150 mg/kg) given three days before VTP (lower panel). The effect of the different treatment protocols on disease progression in individual animals is depicted in FIG. 17.

Figure 18B:
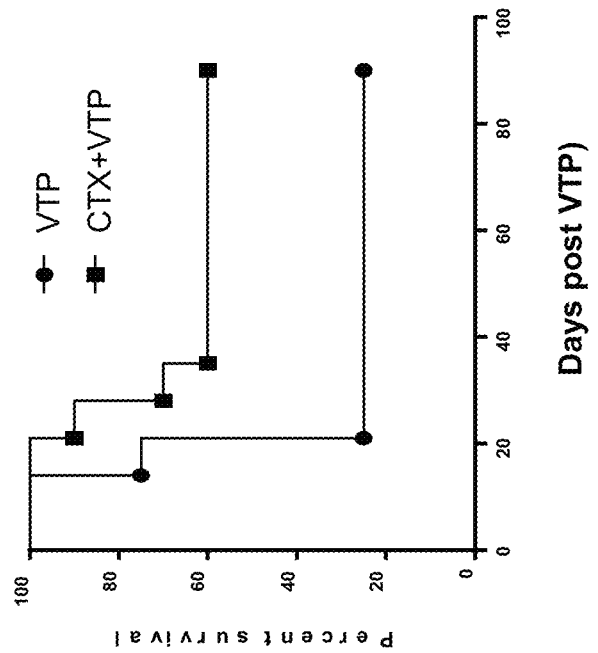
FIG. 18 presents Kaplan-Meier survival curves for Balb/c mice bearing 4T1-luc breast tumors grafted s.c. at the hind leg and subjected to WST11 VTP alone using low light intensity (100 mW/cm$^2$) (18A, 18B) or high light intensity (150 mW/cm$^2$) (18C, 18D) or in combination with single dose CTX (CY) administration (150 or 50 mg/kg) at three days prior VTP. Treatment results are illustrated for all treated mice (18A, 18C,18D) or for animals that underwent non-reversible full ablation of the primary tumor and survived with no metastases at day 90 (18D).
Figure 18A:
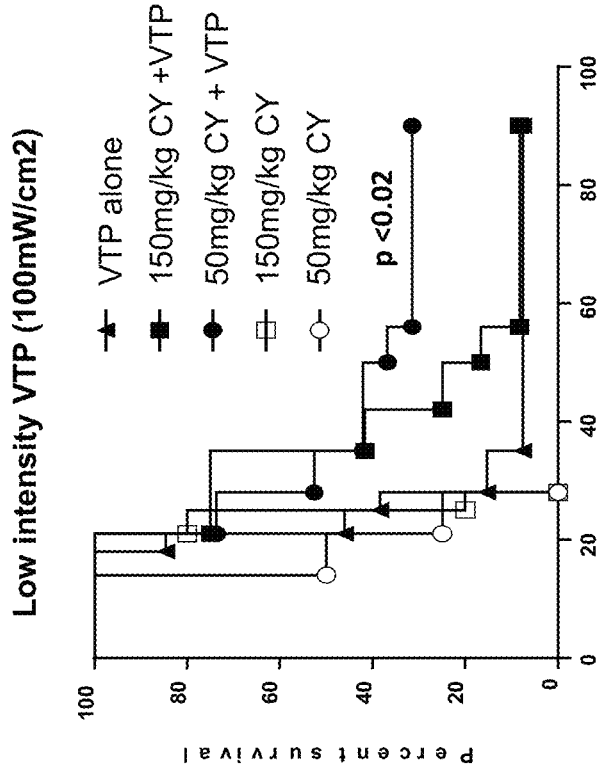
Figure 18D:
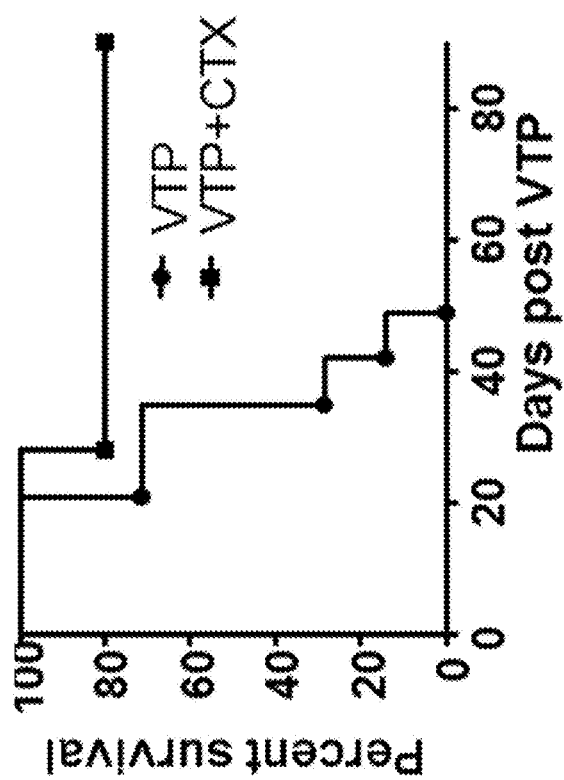
Figure 18C:
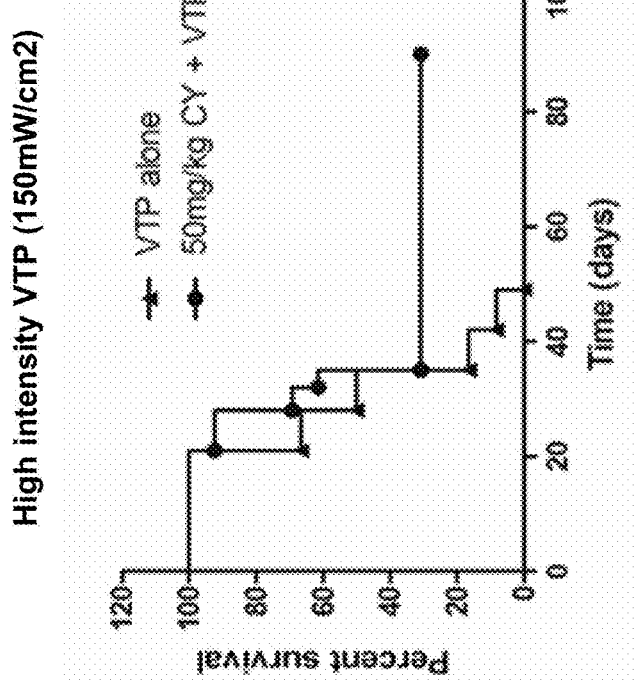

Monotherapy by CTX administration at both doses as well as WST11 VTP at low light intensity appears unable to suppress primary tumor growth. WST11 VTP at high light dose doubled the time to tumor regrowth. Combination of WST11 VTP with CTX significantly suppressed tumor growth resulting with ~60% complete ablation of primary tumors. The cumulative mice survival following the different treatment protocols is depicted in FIG. 18. Here, Balb/c mice bearing 4T1-luc breast tumors grafted s.c. at the hind leg were subjected to WST11 VTP using low (upper panel) or high (lower panel) light intensity alone or in combination with single dose CTX administration (50 or 50 mg/kg) at three days prior VTP. Treatment results are illustrated by Kaplan-Meier curves for all treated mice (FIG. 18A,C) or for animals that underwent non-reversible, full ablation of the primary tumor (FIG. 18B,D). WST11 VTP combined with low dose (50 mg/kg) CTX significantly improved mice survival culminating in 30% of mice being completely cured following 90 days follow up. Other treatment regimens, i.e. VTP with higher light dose or higher dose of CTX administration failed to provide prolonged survival resulting in local recurrences and subsequent progression to lung metastases. Within the group of mice presented with complete ablation of the primary tumors, only combined treatment induced protection agast lung metastases in significant proportion of treated mice (60-80% depending on VTP protocol).

Example 18

Figure 19B:
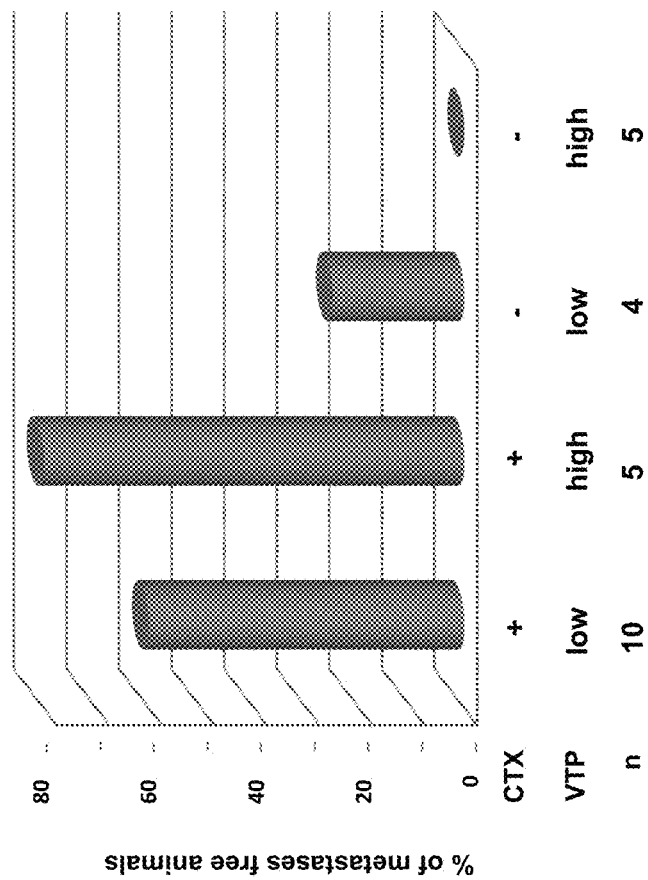
FIG. 19 shows the impact of different treatment regimens on the percentage of animals with lung metastases in Balb/c mice bearing s.c. 4T1-luc breast tumors in their hind leg. (19A). a Petri dish showing 4T1-luc colonies evolved from cells isolated from the lungs of Balb/c mouse at day 7 post grafting of 4T1-luc breast cancer cells at the hind leg (day of WST11 VTP). (19B). Percentage of metastases-free animals following complete primary tumor ablation at 90 days post treatment with: CTX (50 mg/kg)+VTP at low (N=10) or high (N=5) light intensity, or VTP alone at low (N=4) or high (N=5) light intensity.
Figure 19A:
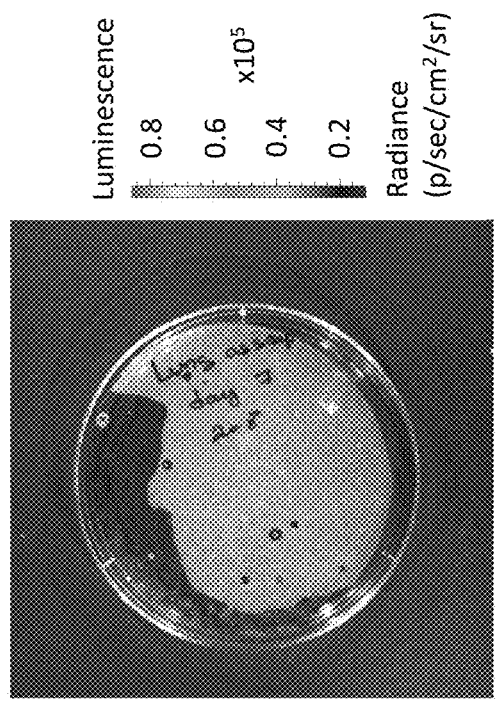

Impact of Different Treatment Regimens on the Percentage Animals with Lung Metastases in Balb/c Mice Bearing s.c. 4T1-luc Breast Tumors Balb/C grafted with 4T1 cancer cells at their hind leg, presented cancer cells in the lungs as depicted by the colony assay in FIG. 19A. Treatment of tumor bearing animals by WST11 VTP combined with CTX administration (treatment Scheme 4 as described in FIG. 16) resulted in complete annihilation of lung metastases at day 90 post grafting when high light dose and low CTX dose were applied (FIG. 19B). In contrast most of the mice subjected to VTP alone developed lung metastases, even when the primary tumor was completely ablated.

Example 19

Figure 20A:
FIG. 20A depicts representative pictures at day 7 post tumor grafting and quantification of untreated control.
Figure 20B:
FIG. 20B depicts representative picture of animals treated by CTX.
Figure 20C:
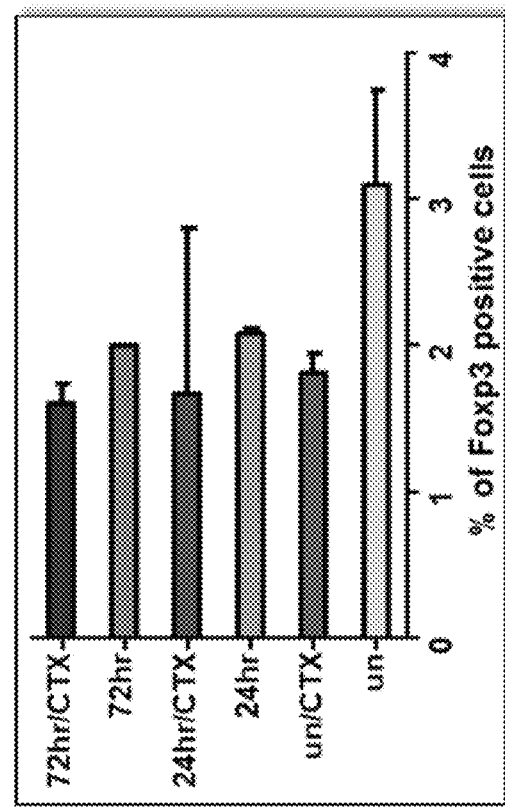
FIG. 20C depicts the percentage of Foxp3 (Treg cells) in untreated animals, animals treated by CTX at 24 hours post treatment and of animals treated by CTX at 72 hours post treatment.

The Impact of CTX on the Population of Regulatory T Cells (Tregs) in Grafted Tumors CTX was previously shown to attenuate Treg population when provided to patients at low doses under metronomic regimen. Hence, its synergistic effect on the outcome of WST11 VTP could be due to enhancement of Cytotoxic T cells activity by reducing the relative percentage of the protumoric Tregs. Indeed Foxp3 positive cells infiltration to 4T1-luc tumors grafted in the hind leg of Balb/C mice is depicted in FIG. 20. Here, 4T1 tumors were excised when reaching 30-60 mm$^3$ at indicated times post CTX or saline administration, formalin-fixed and paraffin embedded. Sections were prepared and stained for Foxp3 expression. Number of positive cells was measured using Fiji software. Representative pictures at VTP day and quantification are shown (FIG. 19A,B). CTX administration significantly reduces tumor infiltration by regulatory Foxp3$^+$ T cells three days later (FIG. 19C). This relieves immunosuppressive microenvironment in the tumor allowing anti-tumor immune responses to evolve following VTP.

Example 20

Effect of Low Dose CTX Administration at 3 Days Prior WST11 VTP on T Cell Populations in Draining Lymph Nodes and Spleens of Mice Bearing 4T1-luc Tumors FIG. 20 shows that low dose CTX administered three days prior WST11 VTP reduced the number of cells in the draining lymph nodes and spleens of tumor bearing mice on the VTP day. A significant increase in total cell numbers was observed in CTX treated animals compared to those received only VTP that show a decrease in cell counts. This finding suggested a CTX-mediated depletion of immune cells followed by repopulation with naïve immune cells. More specifically, the CTX administration reduced the number of regulatory Foxp3+ T cells in both lymph nodes and spleens following VTP compared to animals subjected to VTP alone. In the spleens, there was also small but significant increase in CD8+ cytotoxic T cells demonstrating overall shift towards immune active status beneficial for anti-tumor immunity development.

Example 21

Effect of Low Dose CTX Administration on Myeloid Cell Populations in Tumors and Spleens of Mice Bearing s.c. 4T1-luc Tumors at the Hind Flank Tumors and spleens were harvested three days post CTX administration (VTP day), cells isolated and stained for flow cytometry with anti-CD11b, Ly6G and Ly6C antibodies.

Figure 21A:
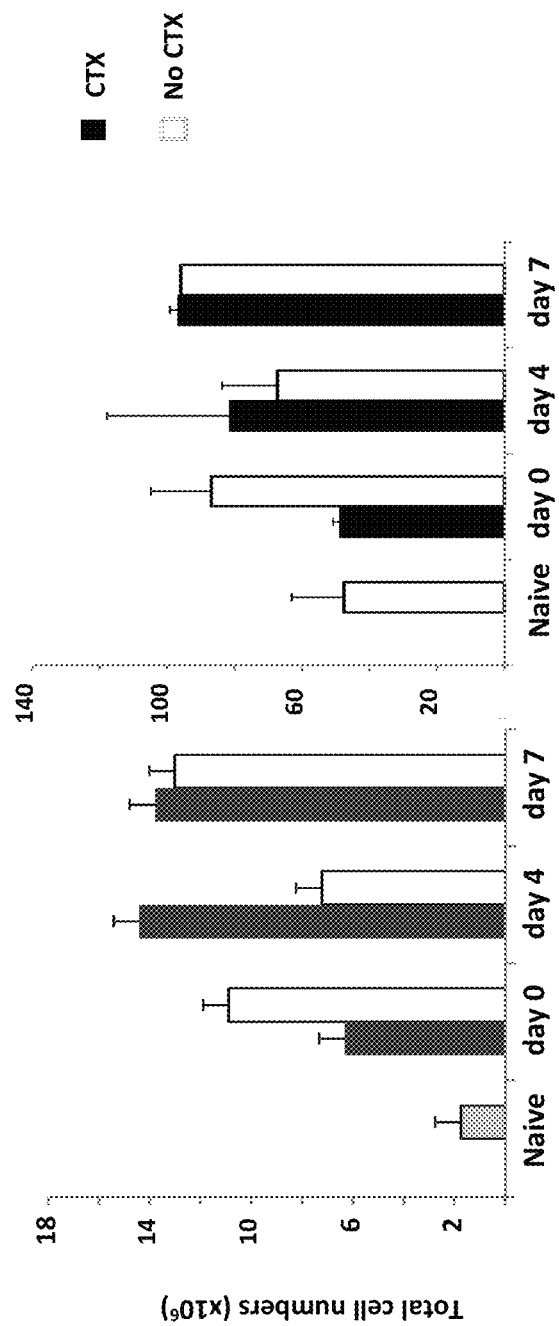
FIG. 21A Total cell counts in draining lymph nodes (LN, left) and spleen (right). LN and spleens were harvested at indicated times after WST11 VTP with (black) and without (blank) CTX administration following treatment Scheme 4 as depicted in FIG. 16. Cells were isolated and stained for flow cytometry with anti-CD4, CD8 and Foxp3 antibodies. Total cells in spleens were counted after erythrocytes depletion.
Figure 21B:
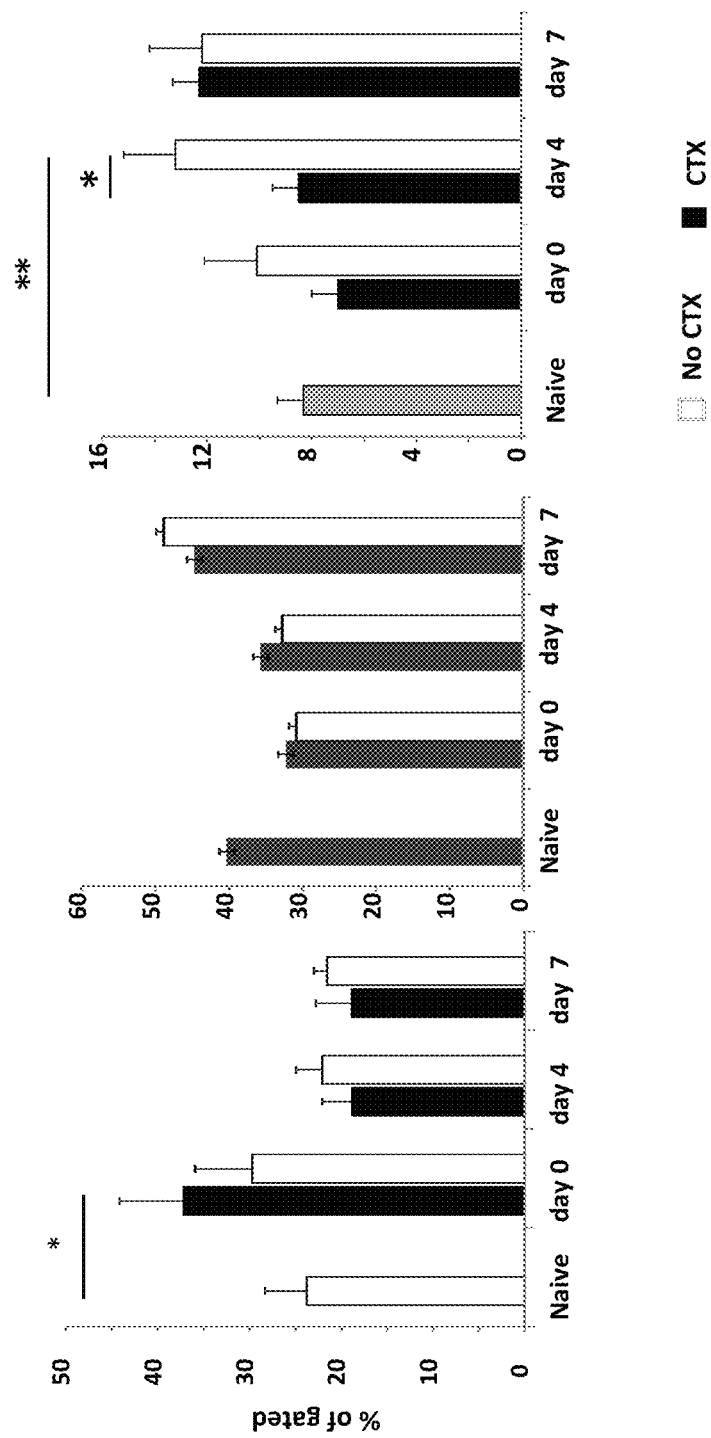
FIG. 21B. Percentage of CD8+ (left), CD4+ (middle) and Foxp3 (Treg, right) in draining LN at different times after WST11 VTP with (Black) or without CTX (blank) treatment at 3 days before VTP (*p<0.001, **p<0.05)
Figure 21C:
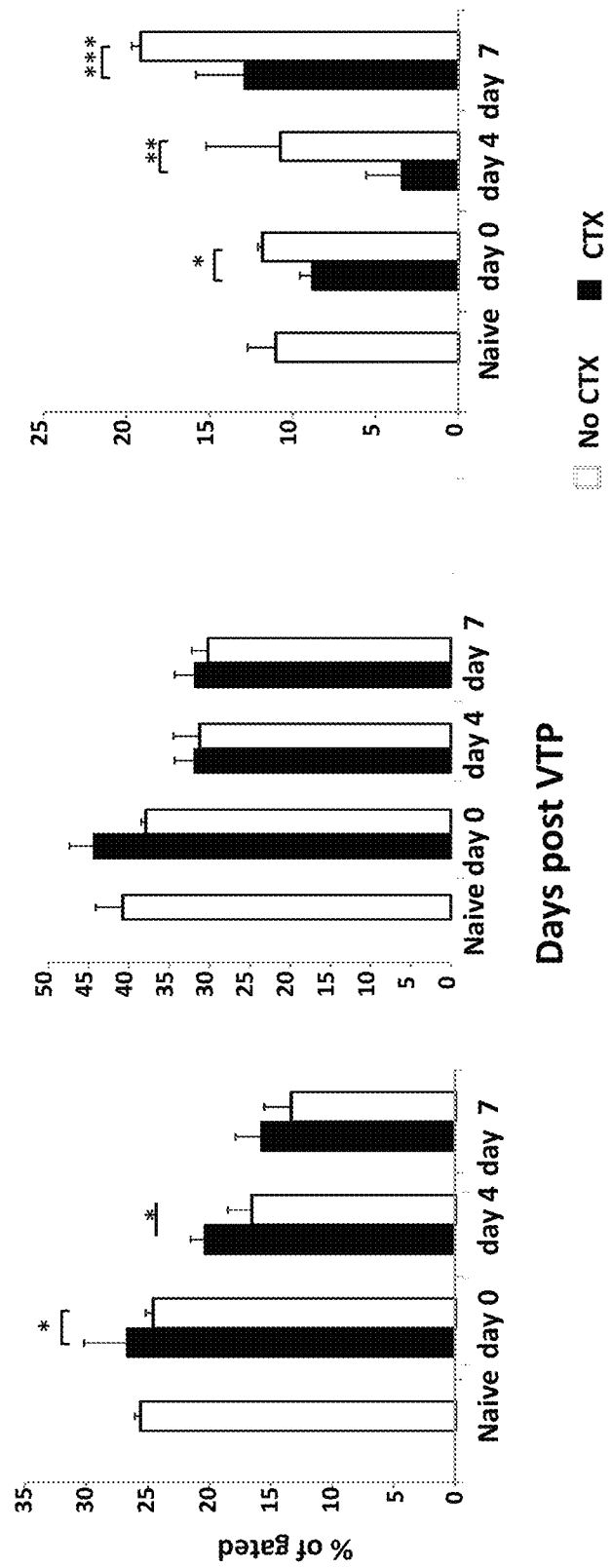
FIG. 21C. Percentage of CD8+ (left), CD4+ (middle) and Foxp3 (Treg, right) in the spleen at different times after WST11 VTP with (Black) or without CTX (blank) treatment at 3 days before VTP (*p<0.001, p<0.001, *p<0.05)
Figure 22:
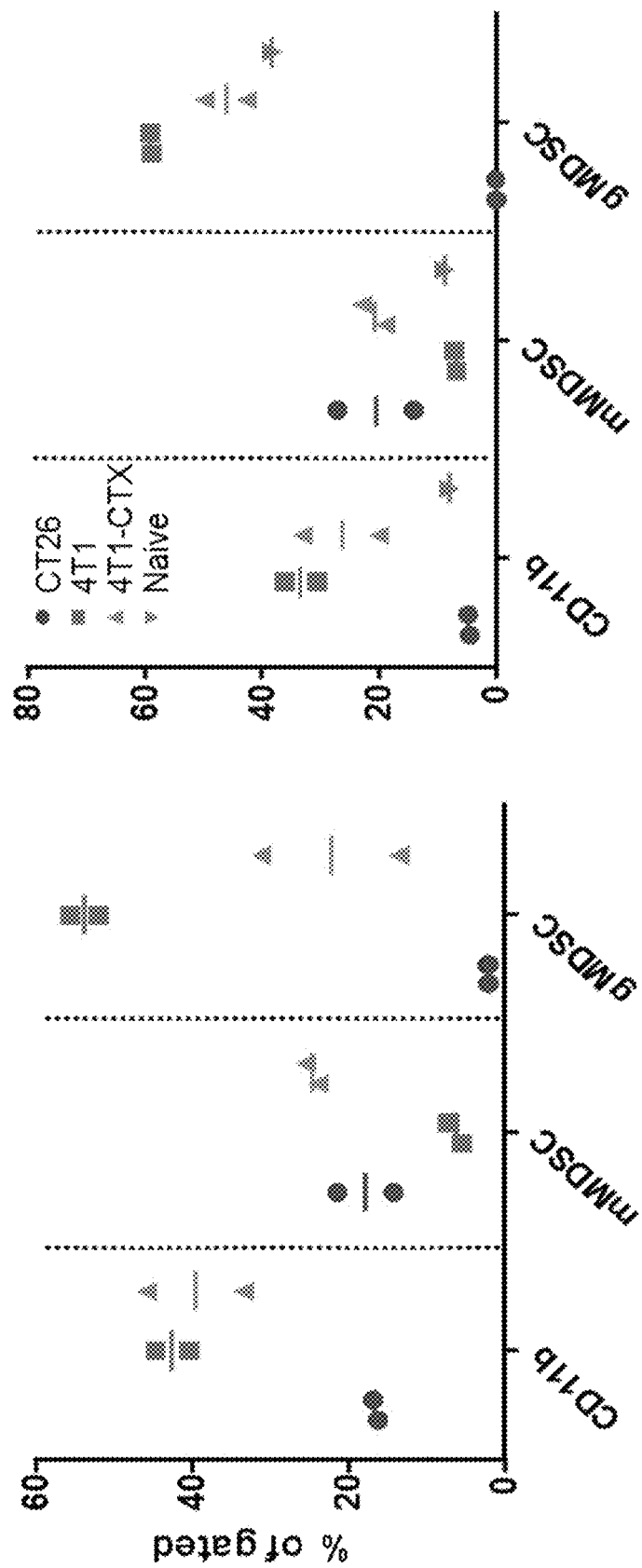
FIG. 22 depicts the effect of low dose CTX administration on myeloid cell populations in tumors and spleens of mice bearing s.c. 4T1-luc tumors at the hind leg on 7 days post grafting (VTP day). Left-tumors; Right-spleen.

FIG. 21 shows that Low dose CTX reduced G-MDCS/neutrophils known to suppress anti-tumor immune response in the tumor microenvironment allowing for more efficient immune response to evolve following VTP.

Following Examples 20 and 21, we conclude that the therapeutic advantage of CTX administration prior WST11 VTP reflects both Treg and MDSC attenuation, subjecting the animals to enhanced effect of both the innate and adaptive immune systems.

Example 22

Figure 23A:
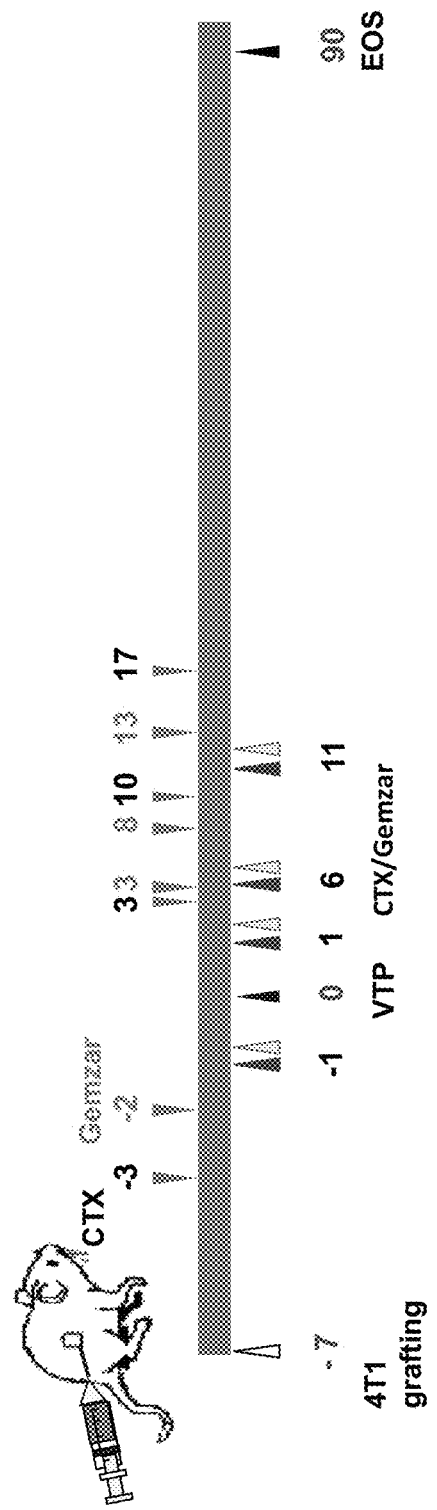
FIG. 23A shows treatment Scheme 5 for the combined treatment of mice bearing 4T1 tumors in the mammary pad using WST11 VTP alone (at 7 days post grafting, when tumors reach diameters of 5-7 mm); WST11 VTP combined with metronomic administration of CTX starting at 3 days prior VTP and given three more times (black arrows) (CTX 2); WST11 VTP combined with one dose administration of CTX at 1 days prior VTP WST11 (CTX 1) and three more times (red arrows); VTP combined with metronomic administration of Gemzar starting at two days (blue) or one day (yellow) prior VTP and continues at 5 days intervals for 3 more times. Follow up of treated animals continued to day 90 or until animal were sacrificed due to tumor burden.

Survival of Balb/C Mice Bearing Bearing s.c. 4T1-luc Tumors at the Mammary Pad Following Different Treatment Regimens Animal survival following WST11 VTP combined with CTX administration (FIG. 23A, black, 50 mg/kg) was compared to those of animals treated by WST11 VTP combined with Gemzar (FIG. 23A, blue, 75 mg/kg).

Figure 23B:
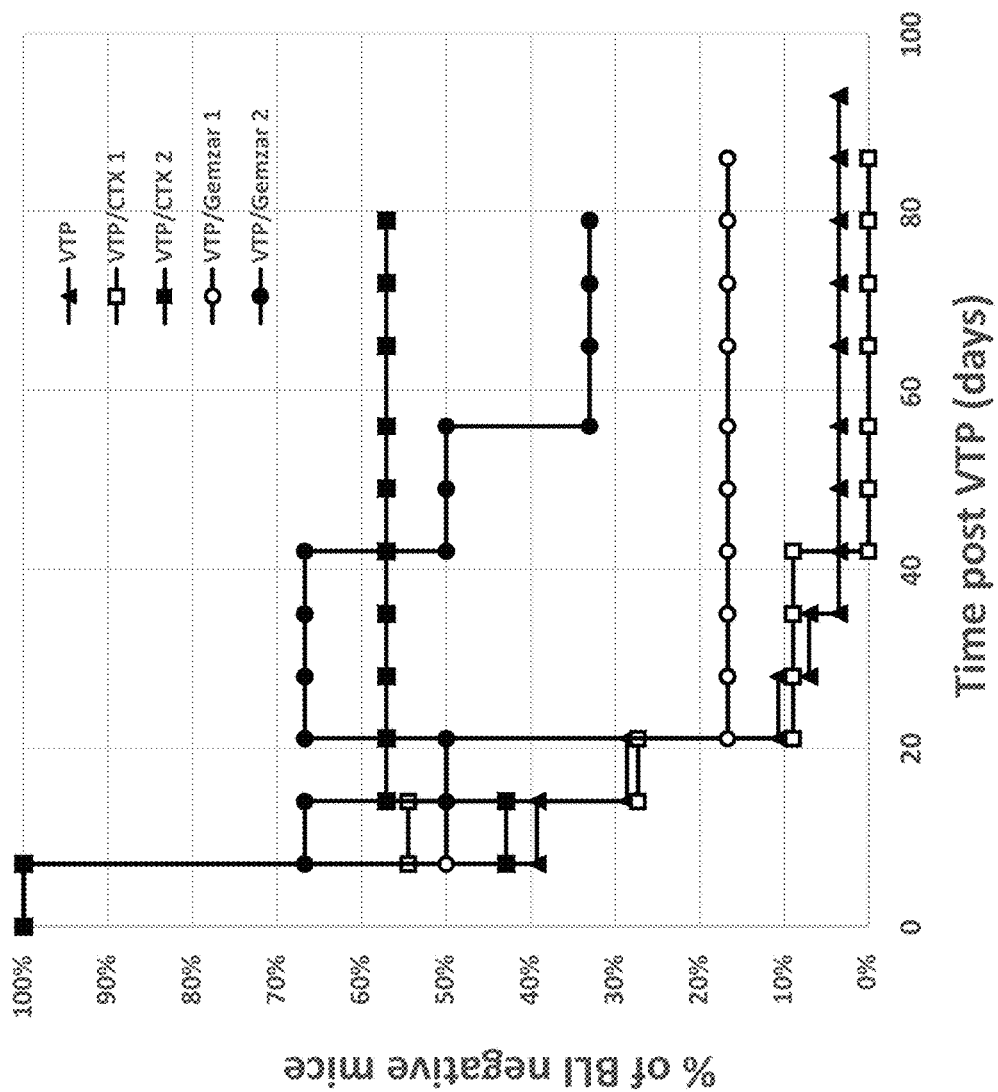
FIG. 23B presents Kaplan-Meier curves that illustrate survival of 4T1-luc tumors bearing animals in the mammary after treatment by different protocols of WST11 VTP combinations with CTX or Gemzar.

VTP alone with 9 mg/kg WST11 VTP at 200 mW/cm$^2$ illumination for 15 min resulted in very limited survival with most of the mice developing local recurrence and lung metastases (FIG. 23B—Green). Combining VTP with CTX administration started one day prior VTP and continued on days 1, 6 and 11 post VTP failed to significantly improve treatment outcome (FIG. 23B—red), while Gemzar administration according to the same protocol with VTP cured ~20% of the mice (FIG. 23B—yellow). VTP combined with Gemzar according to protocol No. 2 (starting on day −2 followed by three additional doses every 5 days) increased the survival rate to above 30% (FIG. 23B—blue). The most successful results were obtained with CTX given on days −3, 3, 8 and 13 amounting to almost 60% cured animals (FIG. 23B—grey). A chart summary of these results is depicted in FIG. 23C, and may indicate that CTX may have some adbvanytage on Gemzar treatment when combined with WST11 VTP. Still elongation of the metronomic regimen of Gemzar when combined with WST11 VTP, as demonstrated above form MB49, may reach similar cure rate to CTX1 with WST11 VTP.

APPENDIX

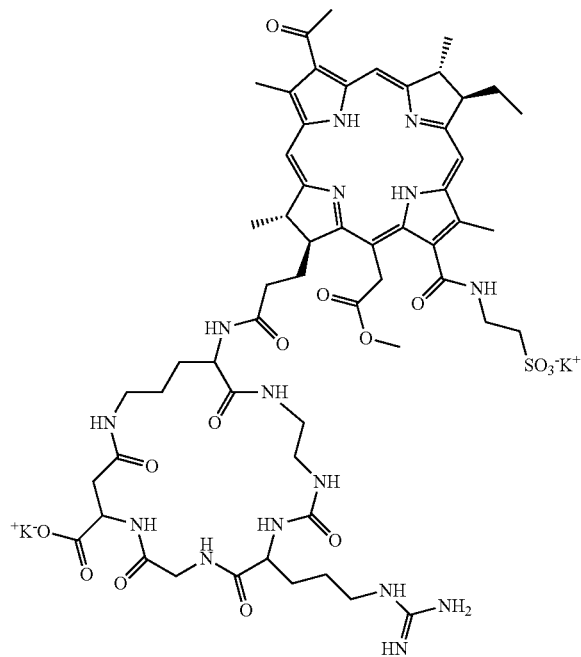

STL-6038

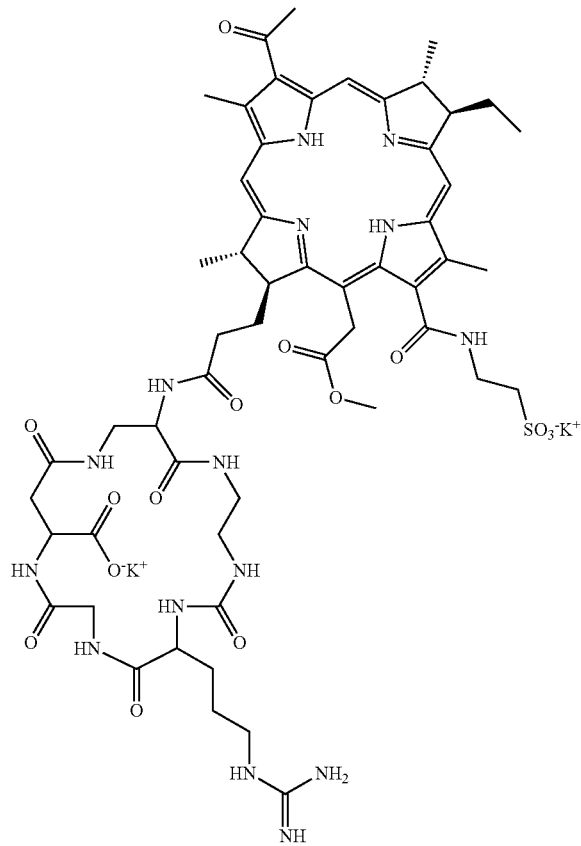

STL-6033

STL-6068

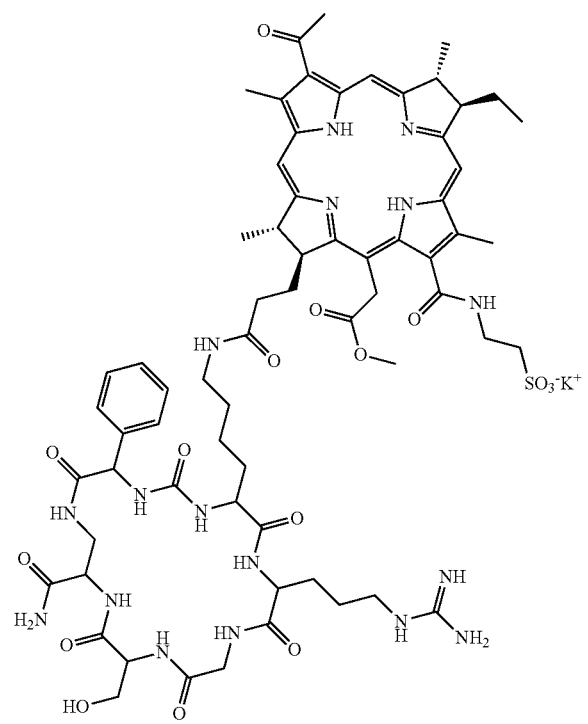

STL-7012

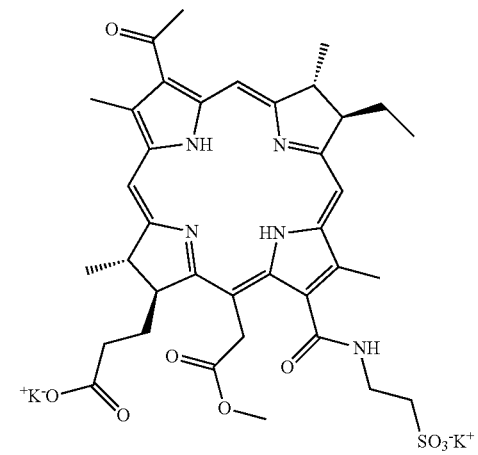

STL-6014

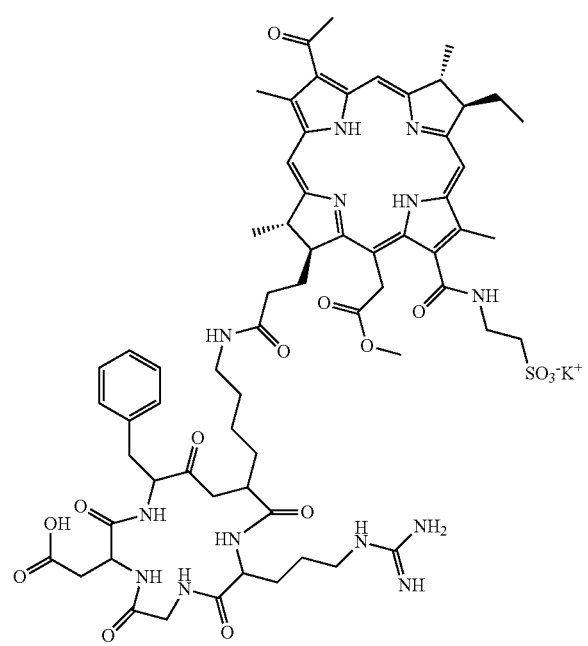

REFERENCES

Barbon, C. M., et al., 2010, Consecutive low doses of cyclophosphamide preferentially target Tregs and potentiate T cell responses induced by DNA PLG microparticle immunization. *Cell. Immunol.* 262(2): 150-161.

Castano, A. P., et al., 2008, Photodynamic therapy plus low-dose cyclophosphamide generates antitumor immunity in a mouse model. *Proc. Natl. Acad. Sci. USA* 105(14):5495-5500.

Gabrilovich D. I., 2017, Myeloid-Derived Suppressor Cells, *Cancer Immunol. Res.* 5(1):3-8.

Ge, Y., et al., 2012, Metronomic cyclophosphamide treatment in metastasized breast cancer patients: immunological effects and clinical outcome. *Cancer Immunol. Immunother.* 61(3):353-362.

Ghiringhelli F., et al., 2007, Metronomic cyclophosphamide regimen selectively depletes CD4+CD25+ regulatory T cells and restores T and NK effector functions in end stage cancer patients. *Cancer Immunol. Immunother.* 56(5): 641-648.

Goldshaid L., Rubinstein E., Brandis A., Segal D., Leshem N., Brenner O., Kalchenko V., Eren D., Yecheskel T., Salitra Y., Salomon Y. and Scherz A., 2010, Novel design principles enable specific targeting of imaging and therapeutic agents to necrotic domains in breast tumors. *Breast Cancer Research* 12:R29.

Le H. K., Graham L., Cha E., Morales J. K., Manjili M. H., and Bear H. D., 2009, Gemcitabine directly inhibits myeloid derived suppressor cells in BALB/c mice bearing 4T1 mammary carcinoma and augments expansion of T cells from tumor-bearing mice. *International Immunopharmacology* 9:900-909.

Levy M. Y., et al., 2009, Cyclophosphamide unmasks an antimetastatic effect of local tumor cryoablation. *J. Pharmacol. Exp. Ther.* 330(2):596-601.

Madondo M. T., et al., 2016, Low dose cyclophosphamide: Mechanisms of T cell modulation. *Cancer Treat. Rev.* 42: 3-9.

Marvel D., and Gabrilovich D. I., 2015, Myeloid-derived suppressor cells in the tumor microenvironment: expect the unexpected. *J. Clin. Invest.* 125(9):3356-64.

Mroz P., et al., 2010, Photodynamic therapy of tumors can lead to development of systemic antigen-specific immune response. *PLoS One* 5(12): e15194.

Najjar Y. G., and Finke J. H., 2013, Clinical perspectives on targeting of myeloid derived suppressor cells in the treatment of cancer. *Front Oncol.* 15(3):49.

Ramachandran I., Youn J. I., Gabrilovich D. I., and Condamine T., 2015, Regulation of tumor metastasis by myeloid-derived suppressor cells, *Annu. Rev. Med.* 66:97-110.

Reginato, E., et al., 2013, Photodynamic therapy plus regulatory T-cell depletion produces immunity against a mouse tumour that expresses a self-antigen. *Br. J. Cancer* 109(8):2167-2174.

Suzuki E., Kapoor V., Jassar A. S., Kaiser L. R., and Albelda S. M., 2005, Gemcitabine selectively eliminates splenic Gr-1+/CD11b+ myeloid suppressor cells in tumor-bearing animals and enhances antitumor immune activity. *Clin. Cancer Res.* 11(18): 6713-21.

Xia, Y., et al., 2014, CpG oligodeoxynucleotide as immune adjuvant enhances photodynamic therapy response in murine metastatic breast cancer. *J. Biophotonics* 7(11-12): 897-905.

The invention claimed is:

1. A method for treatment of a primary cancer solid tumor or a metastasis thereof by combination therapy, comprising administering sequentially to a patient in need thereof: (i) an anti-myeloid-derived suppressor cells (MDSCs) agent (hereinafter "anti-MDSCs agent treatment"); and (ii) a therapeutically effective amount of an anionic bacteriochlorophyll derivative (Bchl-D), optionally conjugated to an RGD-containing peptide or RGD-peptidomimetic residue, followed by photodynamic therapy (PDT) (hereinafter "PDT treatment"), wherein said anti-MDSCs agent is gemcitabine;

said anti-MDSCs agent treatment is carried out according to a metronomic chemotherapy regimen comprising from 4 to 10 administrations of the anti-MDSCs agent at determined time intervals of 5 to 12 days, wherein an interval between two such determined intervals may be longer than each determined interval, and reduces the MDSCs load;

said PDT treatment comprises a sole administration of the Bchl-D followed by illumination of the localized solid tumor to be treated; and said anti-MDSCs agent treatment and said PDT treatment are synchronized such that the outcome of said PDT treatment and the increase in the anti-tumor immunity caused thereby, in combination with the reduction in the MDSCs load caused by said anti-MDSCs agent treatment, lead to ablation of said solid tumor and elimination of micrometastases thereof.

2. The method of claim 1, wherein the anionic Bchl-D optionally conjugated with an RGD-containing peptide or RGD-peptidomimetic residue has the formula I:

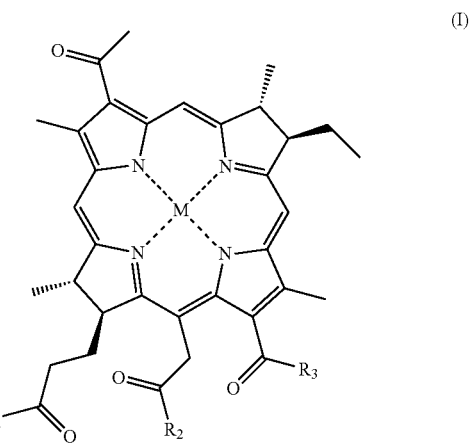

wherein

M represents 2H or Pd;

$R_1$ is O—$R_4$ or —$NHR_5$, wherein $R_4$ is H, H$^+$, an ammonium group or a monovalent metal cation selected from Na$^+$ and K$^+$, and $R_5$ is an RGD-containing peptide or RGD peptidomimetic residue;

$R_2$ is —O—$C_1$-$C_6$ alkyl;

$R_3$ is —NH—$(CH_2)_n$—$SO_3^-R_6^+$, wherein n is 2 or 3, and $R_6^+$ is a monovalent metal cation selected from Na and K$^+$; and pharmaceutically acceptable salts and optical isomers thereof.

3. The method of claim 2, wherein the anionic Bchl-D of formula I is not conjugated to an RGD-containing peptide or RGD peptidomimetic residue.

4. The method of claim 2, wherein the anionic Bchl-D of formula I is conjugated to an RGD-containing peptide or RGD peptidomimetic residue.

5. The method of claim 4, wherein the anionic Bchl-D of formula I is selected from the Bchl-Ds herein designated STL-6014, STL-6033, STL-6038, and STL-6068.

6. The method of claim 5, wherein the PDT is tissue-targeted and the localized solid tumor for treatment is illuminated at least 4 h after the conjugated Bchl-D is administered.

7. The method of claim 1, wherein the PDT treatment comprises a sole administration of the Bchl-D followed by illumination of the localized solid tumor to be treated.

8. The method of claim 1, wherein the PDT is performed with the Bchl-D STL-6014.

9. The method of claim 1, wherein the PDT is VTP that is performed with the Bchl-D WST11.

10. The method of claim 1, wherein the anti-MDSC agent is administered in a dose 3 or 4 times lower than the conventional dose of the agent in conventional monochemotherapy.

11. The method of claim 6, wherein the localized solid tumor for treatment is illuminated 6 h after the conjugated Bchl-D is administered.

12. The method of claim 3, wherein the anionic Bchl-D of formula I is selected from the Bchl-Ds herein designated WST11 and STL-7012.

13. The method of claim 8, wherein the localized solid tumor for treatment is illuminated at least 4 h after the conjugated Bchl-D is administered.

14. The method of claim 9, wherein the area to be treated is illuminated 0-30 min after the administration of the non-conjugated Bchl-D is completed.

15. The method of claim 12, wherein the PDT is vascular-targeted PDT (VTP) and the area to be treated is illuminated 0-30 min after the administration of the non-conjugated Bchl-D is completed.

16. The method of claim 3,
wherein
M represents Pd.

17. The method of claim 16, wherein said anionic Bchl-D is palladium $3^1$-oxo-15-methoxycarbonylmethyl-rhodobacteriochlorin $13^1$-(2-sulfoethyl)amide, or a salt of palladium $3^1$-oxo-15-methoxycarbonylmethyl-rhodobacteriochlorin $13^1$-(2-sulfoethyl)amide with ammonium or a monovalent alkaline metal selected from the group consisting of potassium and sodium.

18. The method of claim 17, wherein said anionic Bchl-D is palladium $3^1$-oxo-15-methoxycarbonylmethyl-rhodobacteriochlorin $13^1$-(2-sulfoethyl)amide dipotassium salt, herein designated WST11.

\* \* \* \* \*